US012577545B2

(12) United States Patent
Lee et al.

(10) Patent No.: US 12,577,545 B2
(45) Date of Patent: Mar. 17, 2026

(54) MMLV REVERSE TRANSCRIPTASE VARIANTS

(71) Applicant: 10X Genomics, Inc., Pleasanton, CA (US)

(72) Inventors: Josephine Lee, Hayward, CA (US); Samuel Marrs, San Mateo, CA (US); Geoffrey McDermott, Pleasanton, CA (US); Francesca Meschi, Pleasanton, CA (US); Luz Montesclaros, Pittsburg, CA (US); Katherine Pfeiffer, Berkeley, CA (US); Joseph Francis Shuga, Pleasanton, CA (US); Jessica Michele Terry, Pleasanton, CA (US); Solongo B. Ziraldo, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 622 days.

(21) Appl. No.: 17/114,016

(22) Filed: Dec. 7, 2020

(65) Prior Publication Data

US 2021/0115415 A1      Apr. 22, 2021

Related U.S. Application Data

(60) Division of application No. 15/975,516, filed on May 9, 2018, now abandoned, which is a continuation of application No. PCT/US2018/029641, filed on Apr. 26, 2018.

(60) Provisional application No. 62/490,492, filed on Apr. 26, 2017.

(51) Int. Cl.
| | |
|---|---|
| *C12N 15/10* | (2006.01) |
| *C12N 9/12* | (2006.01) |
| *C12Q 1/6806* | (2018.01) |
| *C12Q 1/6844* | (2018.01) |

(52) U.S. Cl.
CPC ....... *C12N 9/1276* (2013.01); *C12N 15/1065* (2013.01); *C12N 15/1096* (2013.01); *C12Q 1/6806* (2013.01); *C12Q 1/6844* (2013.01); *C12Y 207/07049* (2013.01)

(58) Field of Classification Search
CPC ......... C12N 9/12; C12N 9/1276; C12N 15/10
See application file for complete search history.

(56) References Cited

U.S. PATENT DOCUMENTS

| | | | |
|---|---|---|---|
| 6,265,552 B1 | 7/2001 | Schatz | |
| 8,541,219 B2 | 9/2013 | Potter | |
| 8,753,845 B2 | 6/2014 | Dhariwal | |
| 8,835,148 B2 * | 9/2014 | Janulaitis | C12N 15/1075 |
| | | | 435/194 |
| 9,580,698 B1 | 2/2017 | Xu | |
| 2007/0141592 A1 | 6/2007 | Smith | |
| 2008/0227661 A1 * | 9/2008 | Hogrefe | C12Q 1/686 |
| | | | 506/26 |
| 2010/0105112 A1 | 4/2010 | Holtze | |
| 2011/0065606 A1 | 3/2011 | Janulaitis | |
| 2013/0288925 A1 | 10/2013 | Janulaitis | |
| 2014/0155295 A1 | 6/2014 | Hindson | |
| 2014/0378345 A1 | 12/2014 | Hindson | |
| 2014/0378349 A1 | 12/2014 | Hindson | |
| 2015/0011430 A1 | 1/2015 | Saxonov | |
| 2015/0011432 A1 | 1/2015 | Saxonov | |
| 2015/0210989 A1 * | 7/2015 | Rogers | C12P 19/34 |
| | | | 435/91.51 |
| 2015/0376605 A1 | 12/2015 | Jarosz | |
| 2015/0376609 A1 | 12/2015 | Hindson | |
| 2015/0376700 A1 | 12/2015 | Schnall-Levin | |
| 2016/0340657 A1 | 11/2016 | Hogrefe | |
| 2018/0298414 A1 | 10/2018 | Janulaitis et al. | |
| 2018/0312822 A1 * | 11/2018 | Lee | C12N 15/1065 |
| 2024/0067940 A1 * | 2/2024 | Wilson | C12Y 207/07049 |

FOREIGN PATENT DOCUMENTS

| | | |
|---|---|---|
| CN | 1430670 A | 7/2003 |
| CN | 107058258 A | 8/2017 |
| WO | WO 01/092500 A1 | 12/2001 |
| WO | 2007022045 A2 | 2/2007 |
| WO | WO-2015/112767 A2 | 7/2015 |
| WO | WO-2015/200893 A2 | 12/2015 |
| WO | 2016040476 A1 | 3/2016 |

(Continued)

OTHER PUBLICATIONS

Siuti et al., Enzyme Reaction in Nanoporous, Picoliter Voume Containers, Analytical Chemistry, 2011, 84, 1092-1097. (Year: 2011).*

(Continued)

*Primary Examiner* — Amy M Bunker

(74) *Attorney, Agent, or Firm* — James S. Keddie; Bozicevic, Field & Francis LLP

(57) ABSTRACT

Disclosed herein, are compositions, methods, and kits comprising engineered reverse transcription enzymes that exhibit several desired properties such as thermal stability, processive reverse transcription, non-templated base addition, and template switching ability. The engineered reverse transcription enzymes described herein demonstrate unexpectedly higher resistance to cell lysate inhibition, greater ability to capture full-length mRNA transcripts, and demonstrate improved results in small reaction volumes as compared to other engineered reverse transcription enzymes.

10 Claims, 26 Drawing Sheets

Specification includes a Sequence Listing.

(56) References Cited

FOREIGN PATENT DOCUMENTS

WO          2018200867 A1      11/2018

OTHER PUBLICATIONS

Eastburn et al., Picoinjection Enables Digital Detection of RNA with Droplet RT-PCR, PLoS One, 2013, 8(4), 1-8. (Year: 2013).*

Arezi, et al., "Mutant of Moloney murine leukemia virus reverse transcriptase exhibits higher resistance to common RT-qPCR inhibitors", Anal Biochem, May 1, 20105;400(2):301-3. doi: 10.1016/j.ab.2010.01.024. Epub Jan. 25, 2010.

Arezi, et al., "Novel mutations in Moloney Murine Leukemia Virus reverse transcriptase increase thermostability through tighter binding to template-primer", Nucleic Acids Res. Feb. 2009;37(2):473-81. doi: 10.1093/nar/gkn952. Epub Dec. 4, 2008.

Baranauskas, A. et al., "Generation and characterization of new highly thermostable and processive M-MuLV reverse transcriptase variants", Protein Engineering , Design & Selection, (20121000), vol. 25, No. 10, pp. 657-668, XP055071799.

Coufal, et al., "L1 retrotransposition in human neural progenitor cells", Nature, Aug. 27, 2009;460(7259):1127-31. doi: 10.1038/nature08248. Epub Aug. 5, 2009.

Das, et al. "The Crystal Structure of the Monomeric Reverse Transcriptase from Moloney Murine Leukemia Virus", Structure. May 2004;12(5):819-29.

Das, et al., "A Directed Approach to Improving the Solubility of Moloney Murine Leukemia Virus Reverse Transcriptase", Protein Science, 2011, 10, 1936-1941. (Year: 2001).

Fang, et al., "Fluoride-cleavable biotinylation phosphoramidite for 5'-end-labeling and affinity purification of synthetic oligonucleotides", Nucleic Acids Res. Jan. 15, 2003;31(2):708-15.

Galilee, et al., "The structure of FIV reverse transcriptase and its implications for non-nucleoside inhibitor resistance", PLoS Pathog 14(1): e1006849, Jan. 24, 2018.

Huseby, et al., "Structure and Biological Activities of Beta Toxin from *Staphylococcus aureus*", Journal of Bacteriology Nov. 2007, 189 (23) 8719-8726; DOI: 10.1128/JB.00741-07.

Konishi, et al., "Stabilization of Moloney murine leukemia virus reverse transcriptase by site-directed mutagenesis of surface residue Val433", Biosci Biotechnol Biochem. 2014;78(1):75-8. doi: 10.1080/09168451.2014.877186. Epub Apr. 15, 2014.

Kruse, et al., "Structure of a mutant βtoxin from *Staphylococcus aureus* reveals domain swapping and conformational flexibility", Acta Crystallographica, (Apr. 1, 2011), vol. 67, No. 4, pp. 438-441, XP055535423.

Morgan, et al., "Chapter 12: Human microbiome analysis", PLoS Comput Biol. 2012;8(12):e1002808. doi: 10.1371/journal.pcbi.1002808. Epub Dec. 27, 2012.

Muotri, et al., "L1 retrotransposition in neurons is modulated by MeCP2", Nature. Nov. 18, 2010;468(7322):443-6. doi: 10.1038/nature09544.

Ram, et al., "Strategy for microbiome analysis using 16S rRNA gene sequence analysis on the Illumina sequencing platform", Syst Biol Reprod Med. Jun. 2011;57(3):162-70. doi: 10.3109/19396368.2011.555598. Epub 2011 Marl.

Skirgaila, et al., "Compartmentalization of destabilized enzyme-mRNA-ribosome complexes generated by ribosome display: a novel tool for the directed evolution of enzymes", Protein Eng Des Sel. Jul. 2013;26(7):453-61. doi: 10.1093/protein/gzt017. Epub May 10, 2013.

Blain, et al., "Differential Effects of Moloney Murine Leukemia Virus Reverse Transcriptase Mutations on RNase H Activity in Mg2+ and Mn2+", The Journal of Biological Chemistry, vol. 271, No. 3, pp. 1448-1454, Jan. 19, 1996.

Official Action issued in co-pending Chinese Patent Application No. 201880032804.6, dated Oct. 27, 2022.

Search Report issued in European Patent Application No. 24167618.8, dated Jul. 17, 2024.

* cited by examiner

Individual Jurkat cell

Barcode oligo
bead

Aqueous:oil partition
border

Individual Jurkat
cells

| description | 775pL GEMs CA-MMLV | 1.1nL GEMs CA-MMLV | 775pL GEMs 42B | 1.1nL GEMs 42B |
|---|---|---|---|---|
| Estimated Number of cells | 5119 | 4911 | 5325 | 5922 |
| Relative difference of detected cells from expected cells | -0.15 | -0.18 | -0.11 | -0.01 |
| Mean assembled reads per cell | 4804 | 6148 | 4251 | 3559 |
| Adjusted TRA TRB Fraction cells with full-length productive pair | 0.28 | 0.22 | 0.42 | 0.46 |
| Fraction reads mapped to recombinome | 0.86 | 0.86 | 0.71 | 0.74 |
| Valid Barcodes | 0.91 | 0.89 | 0.81 | 0.84 |
| Low-support UMI read fraction | 0.05 | 0.05 | 0.06 | 0.05 |
| Q30 Bases in RNA Read | 0.97 | 0.97 | 0.98 | 0.98 |
| VDJ Fraction corrected barcodes | 0.06 | 0.06 | 0.05 | 0.05 |
| Fraction rRNA reads | 0.010 | 0.006 | 0.096 | 0.082 |
| Fraction mtRNA reads | 0.001 | 0.001 | 0.033 | 0.025 |
| Fraction reads with any R1 sequence | 0.013 | 0.024 | 0.006 | 0.008 |
| Adjusted TRA Fraction of CDR3+ cells with >1 CDR3 | 0.09 | 0.07 | 0.14 | 0.13 |
| Adjusted TRB Fraction of CDR3+ cells with >1 CDR3 | 0.12 | 0.09 | 0.17 | 0.16 |
| Median contig length | 562 | 565 | 562 | 562 |
| Fraction unannotated contigs | 0.04 | 0.03 | 0.04 | 0.05 |
| Adjusted TRA TRB Fraction cells in a productive, full-length, and paired clonotype (INFERRED) | 0.35 | 0.29 | 0.50 | 0.54 |
| TRA TRB number of clonotypes (INFERRED) | 4183 | 3898 | 4357 | 4928 |

FIG. 22

MMLV REVERSE TRANSCRIPTASE VARIANTS

CROSS-REFERENCE

This application is a divisional of U.S. Patent Application No: 15/975,516, filed May 9, 2018, now abandoned, which is a continuation of PCT Application Serial No. PCT/US2018/029641, filed Apr. 26, 2018, which claims the benefit of U.S. Provisional Application No. 62/490,492 filed Apr. 26, 2017, all of which are incorporated by reference herein in their entirety.

SEQUENCE LISTING

The instant application incorporates by reference a Sequence Listing which was been submitted electronically in ASCII format in U.S. patent application Ser. No. 15/975,516 and is hereby incorporated by reference in its entirety. Said ASCII copy, created on Jun. 11, 2018 is named 43487763301SL.txt and is 30 kilobytes in size.

BACKGROUND

Significant advances in analyzing and characterizing biological and biochemical materials and systems have led to unprecedented advances in understanding the mechanisms of life, health, disease and treatment. Among these advances, technologies that target and characterize the genomic make up of biological systems have yielded some of the most groundbreaking results, including advances in the use and exploitation of genetic amplification technologies, and nucleic acid sequencing technologies.

Nucleic acid sequencing can be used to obtain information in a wide variety of biomedical contexts, including diagnostics, prognostics, biotechnology, and forensic biology. Sequencing may involve basic methods including Maxam-Gilbert sequencing and chain-termination methods, or de novo sequencing methods including shotgun sequencing and bridge PCR, or next-generation methods including polony sequencing, 454 pyrosequencing, Illumina sequencing, SOLiD sequencing, Ion Torrent semiconductor sequencing, HeliScope single molecule sequencing, SMRT® sequencing, and others.

Despite these advances in biological characterization, many challenges still remain unaddressed, or relatively poorly addressed by the solutions currently being offered. The present disclosure provides novel solutions and approaches to addressing many of the shortcomings of existing technologies.

SUMMARY

Disclosed herein, in some embodiments, are engineered reverse transcription enzymes, comprising an amino acid sequence that is at least 80% identical to SEQ ID NO: 3, wherein said amino acid sequence comprises: (i) a truncation of at least 15 amino acids from the N-terminus relative to SEQ ID NO: 3; and (ii) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3. In some instances, said one or more mutations are an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3. In some instances, said amino acid sequence comprises a plurality of mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3. In some instances, said engineered reverse transcription enzyme comprises: (i) three or more mutations selected from the group consisting of an L139 mutation, a D200 mutation, a T330 mutation, a P448 mutation, a D449 mutation, a D524 mutation, and a L603 mutation relative to SEQ ID NO: 3; and (ii) three or more mutations selected from the group consisting of an E69 mutation, an E302 mutation, a T306 mutation, a W313 mutation, an L435 mutation, and an N454 mutation relative to SEQ ID NO: 3. In some instances, said engineered reverse transcription enzyme comprises: (i) three or more mutations selected from the group consisting of an L139P mutation, a D200N mutation, a T330P mutation, a P448A mutation, a D449G mutation, a D524N or D524A mutation, and a L603 W mutation relative to SEQ ID NO: 3; and (ii) three or more mutations selected from the group consisting of an E69K mutation, an E302R mutation, a T306K mutation, a W313F mutation, an L435G or L435K mutation, and an N454K mutation relative to SEQ ID NO: 3. In some instances, said engineered reverse transcription enzyme comprises: an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3. In some instances, said engineered reverse transcription enzyme comprises: an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3. In some instances, said truncation comprises a truncation of at least 20 amino acids from said N-terminus relative to SEQ ID NO: 3. In some instances, said truncation comprises a truncation of 23 amino acids from said N-terminus relative to SEQ ID NO: 3. In some instances, said engineered reverse transcription enzyme further comprises an affinity tag at said N-terminus or at a C-terminus of said amino acid sequence. In some instances, said affinity tag is at least 5 histidine amino acids. In some instances, said engineered reverse transcription enzyme further comprises a protease cleavage sequence, wherein cleavage of said protease cleavage sequence by a protease results in cleavage of said affinity tag from said engineered reverse transcription enzyme. In some instances, said protease cleavage sequence is a thrombin cleavage sequence. In some instances, said amino acid sequence comprises a MRSSHHHHHHSSGLVPRGS (SEQ ID NO: 7) amino acid sequence at said N-terminus. In some instances, said engineered reverse transcription enzyme comprises an amino acid sequence according to SEQ ID NO: 6. In some instances, said engineered reverse transcription enzyme comprises an amino acid sequence according to SEQ ID NO: 5. In some instances, said engineered reverse transcription enzyme has improved ability to capture full-length transcripts as compared to a reverse transcriptase enzyme consisting of SEQ ID NO: 3. In some instances, said engineered reverse transcription enzyme has higher resistance to cell lysate as compared to a reverse transcriptase enzyme consisting of SEQ ID NO: 3. In some instances, said engineered reverse transcription enzyme has higher activity in a reaction volume of less than 1 nanoliter as compared to a reverse transcriptase enzyme consisting of SEQ ID NO: 3. In some instances, said engineered reverse transcription enzyme has increased thermal stability and reverse transcription processivity as compared to a reverse transcriptase enzyme consisting of SEQ ID NO: 3. In some instances, said engineered reverse transcription enzyme comprises terminal transferase activity and template switching ability.

Disclosed herein, in some embodiments, are methods for nucleic acid sample processing, comprising: (a) providing a template ribonucleic acid (RNA) molecule in a reaction volume, and (b) using an engineered reverse transcription enzyme to reverse transcribe said RNA molecule to a complementary DNA molecule, wherein said engineered reverse transcription enzyme comprises an amino acid sequence that is at least 80% identical to SEQ ID NO: 3, wherein said amino acid sequence comprises: (i) a truncation of at least 15 amino acids from the N-terminus relative to SEQ ID NO: 3; and (ii) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3. In some instances, said reaction volume is less than 1 nanoliter. In some instances, said reaction volume is less than 500 picoliters. In some instances, said reaction volume is a droplet in an emulsion. In some instances, said reaction volume is a well. In some instances, said reaction volume further comprises a plurality of nucleic acid barcode molecules comprising a barcode sequence. In some instances, said RNA molecule is a messenger RNA (mRNA) molecule, wherein said plurality of nucleic acid barcode molecules further comprise an oligo(dT) sequence, and wherein said engineered reverse transcription enzyme reverse transcribes said mRNA molecule into said complementary DNA molecule using said oligo(dT) sequence, wherein said complementary DNA molecule comprises said barcode sequence. In some instances, said RNA molecule is a messenger RNA (mRNA) molecule, wherein said reaction volume further comprises a nucleic acid molecule comprising an oligo(dT) sequence, wherein said plurality of nucleic acid barcode molecules further comprise a template switching sequence, wherein said engineered reverse transcription enzyme reverse transcribes said mRNA molecule using said nucleic acid molecule comprising said oligo(dT) sequence, and wherein said engineered reverse transcription enzyme performs a template switching reaction, thereby generating said complementary DNA molecule, wherein said complementary DNA molecule comprises said barcode sequence. In some instances, said plurality of nucleic acid barcode molecules are attached to a support. In some instances, said nucleic acid barcode molecules are releasably attached to said support. In some instances, said support is a bead. In some instances, said bead is a gel bead. In some instances, said nucleic acid barcode molecules are covalently attached to said bead. In some instances, said nucleic acid barcode molecules are releasably attached to said bead. In some instances, said nucleic acid barcode molecules are released upon application of a stimulus. In some instances, said stimulus is a chemical stimulus. In some instances, said chemical stimulus is a reducing agent. In some instances, said gel bead is a degradable gel bead. In some instances, said degradable gel bead comprises chemically cleavable cross-linking. In some instances, said chemically cleavable cross-linking comprises disulfide cross-linking. In some instances, said reaction volume comprises a cell comprising said RNA molecule. In some instances, the method further comprises releasing said RNA molecule from said cell.

Disclosed herein, in some embodiments, are kits for performing a reverse transcription reaction, comprising: (a) an engineered reverse transcription enzyme comprising (i) a truncation of at least 15 amino acids from the N-terminus relative to SEQ ID NO: 3; and (ii) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3; and (b) instructions for using said engineered reverse transcription enzyme to perform a reverse transcription reaction. In some instances, said kit further comprises a reaction buffer for performing said reverse transcription reaction. In some instances, said kit further comprises dNTPs. In some instances, said engineered reverse transcription enzyme, said buffer, and said dNTPs are provided together in a master mix solution. In some instances, said master mix is present at a concentration at least two times the working concentration indicated in said instructions for use in said reverse transcription reaction. In some instances, said kit further comprises a primer for priming said reverse transcription reaction. In some instances, said primer is a poly-dT primer, a random N-mer primer, or a target-specific primer.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 10 discloses AAAAAAAAAAAAAAAAA as SEQ ID NO:10.

FIG. 11 discloses AAAAAAAAAA as SEQ ID NO:11.

FIG. 22 shows various exemplary results from a TCR transcriptional profiling prepared from droplets containing an engineered RT enzyme compared to a commercially available counterpart.

DETAILED DESCRIPTION

Figure 1:
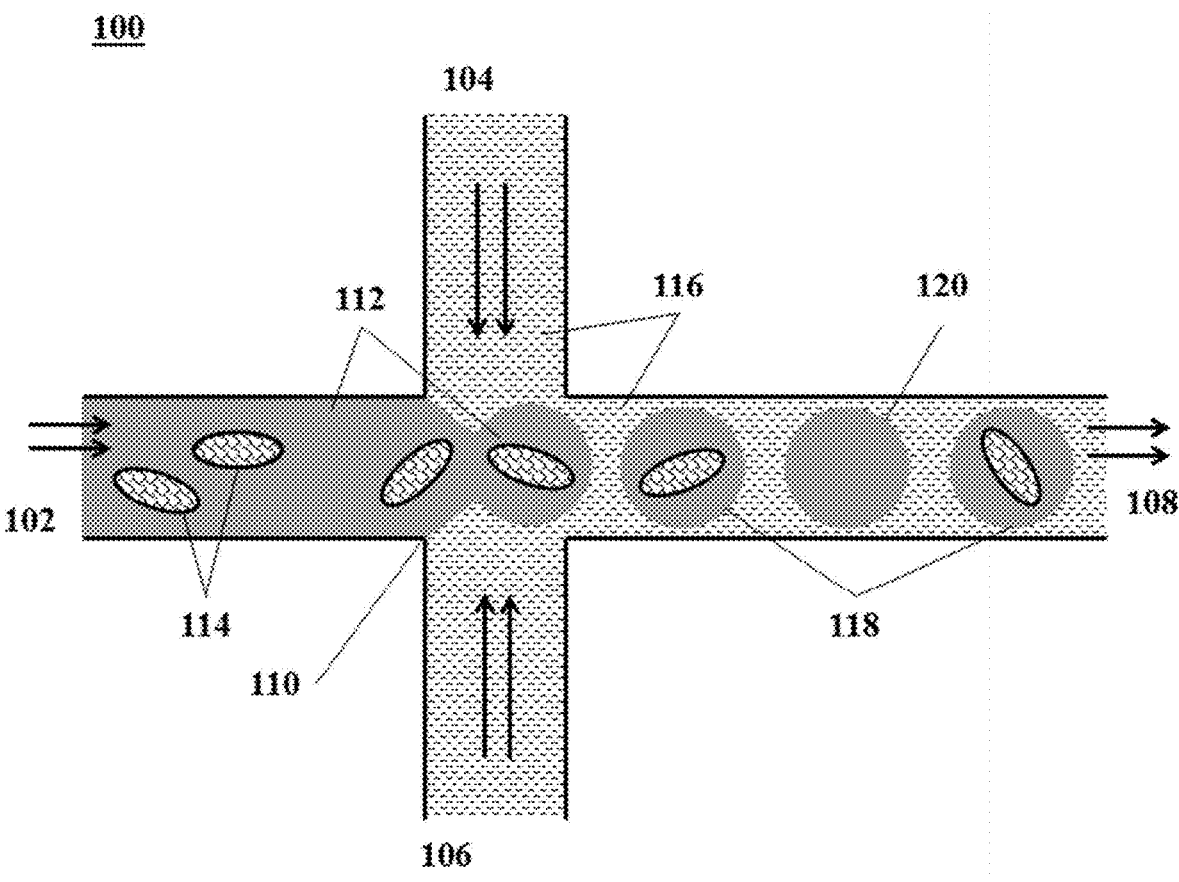
FIG. 1 shows an example of a microfluidic channel structure for partitioning individual or small groups of cells.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

I. Single Cell Analysis

Advanced nucleic acid sequencing technologies have yielded monumental results in sequencing biological materials, including providing substantial sequence information on individual organisms, and relatively pure biological samples. However, these systems have not proven effective at being able to identify and characterize sub-populations of cells in biological samples that may represent a smaller minority of the overall make-up of the sample, but for which individualized sequence information could prove even more valuable.

Most nucleic acid sequencing technologies derive the nucleic acids that they sequence from collections of cells derived from tissue or other samples. The cells can be processed, en masse, to extract the genetic material that represents an average of the population of cells, which can then be processed into sequencing ready DNA libraries that are configured for a given sequencing technology. As will be appreciated, although often discussed in terms of DNA or nucleic acids, the nucleic acids derived from the cells may include DNA, or RNA, including, e.g., mRNA, total RNA, or the like, that may be processed to produce cDNA for sequencing, e.g., using any of a variety of RNA-seq methods. Following from this processing, absent a cell specific marker, attribution of genetic material as being contributed by a subset of cells or all cells in a sample is virtually impossible in such an ensemble approach.

In addition to the inability to attribute characteristics to particular subsets of populations of cells, such ensemble sample preparation methods also are, from the outset, predisposed to primarily identifying and characterizing majority constituents in the sample of cells, and are not designed to be able to pick out the minority constituents, e.g., genetic material contributed by one cell, a few cells, or a small percentage of total cells in the sample. Likewise, where analyzing expression levels, e.g., of mRNA, an ensemble approach would be predisposed to presenting potentially grossly inaccurate data from cell populations that are non-homogeneous in terms of expression levels. In some cases, where expression is high in a small minority of the cells in an analyzed population, and absent in the majority of the cells of the population, an ensemble method would indicate low level expression for the entire population.

This original majority bias is further magnified, and even overwhelming, through processing operations used in building up the sequencing libraries from these samples. In particular, most next generation sequencing technologies rely upon the geometric amplification of nucleic acid fragments, such as the polymerase chain reaction, in order to produce sufficient DNA for the sequencing library. However, such geometric amplification is biased toward amplification of majority constituents in a sample, and may not preserve the starting ratios of such minority and majority components. By way of example, if a sample includes 95% DNA from a particular cell type in a sample, e.g., host tissue cells, and 5% DNA from another cell type, e.g., cancer cells, PCR based amplification can preferentially amplify the majority DNA in place of the minority DNA, both as a function of comparative exponential amplification (the repeated doubling of the higher concentration quickly outpaces that of the smaller fraction) and as a function of sequestration of amplification reagents and resources (as the larger fraction is amplified, it preferentially utilizes primers and other amplification reagents).

While some of these difficulties may be addressed by utilizing different sequencing systems, such as single molecule systems that don't require amplification, the single molecule systems, as well as the ensemble sequencing methods of other next generation sequencing systems, can also have requirements for sufficiently large input requirements.

II. Compartmentalization and Characterization of Cells

Disclosed herein, however, are methods and systems for characterizing nucleic acids from small populations of cells, and in some cases, for characterizing nucleic acids from individual cells, especially in the context of larger populations of cells. The methods and systems provide advantages of being able to provide the attribution advantages of the non-amplified single molecule methods with the high throughput of the other next generation systems, with the additional advantages of being able to process and sequence extremely low amounts of input nucleic acids derivable from individual cells or small collections of cells.

In particular, the methods described herein compartmentalize the analysis of individual cells or small populations of cells, including e.g., nucleic acids from individual cells or small groups of cells, and then allow that analysis to be attributed back to the individual cell or small group of cells from which the nucleic acids were derived. This can be accomplished regardless of whether the cell population represents a 50/50 mix of cell types, a 90/10 mix of cell types, or virtually any ratio of cell types, as well as a complete heterogeneous mix of different cell types, or any mixture between these. Differing cell types may include cells or biologic organisms from different tissue types of an individual, from different individuals, from differing genera, species, strains, variants, or any combination of any or all of the foregoing. For example, differing cell types may include normal and tumor tissue from an individual, multiple different bacterial species, strains and/or variants from environmental, forensic, microbiome or other samples, or any of a variety of other mixtures of cell types.

In one aspect, the methods and systems described herein, provide for the compartmentalization, depositing or partitioning of the nucleic acid contents of individual cells from a sample material containing cells, into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more cells. A partition may include one or more types of cells. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a cell encased inside of a gel or polymer matrix, such as via polymerization of a droplet containing the cell and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of the nucleic acid contents of individual cells, including porous membranes through which aqueous mixtures of cells are extruded into non-aqueous fluids.

As used herein, in some aspects, the partitions refer to containers or vessels (such as wells, microwells, tubes, through ports in nanoarray substrates, e.g., BioTrove nanoarrays, or other containers). In many some aspects, however, the compartments or partitions comprise partitions that are flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual cells to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of cells per partition, number of beads per partition, etc.). For example, partition occupancy can be controlled by providing the aqueous stream at a certain concentration and/or flow rate of particles. To generate single cell partitions, the relative flow rates of the immiscible fluids can be selected such that, on average, the partitions may contain less than one cell per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

In certain cases, microfluidic channel networks are particularly suited for generating partitions as described herein. Examples of such microfluidic devices include those described in detail in Provisional U.S. Patent Application No. 61/977,804, filed Apr. 4, 2014, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

FIG. 1 shows an example of a microfluidic channel structure 100 for partitioning individual cell. The channel structure 100 can include channel segments 102, 104, 106 and 108 communicating at a channel junction 110. In operation, a first aqueous fluid 112 that includes suspended individual cells 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual cell 114 (such as droplets 118). A discrete droplet generated may include more than one individual cell 114 (not shown in FIG. 1). A discrete droplet may contain no cell 114 (such as droplet 120). Each discrete partition may maintain separation of its own contents (e.g., individual cell 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., cells, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more cells 114, and (2) unoccupied droplets 120, not containing any cells 114. Occupied droplets 118 may comprise singly occupied droplets (having one cell) and multiply occupied droplets (having more than one cell). As described elsewhere herein, in some cases, the majority of occupied partitions can include no more than one cell per occupied partition and some of the generated partitions can be unoccupied (of any cell). In some cases, though, some of the occupied partitions may include more than one cell. In many cases, the systems and methods are used to ensure that the substantial majority of occupied partitions (partitions containing one or more microcapsules) include no more than 1 cell per occupied partition. In some cases, the partitioning process may be controlled such that fewer than about 25% of the occupied partitions contain more than one cell, and in many cases, fewer than about 20% of the occupied partitions have more than one cell, while in some cases, fewer than about 10% or even fewer than about 5% of the occupied partitions include more than one cell per partition.

In some cases, it may be desirable to minimize the creation of excessive numbers of empty partitions, such as to reduce costs and/or increase efficiency. While this minimization may be achieved by providing a sufficient number of cells (e.g., 114) at the partitioning junction 110, such as to ensure that at least one cell is encapsulated in a partition, the Poissonian distribution may expectedly increase the number of partitions that include multiple cells. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied. As such, in accordance with aspects described herein, the flow of one or more of the cells, or other fluids directed into the partitioning zone are controlled such that, in many cases, no more than 50% of the generated partitions are unoccupied, i.e., including less than 1 cell, no more than 25% of the generated partitions, no more than 10% of the generated partitions, may be unoccupied. Further, in some aspects, these flows are controlled so as to present non-poissonian distribution of single occupied partitions while providing lower levels of unoccupied partitions. Restated, in some aspects, the above noted ranges of unoccupied partitions can be achieved while still providing any of the single occupancy rates described above. For example, in many cases, the use of the systems and methods described herein creates resulting partitions that have multiple occupancy rates of from less than 25%, less than 20%, less than 15%, less than 10%, and in many cases, less than 5%, while having unoccupied partitions of from less than 50%, less than 40%, less than 30%, less than 20%, less than 10%, and in some cases, less than 5%.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
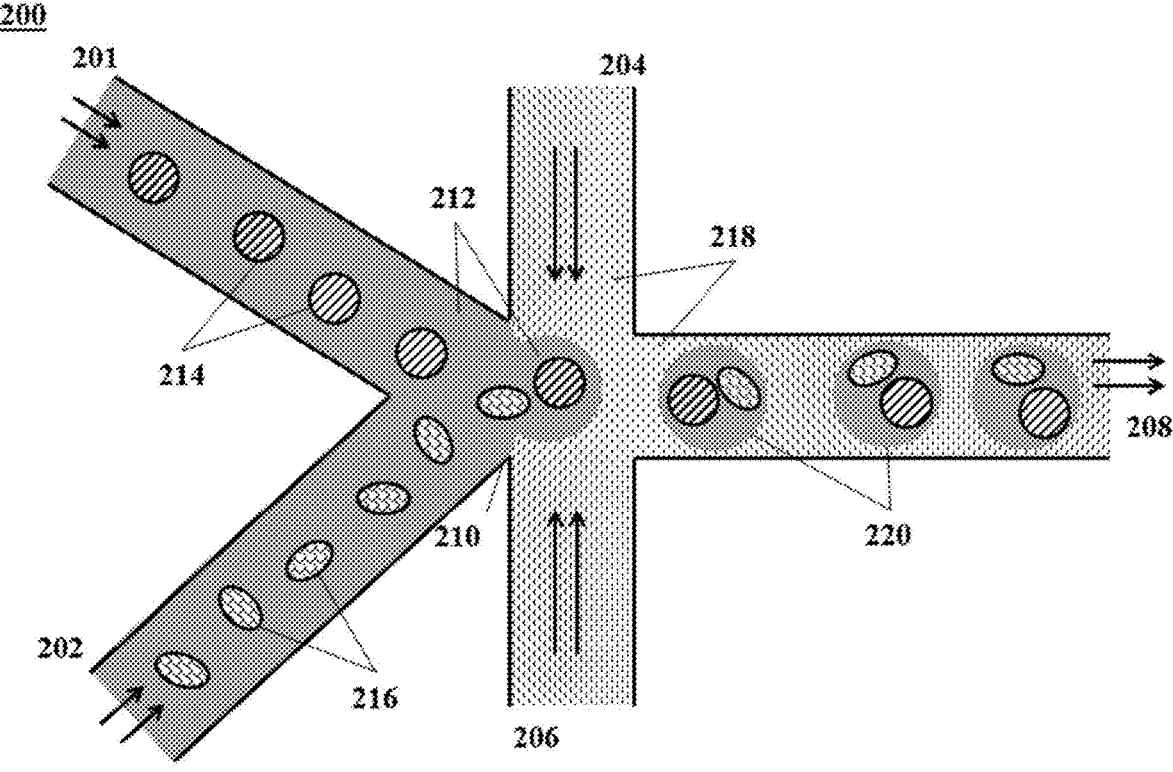
FIG. 2 shows an example of a microfluidic channel structure for co-partitioning cells and beads or microcapsules comprising additional reagents.

As will be appreciated, the above-described occupancy rates are also applicable to partitions that include both cells and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a cell. In particular, it may be desirable to provide that at least 50% of the partitions are occupied by at least one cell and at least one bead, or at least 75% of the partitions may be so occupied, or even at least 80% or at least 90% of the partitions may be so occupied. Further, in those cases where it is desired to provide a single cell and a single bead within a partition, at least 50% of the partitions can be so occupied, at least 60%, at least 70%, at least 80% or even at least 90% of the partitions can be so occupied.

In another aspect, in addition to or as an alternative to droplet based partitioning, cells may be encapsulated within a microcapsule that comprises an outer shell, layer or porous matrix in which is entrained one or more individual cells or small groups of cells. The microcapsule may include other reagents. Encapsulation of cells may be performed by a variety of processes. Such processes may combine an aqueous fluid containing the cells with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through crosslinking, polymerization initiation of the precursor (e.g., through added initiators)), mechanical stimuli, or a combination thereof.

Preparation of microcapsules comprising cells may be performed by a variety of methods. For example, air knife droplet or aerosol generators may be used to dispense droplets of precursor fluids into gelling solutions in order to form microcapsules that include individual cells or small groups of cells. Likewise, membrane based encapsulation systems may be used to generate microcapsules comprising encapsulated cells as described herein. Microfluidic systems of the present disclosure, such as that shown in FIG. 1, may be readily used in encapsulating cells as described herein. In particular, and with reference to FIG. 1, the aqueous fluid 112 comprising (i) the individual cells 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained cells. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethyl-methylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated cells can be selectively releasable from the microcapsule, such as through passage of time or upon application of a particular stimulus, that degrades the microcapsule sufficiently to allow the cell, or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The cell can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the cell. The polymer or gel may be diffusively permeable to chemical or biochemical reagents. The polymer or gel may be diffusively impermeable to macromolecular constituents of the cell. In this manner, the polymer or gel may act to allow the cell to be subjected to chemical or biochemical operations while spatially confining the nucleic acids to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the cell may be surrounded by polyacrylamide strands linked together by disulfide bridges. In this manner, the cell may be encased inside of or comprise a gel or matrix (e.g., polymer matrix) to form a "cell bead." A cell bead can contain a cell or nucleic acids (e.g., RNA, DNA) of individual cells. A cell bead may include a single cell or multiple cells, or a derivative of the single cell or multiple cells. For example after lysing and washing the cells, inhibitory components from cell lysates can be washed away and the nucleic acids can be bound as cell beads. Systems and methods disclosed herein can be applicable to both cell beads (and/or droplets or other partitions) containing individual cells and cell beads (and/or droplets or other partitions) containing nucleic acids of individual cells.

Encapsulated cells or cell populations can provide certain potential advantages of being more storable and more portable than droplet-based partitioned cells. Furthermore, in some cases, it may be desirable to allow cells to incubate for a select period of time before analysis, such as in order to characterize changes in such cells over time, either in the presence or absence of different stimuli. In such cases, encapsulation may allow for longer incubation than partitioning in emulsion droplets, although in some cases, droplet partitioned cells may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of cells may constitute the partitioning of the cells into which other reagents are co-partitioned. Alternatively or in addition, encapsulated cells may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned cell. For example, barcodes may be injected into droplets previous to, subsequent to, or concurrently with droplet generation. The delivery of the barcodes to a particular partition allows for the later attribution of the characteristics of the individual cell to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of cells 216 along the channel segment 202 into junction 210. The plurality of cells 216 may be sourced from a suspension of cells. For example, the channel segment 202 may be connected to a reservoir comprising an aqueous suspension of cells 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and cells may form a mixture that is directed along another channel to the junction 210 to yield droplets 220. The mixture may provide the beads and cells in an alternating fashion, such that, for example, a droplet comprises a single bead and a single cell.

Beads, cells and droplets may flow along channels at substantially regular flow profiles (e.g., at regular flow rates). Such regular flow profiles may permit a droplet to include a single bead and a single cell. Such regular flow profiles may permit the droplets to have an occupancy (e.g., droplets having beads and cells) greater than 5%, 10%, 20%, 30%, 40%, 50%, 60%, 70%, 80%, 90%, or 95%. Such regular flow profiles and devices that may be used to provide such regular flow profiles are provided in, for example, U.S.

Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual cell 216. A discrete droplet that is generated may include a barcode or other reagent carrying bead 214. A discrete droplet generated may include both an individual cell and a barcode carrying bead, such as droplets 220. In some instances, a discrete droplet may include more than one individual cell or no cells. In some instances, a discrete droplet may include more than one bead or no bead. A discrete droplet may be unoccupied (e.g., no beads, no cells).

Beneficially, a discrete droplet partitioning a cell and a barcode carrying bead may effectively allow the attribution of the barcode to nucleic acids of the cell within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (μm), 5 μm, 10 μm, 20 μm, 30 μm, 40 μm, 50 μm, 60 μm, 70 μm, 80 μm, 90 μm, 100 μm, 250 μm, 500 μm, 1 mm, or greater. In some cases, a bead may have a diameter of less than about 10 nm, 100 nm, 500 nm, 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or less. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

In operation, a cell can be co-partitioned along with a barcode bearing bead. The barcoded nucleic acid molecules can be released from the bead in the partition. By way of example, in the context of analyzing sample RNA, the poly-dT (poly-deoxythymine, also referred to as oligo (dT)) segment of one of the released nucleic acid molecules can hybridize to the poly-A tail of a mRNA molecule. Reverse transcription may result in a cDNA transcript of the mRNA, but which transcript includes each of the sequence segments of the nucleic acid molecule. Because the nucleic acid molecule comprises an anchoring sequence, it will more likely hybridize to and prime reverse transcription at the sequence end of the poly-A tail of the mRNA. Within any given partition, all of the cDNA transcripts of the individual mRNA molecules may include a common barcode sequence segment. However, the transcripts made from the different mRNA molecules within a given partition may vary at the unique molecular identifying sequence segment (e.g., UMI segment). Beneficially, even following any subsequent amplification of the contents of a given partition, the number of different UMIs can be indicative of the quantity of mRNA originating from a given partition, and thus from the cell. As noted above, the transcripts can be amplified, cleaned up and sequenced to identify the sequence of the cDNA transcript of the mRNA, as well as to sequence the barcode segment and the UMI segment. While a poly-dT primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligo-nucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endo-nucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonu-clease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the cell and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of cells (e.g., one cell and one bead per partition).

The partitions described herein may comprise small volumes, for example, less than about 10 microliters (4), 54, 14, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, the cells may be partitioned along with lysis reagents in order to release the contents of the cells within the partition. In such cases, the lysis agents can be contacted with the cell suspension concurrently with, or immediately prior to the introduction of the cells into the partitioning junction/droplet generation zone (e.g., junction 210), such as through an additional channel or channels upstream of the channel junction. Beneficially, when lysis reagents and biological particles are co-partitioned, the lysis reagents can facilitate the release of the contents of the biological particles within the partition.

The contents released in a partition may remain discrete from the contents of other partitions.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the cells to cause the release of the cell's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of cells that may be in addition to or in place of droplet partitioning, where any pore size of the encapsulate is sufficiently small to retain nucleic acid fragments of a given size, following cellular disruption.

Alternatively or in addition to the lysis agents co-partitioned with the cells described above, other reagents can also be co-partitioned with the cells, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated cells, the cells may be exposed to an appropriate stimulus to release the cells or their contents from a co-partitioned microcapsule. For example, in some cases, a chemical stimulus may be co-partitioned along with an encapsulated cell to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated cell to be released into a partition at a different time from the release of nucleic acid molecules into the same partition.

As will be appreciated, a number of other reagents may be co-partitioned along with the cells, beads, lysis agents and chemical stimuli, including, for example, protective reagents, like proteinase K, chelators, nucleic acid extension, replication, transcription or amplification reagents such as polymerases, reverse transcriptases, transposases which can be used for transposon based methods (e.g., Nextera), nucleoside triphosphates or NTP analogues, primer sequences and additional cofactors such as divalent metal ions used in such reactions, ligation reaction reagents, such as ligase enzymes and ligation sequences, dyes, labels, or other tagging reagents.

Additional reagents may also be co-partitioned with the cells, such as endonucleases to fragment a cell's DNA, DNA polymerase enzymes and dNTPs used to amplify the cell's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutyn1-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the nucleic acids contained therein may be further processed within the partitions. In accordance with the methods and systems described herein, the nucleic acid contents of individual cells can be provided with unique identifiers such that, upon characterization of those nucleic acids they may be attributed as having been derived from the same cell or cells. The ability to attribute characteristics to individual cells or groups of cells is provided by the assignment of unique identifiers specifically to an individual cell or groups of cells, which is another advantageous aspect of the methods and systems described herein. In particular, unique identifiers, e.g., in the form of nucleic acid barcodes are assigned or associated with individual cells or populations of cells, in order to tag or label the cell's components (and as a result, its characteristics) with the unique identifiers. These unique identifiers are then used to attribute the cell's components and characteristics to an individual cell or group of cells.

In some aspects, this is carried out by co-partitioning the individual cells or groups of cells with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual cell, or to other components of the cell, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned oligonucleotides can also comprise other functional sequences useful in the processing of the nucleic acids from the co-partitioned cells. These sequences include, e.g., targeted or random/universal amplification primer sequences for amplifying the genomic DNA from the individual cells within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 8:
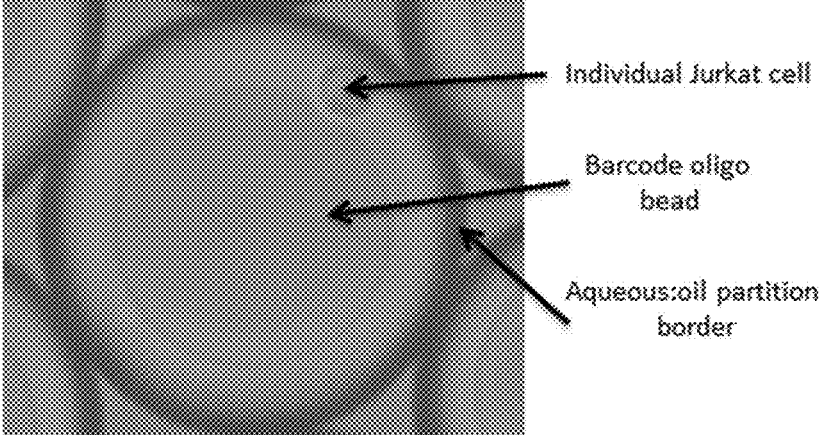
FIG. 8 provides an image of individual cells co-partitioned along with individual barcode bearing beads FIG. 9A-FIG. 9E provides schematic illustration of example barcoded oligonucleotide structures for use in analysis of RNA and example operations for performing RNA analysis.
Figure 8:
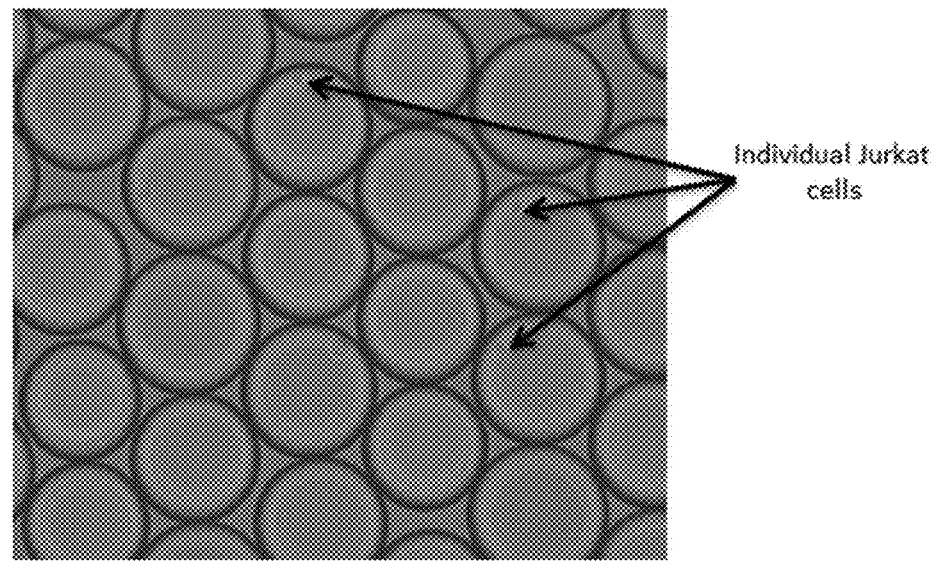

FIG. 8 shows images of individual Jurkat cells co-partitioned along with barcode oligonucleotide containing beads in aqueous droplets in an aqueous in oil emulsion. As illustrated, individual cells may be readily co-partitioned with individual beads. As will be appreciated, optimization of individual cell loading may be carried out by a number of methods, including by providing dilutions of cell populations into the microfluidic system in order to achieve the desired cell loading per partition as described elsewhere herein.

In operation, once lysed, the nucleic acid contents of the individual cells are then available for further processing within the partitions, including, e.g., fragmentation, amplification and barcoding, as well as attachment of other functional sequences. As noted above, fragmentation may be accomplished through the co-partitioning of shearing enzymes, such as endonucleases, in order to fragment the nucleic acids into smaller fragments. These endonucleases may include restriction endonucleases, including type II and type IIs restriction endonucleases as well as other nucleic acid cleaving enzymes, such as nicking endonucleases, and the like. In some cases, fragmentation may not be desired, and full length nucleic acids may be retained within the partitions, or in the case of encapsulated cells or cell contents, fragmentation may be carried out prior to partitioning, e.g., through enzymatic methods, e.g., those described herein, or through mechanical methods, e.g., mechanical, acoustic or other shearing.

Once co-partitioned, and the cells are lysed to release their nucleic acids, the oligonucleotides disposed upon the bead may be used to barcode and amplify fragments of those nucleic acids. A particularly elegant process for use of these barcode oligonucleotides in amplifying and barcoding fragments of sample nucleic acids is described in detail in U.S. Patent Publication No. US 2014/0378345, filed Jun. 26, 2014, and incorporated by reference herein. Briefly, in one aspect, the oligonucleotides present on the beads that are co-partitioned with the cells, are released from their beads into the partition with the cell's nucleic acids. The oligonucleotides can include, along with the barcode sequence, a primer sequence at its 5'end. This primer sequence may be a random oligonucleotide sequence intended to randomly prime numerous different regions on the cell's nucleic acids, or it may be a specific primer sequence targeted to prime upstream of a specific targeted region of the cell's genome.

Figure 3:
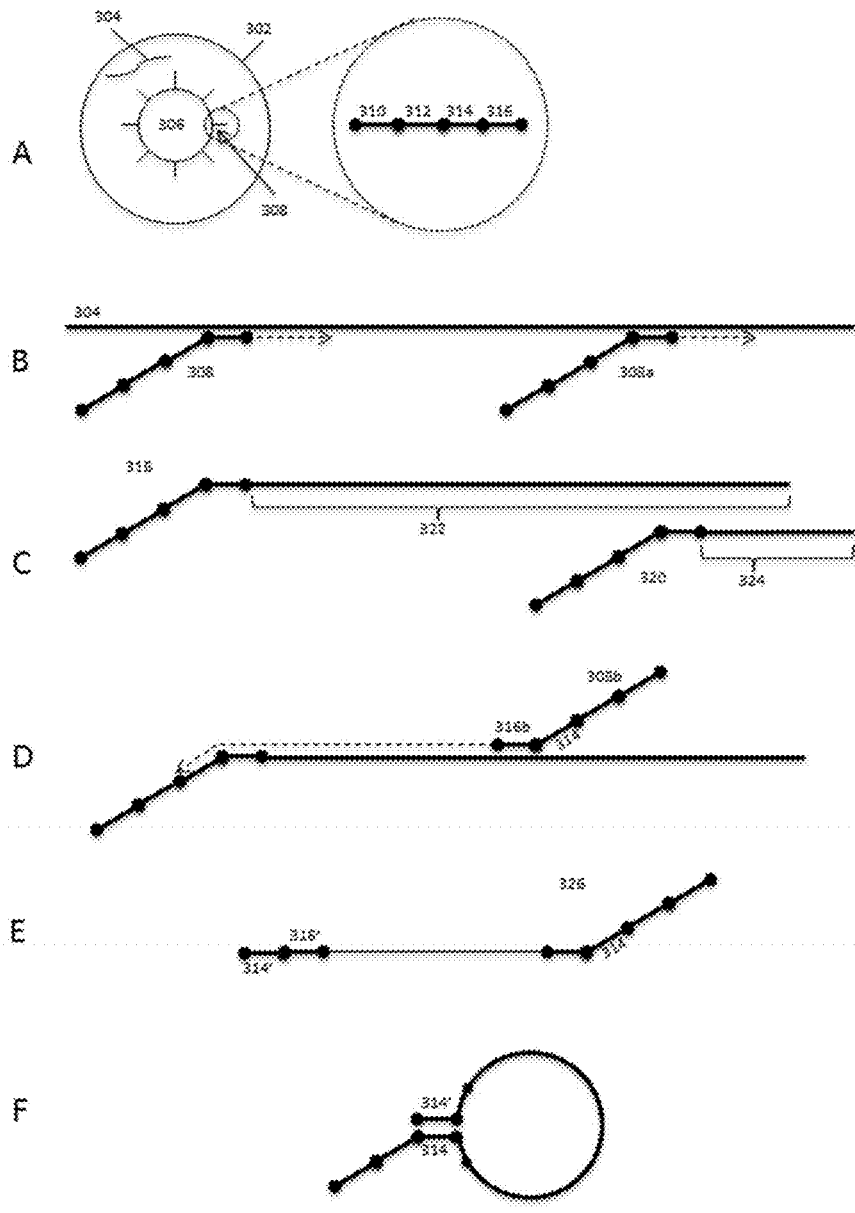
FIG. 3 schematically illustrates an example process for amplification and barcoding of cell's nucleic acids.

Once released, the primer portion of the oligonucleotide can anneal to a complementary region of the cell's nucleic acid. Extension reaction reagents, e.g., DNA polymerase, nucleoside triphosphates, co-factors (e.g., $Mg^{2+}$ or $Mn^{2+}$), that are also co-partitioned with the cells and beads, then extend the primer sequence using the cell's nucleic acid as a template, to produce a complementary fragment to the strand of the cell's nucleic acid to which the primer annealed, which complementary fragment includes the oligonucleotide and its associated barcode sequence. Annealing and extension of multiple primers to different portions of the cell's nucleic acids will result in a large pool of overlapping complementary fragments of the nucleic acid, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow formation of a hairpin structure or partial hairpin structure, the reduces the ability of the molecule to be the basis for producing further iterative copies. As described herein, the cell's nucleic acids may include any desired nucleic acids within the cell including, for example, the cell's DNA, e.g., genomic DNA, RNA, e.g., messenger RNA, and the like. For example, in some cases, the methods and systems described herein are used in characterizing expressed mRNA, including, e.g., the presence and quantification of such mRNA, and may include RNA sequencing processes as the characterization process. Alternatively or additionally, the reagents partitioned along with the cells may include reagents for the conversion of mRNA into cDNA, e.g., reverse transcriptase enzymes and reagents, to facilitate sequencing processes where DNA sequencing is employed. In some cases, where the nucleic acids to be characterized comprise RNA, e.g., mRNA, schematic illustration of one example of this is shown in FIG. 3.

As shown, oligonucleotides that include a barcode sequence are co-partitioned in, e.g., a droplet 302 in an emulsion, along with a sample nucleic acid 304. As noted elsewhere herein, the oligonucleotides 308 may be provided on a bead 306 that is co-partitioned with the sample nucleic acid 304, which oligonucleotides are releasable from the bead 306, as shown in panel A. The oligonucleotides 308 include a barcode sequence 312, in addition to one or more functional sequences, e.g., sequences 310, 314 and 316. For example, oligonucleotide 308 is shown as comprising barcode sequence 312, as well as sequence 310 that may function as an attachment or immobilization sequence for a given sequencing system, e.g., a P5 sequence used for attachment in flow cells of an Illumina Hiseq® or Miseq® system. As shown, the oligonucleotides also include a primer sequence 316, which may include a random or targeted N-mer for priming replication of portions of the sample nucleic acid 304. Also included within oligonucleotide 308 is a sequence 314 which may provide a sequencing priming region, such as a "read1" or R1 priming region, that is used to prime polymerase mediated, template directed sequencing by synthesis reactions in sequencing systems. As will be appreciated, the functional sequences may be selected to be compatible with a variety of different sequencing systems, e.g., 454 Sequencing, Ion Torrent Proton or PGM, Illumina X10, etc., and the requirements thereof. In many cases, the barcode sequence 312, immobilization sequence 310 and R1 sequence 314 may be common to all of the oligonucleotides attached to a given bead. The primer sequence 316 may vary for random N-mer primers, or may be common to the oligonucleotides on a given bead for certain targeted applications.

As will be appreciated, in some cases, the functional sequences may include primer sequences useful for RNA-seq applications. For example, in some cases, the oligonucleotides may include poly-dT primers for priming reverse transcription of RNA for RNA-seq. In still other cases, oligonucleotides in a given partition, e.g., included on an individual bead, may include multiple types of primer sequences in addition to the common barcode sequences, such as both DNA-sequencing and RNA sequencing primers, e.g., poly-dT primer sequences included within the oligonucleotides coupled to the bead. In such cases, a single partitioned cell may be both subjected to DNA and RNA sequencing processes.

Based upon the presence of primer sequence 316, the oligonucleotides can prime the sample nucleic acid as shown in panel B, which allows for extension of the oligonucleotides 308 and 308a using polymerase enzymes and other extension reagents also co-partitioned with the bead 306 and sample nucleic acid 304. As shown in panel C, following extension of the oligonucleotides that, for random N-mer primers, would anneal to multiple different regions of the sample nucleic acid 304; multiple overlapping complements or fragments of the nucleic acid are created, e.g., fragments 318 and 320. Although including sequence portions that are complementary to portions of sample nucleic acid, e.g., sequences 322 and 324, these constructs are generally referred to herein as comprising fragments of the sample nucleic acid 304, having the attached barcode sequences.

The barcoded nucleic acid fragments may then be subjected to characterization, e.g., through sequence analysis, or they may be further amplified in the process, as shown in panel D. For example, additional oligonucleotides, e.g., oligonucleotide 308b, also released from bead 306, may prime the fragments 318 and 320. This shown in for fragment 318. In particular, again, based upon the presence of the random N-mer primer 316b in oligonucleotide 308b (which in many cases can be different from other random N-mers in a given partition, e.g., primer sequence 316), the oligonucleotide anneals with the fragment 318, and is extended to create a complement 326 to at least a portion of fragment 318 which includes sequence 328, that comprises a duplicate of a portion of the sample nucleic acid sequence. Extension of the oligonucleotide 308b continues until it has replicated through the oligonucleotide portion 308 of fragment 318. As noted elsewhere herein, and as illustrated in panel D, the oligonucleotides may be configured to prompt a stop in the replication by the polymerase at a desired point, e.g., after replicating through sequences 316 and 314 of oligonucleotide 308 that is included within fragment 318. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 312 to prevent a non-uracil tolerant polymerase to cease replication of that region. As a result a fragment 326 is created that includes the full-length oligonucleotide 308b at one end, including the barcode sequence 312, the attachment sequence 310, the R1 primer region 314, and the random N-mer sequence 316b. At the other end of the sequence may be included the complement 316' to the random N-mer of the first oligonucleotide 308, as well as a complement to all or a portion of the R1 sequence, shown as sequence 314'. The R1 sequence 314 and its complement 314' are then able to hybridize together to form a partial hairpin structure 328. As will be appreciated because the random N-mers differ among different oligonucleotides, these sequences and their complements would not be expected to participate in hairpin formation, e.g., sequence 316', which is the complement to random N-mer 316, would not be expected to be complementary to random N-mer sequence 316b. This would not be the case for other applications, e.g., targeted primers, where the N-mers would be common among oligonucleotides within a given partition.

By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 326.

In general, the amplification of the cell's nucleic acids is carried out until the barcoded overlapping fragments within the partition constitute at least 1× coverage of the particular portion or all of the cell's genome, at least 2×, at least 3×, at least 4×, at least 5×, at least 10×, at least 20×, at least 40× or more coverage of the genome or its relevant portion of interest. Once the barcoded fragments are produced, they may be directly sequenced on an appropriate sequencing system, e.g., an Illumina Hiseq®, Miseq® or X10 system, or they may be subjected to additional processing, such as further amplification, attachment of other functional sequences, e.g., second sequencing primers, for reverse reads, sample index sequences, and the like.

Figure 4:
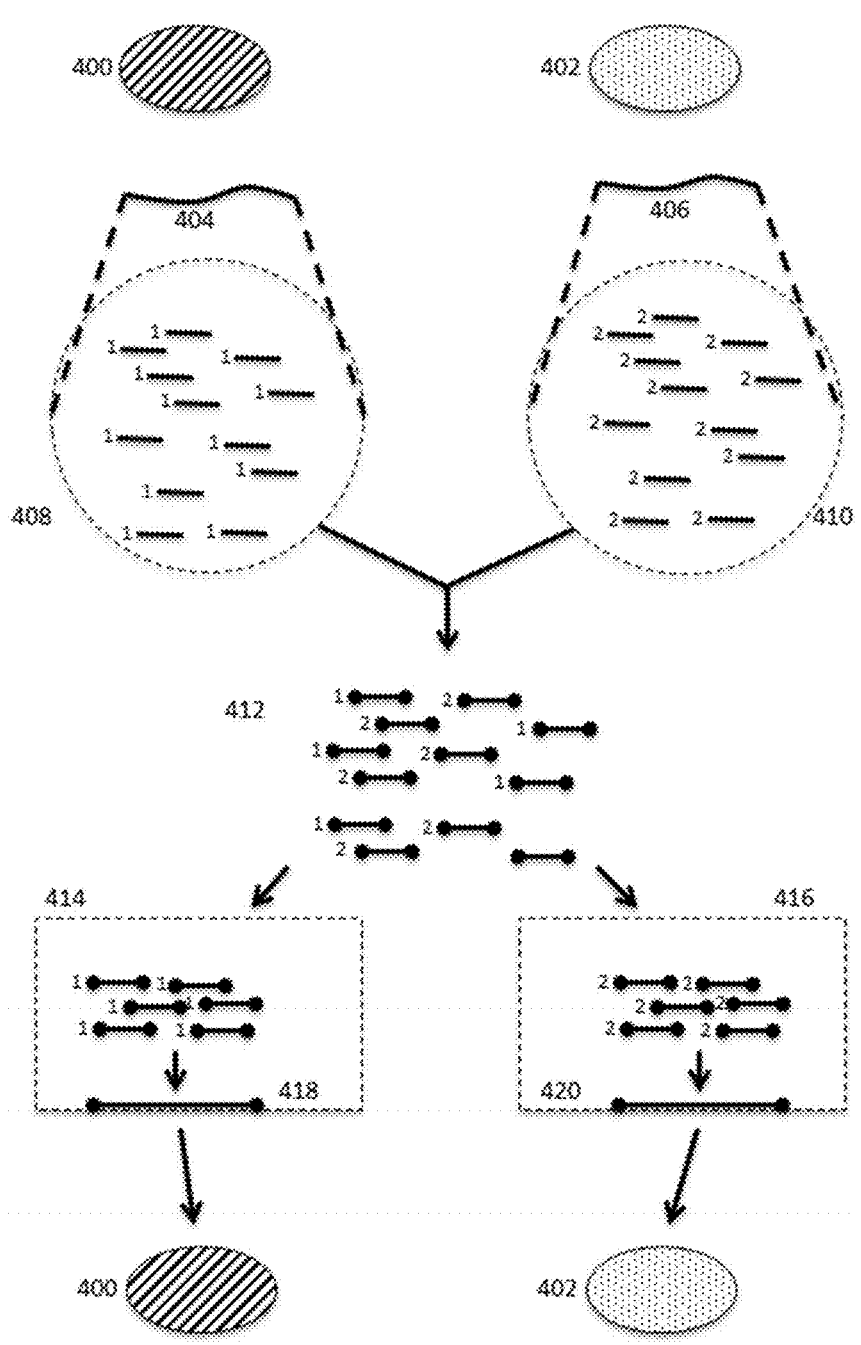
FIG. 4 provides a schematic illustration of use of barcoding of cell's nucleic acids in attributing sequence data to individual cells or groups of cells for use in their characterization.

All of the fragments from multiple different partitions may then be pooled for sequencing on high throughput sequencers as described herein, where the pooled fragments comprise a large number of fragments derived from the nucleic acids of different cells or small cell populations, but where the fragments from the nucleic acids of a given cell will share the same barcode sequence. In particular, because each fragment is coded as to its partition of origin, and consequently its single cell or small population of cells, the sequence of that fragment may be attributed back to that cell or those cells based upon the presence of the barcode, which will also aid in applying the various sequence fragments from multiple partitions to assembly of individual genomes for different cells. This is schematically illustrated in FIG. 4. As shown in one example, a first nucleic acid 404 from a first cell 400, and a second nucleic acid 406 from a second cell 402 are each partitioned along with their own sets of barcode oligonucleotides as described above. The nucleic acids may comprise a chromosome, entire genome or other large nucleic acid from the cells.

Within each partition, each cell's nucleic acids 404 and 406 is then processed to separately provide overlapping set of second fragments of the first fragment(s), e.g., second fragment sets 408 and 410. This processing also provides the second fragments with a barcode sequence that is the same for each of the second fragments derived from a particular first fragment. As shown, the barcode sequence for second fragment set 408 is denoted by "1" while the barcode sequence for fragment set 410 is denoted by "2". A diverse library of barcodes may be used to differentially barcode large numbers of different fragment sets. However, it is not necessary for every second fragment set from a different first fragment to be barcoded with different barcode sequences. In fact, in many cases, multiple different first fragments may be processed concurrently to include the same barcode sequence. Diverse barcode libraries are described in detail elsewhere herein.

The barcoded fragments, e.g., from fragment sets 408 and 410, may then be pooled for sequencing using, for example, sequence by synthesis technologies available from Illumina or Ion Torrent division of Thermo-Fisher, Inc. Once sequenced, the sequence reads 412 can be attributed to their respective fragment set, e.g., as shown in aggregated reads 414 and 416, at least in part based upon the included barcodes, and in some cases, in part based upon the sequence of the fragment itself. The attributed sequence reads for each fragment set are then assembled to provide the assembled sequence for each cell's nucleic acids, e.g., sequences 418 and 420, which in turn, may be attributed to individual cells, e.g., cells 400 and 402.

While described in terms of analyzing the genetic material present within cells, the methods and systems described herein may have much broader applicability, including the ability to characterize other aspects of individual cells or cell populations, by allowing for the allocation of reagents to individual cells, and providing for the attributable analysis or characterization of those cells in response to those reagents. These methods and systems are particularly valuable in being able to characterize cells for, e.g., research, diagnostic, pathogen identification, and many other purposes. By way of example, a wide range of different cell surface features, e.g., cell surface proteins like cluster of differentiation or CD proteins, have significant diagnostic relevance in characterization of diseases like cancer.

In one particularly useful application, the methods and systems described herein may be used to characterize cell features, such as cell surface features, e.g., proteins, receptors, etc. In particular, the methods described herein may be used to attach reporter molecules to these cell features, that when partitioned as described above, may be barcoded and analyzed, e.g., using DNA sequencing technologies, to ascertain the presence, and in some cases, relative abundance or quantity of such cell features within an individual cell or population of cells.

In a particular example, a library of potential cell binding ligands, e.g., antibodies, antibody fragments, cell surface receptor binding molecules, or the like, maybe provided associated with a first set of nucleic acid reporter molecules, e.g., where a different reporter oligonucleotide sequence is associated with a specific ligand, and therefore capable of binding to a specific cell surface feature. In some aspects, different members of the library may be characterized by the presence of a different oligonucleotide sequence label, e.g., an antibody to a first type of cell surface protein or receptor would have associated with it a first known reporter oligonucleotide sequence, while an antibody to a second receptor protein would have a different known reporter oligonucleotide sequence associated with it. Prior to co-partitioning, the cells would be incubated with the library of ligands, that may represent antibodies to a broad panel of different cell surface features, e.g., receptors, proteins, etc., and which include their associated reporter oligonucleotides. Unbound ligands are washed from the cells, and the cells are then co-partitioned along with the barcode oligonucleotides described above. As a result, the partitions will include the cell or cells, as well as the bound ligands and their known, associated reporter oligonucleotides.

Without the need for lysing the cells within the partitions, one could then subject the reporter oligonucleotides to the barcoding operations described above for cellular nucleic acids, to produce barcoded, reporter oligonucleotides, where the presence of the reporter oligonucleotides can be indicative of the presence of the particular cell surface feature, and the barcode sequence will allow the attribution of the range of different cell surface features to a given individual cell or population of cells based upon the barcode sequence that was co-partitioned with that cell or population of cells. As a result, one may generate a cell-by-cell profile of the cell surface features within a broader population of cells. This aspect of the methods and systems described herein, is described in greater detail below.

Figure 5:
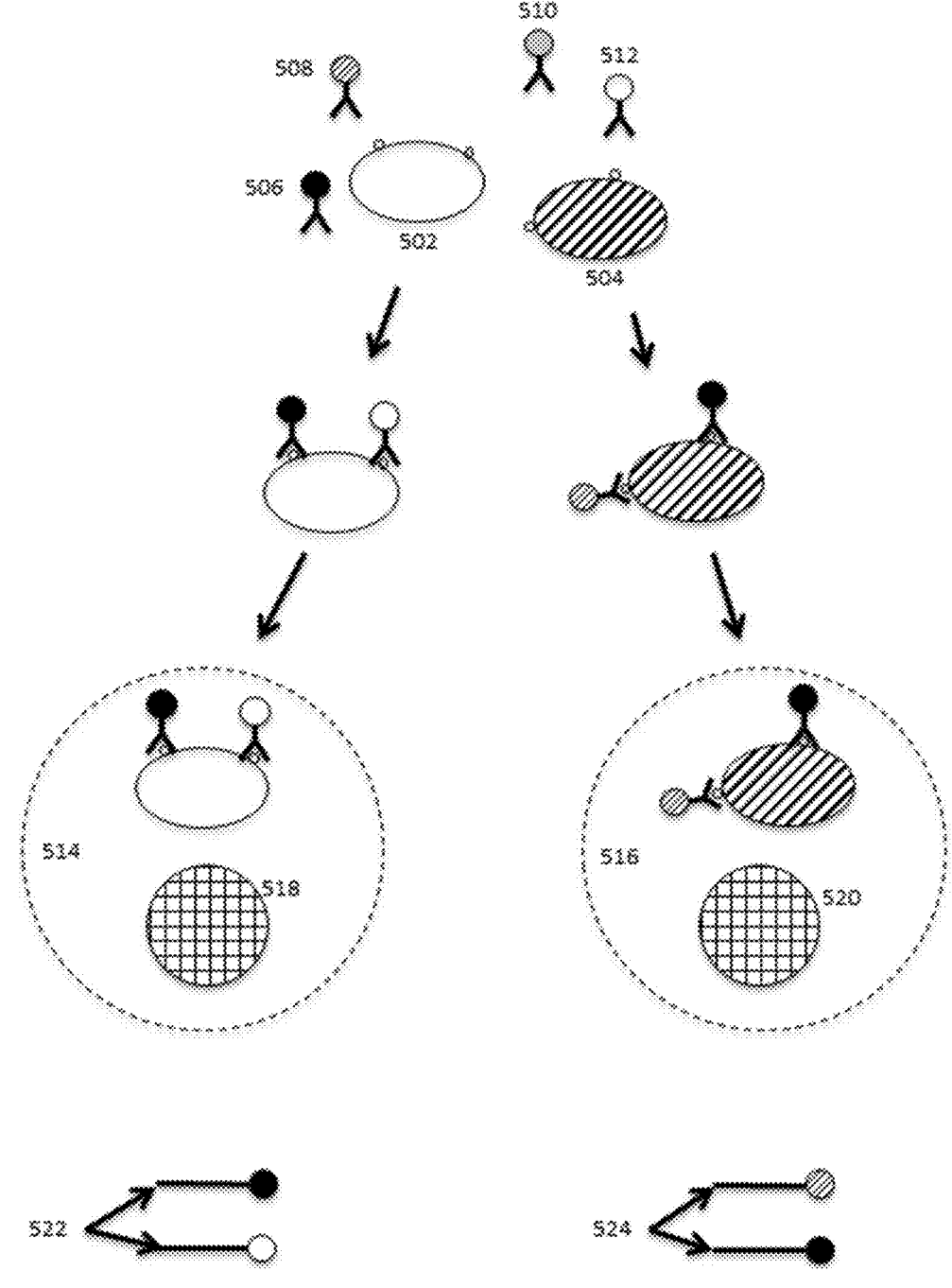
FIG. 5 provides a schematic illustrating cells associated with labeled cell-binding ligands.

This example is schematically illustrated in FIG. 5. As shown, a population of cells, represented by cells 502 and 504 are incubated with a library of cell surface associated reagents, e.g., antibodies, cell surface binding proteins, ligands or the like, where each different type of binding group includes an associated nucleic acid reporter molecule associated with it, shown as ligands and associated reporter molecules 506, 508, 510 and 512 (with the reporter molecules being indicated by the differently shaded circles). Where the cell expresses the surface features that are bound by the library, the ligands and their associated reporter molecules can become associated or coupled with the cell surface. Individual cells are then partitioned into separate partitions, e.g., droplets 514 and 516, along with their associated ligand/reporter molecules, as well as an individual barcode oligonucleotide bead as described elsewhere herein, e.g., beads 522 and 524, respectively. As with other examples described herein, the barcoded oligonucleotides are released from the beads and used to attach the barcode sequence the reporter molecules present within each partition with a barcode that is common to a given partition, but which varies widely among different partitions. For example, as shown in FIG. 5, the reporter molecules that associate with cell 502 in partition 514 are barcoded with barcode sequence 518, while the reporter molecules associated with cell 504 in partition 516 are barcoded with barcode 520. As a result, one is provided with a library of oligonucleotides that reflects the surface ligands of the cell, as reflected by the reporter molecule, but which is substantially attributable to an individual cell by virtue of a common barcode sequence, allowing a single cell level profiling of the surface characteristics of the cell. As will be appreciated, this process is not limited to cell surface receptors but may be used to identify the presence of a wide variety of specific cell structures, chemistries or other characteristics.

III. Applications of Single Cell Analysis

There are a wide variety of different applications of the single cell processing and analysis methods and systems described herein, including analysis of specific individual ells, analysis of different cell types within populations of differing cell types, analysis and characterization of large populations of cells for environmental, human health, epidemiological forensic, or any of a wide variety of different applications.

A particularly valuable application of the single cell analysis processes described herein is in the sequencing and characterization of cancer cells. In particular, conventional analytical techniques, including the ensemble sequencing processes alluded to above, are not highly adept at picking small variations in genomic make-up of cancer cells, particularly where those exist in a sea of normal tissue cells. Further, even as between tumor cells, wide variations can exist and can be masked by the ensemble approaches to sequencing (See, e.g., Patel, et al., Single-cell RNA-seq highlights intratumoral heterogeneity in primary glioblastoma, Science DOI: 10.1126/science.1254257 (Published online Jun. 12, 2014). Cancer cells may be derived from solid tumors, hematological malignancies, cell lines, or obtained as circulating tumor cells, and subjected to the partitioning processes described above. Upon analysis, one can identify individual cell sequences as deriving from a single cell or small group of cells, and distinguish those over normal tissue cell sequences. Further, as described in co-pending U.S. patent application Ser. No. 14/752,589 (US20150376700), filed Jun. 26, 2015, the full disclosures of which is hereby incorporated herein by reference in its entirety for all purposes, one may also obtain phased sequence information from each cell, allowing clearer characterization of the haplotype variants within a cancer cell. The single cell analysis approach is particularly useful for systems and methods involving low quantities of input nucleic acids, as described in co-pending U.S. patent application Ser. No. 14/752,602 (US20150376605), filed Jun. 26, 2015, the full disclosures of which is hereby incorporated herein by reference in its entirety for all purposes.

As with cancer cell analysis, the analysis and diagnosis of fetal health or abnormality through the analysis of fetal cells is a difficult task using conventional techniques. In particular, in the absence of relatively invasive procedures, such as amniocentesis obtaining fetal cell samples can employ harvesting those cells from the maternal circulation. As will be appreciated, such circulating fetal cells make up an extremely small fraction of the overall cellular population of that circulation. As a result complex analyses are performed in order to characterize what of the obtained data is likely derived from fetal cells as opposed to maternal cells. By employing the single cell characterization methods and systems described herein, however, one can attribute genetic make up to individual cells, and categorize those cells as maternal or fetal based upon their respective genetic make-up. Further, the genetic sequence of fetal cells may be used to identify any of a number of genetic disorders, including, e.g., aneuploidy such as Down syndrome, Edwards syndrome, and Patau syndrome.

The ability to characterize individual cells from larger diverse populations of cells is also of significant value in both environmental testing as well as in forensic analysis, where samples may, by their nature, be made up of diverse populations of cells and other material that "contaminate" the sample, relative to the cells for which the sample is being tested, e.g., environmental indicator organisms, toxic organisms, and the like for, e.g., environmental and food safety testing, victim and/or perpetrator cells in forensic analysis for sexual assault, and other violent crimes, and the like.

Additional useful applications of the above described single cell sequencing and characterization processes are in the field of neuroscience research and diagnosis. In particular, neural cells can include long interspersed nuclear elements (LINEs), or 'jumping' genes that can move around the genome, which cause each neuron to differ from its neighbor cells. Research has shown that the number of LINEs in human brain exceeds that of other tissues, e.g., heart and liver tissue, with between 80 and 300 unique insertions (See, e.g., Coufal, N. G. et al. Nature 460, 1127-1131 (2009)). These differences have been postulated as being related to a person's susceptibility to neuro-logical disorders (see, e.g., Muotri, A. R. et al. Nature 468, 443-446 (2010)), or provide the brain with a diversity with which to respond to challenges. As such, the methods described herein may be used in the sequencing and characterization of individual neural cells.

The single cell analysis methods described herein are also useful in the analysis of gene expression, as noted above, both in terms of identification of RNA transcripts and their quantitation. In particular, using the single cell level analysis methods described herein, one can isolate and analyze the RNA transcripts present in individual cells, populations of cells, or subsets of populations of cells. In particular, in some cases, the barcode oligonucleotides may be configured to prime, replicate and consequently yield barcoded fragments of RNA from individual cells. For example, in some cases, the barcode oligonucleotides may include mRNA specific priming sequences, e.g., poly-dT primer segments that allow priming and replication of mRNA in a reverse transcription reaction or other targeted priming sequences (e.g., gene-specific primers). Alternatively or additionally, random RNA priming may be carried out using random N-mer primer segments of the barcode oligonucleotides.

Figure 6:
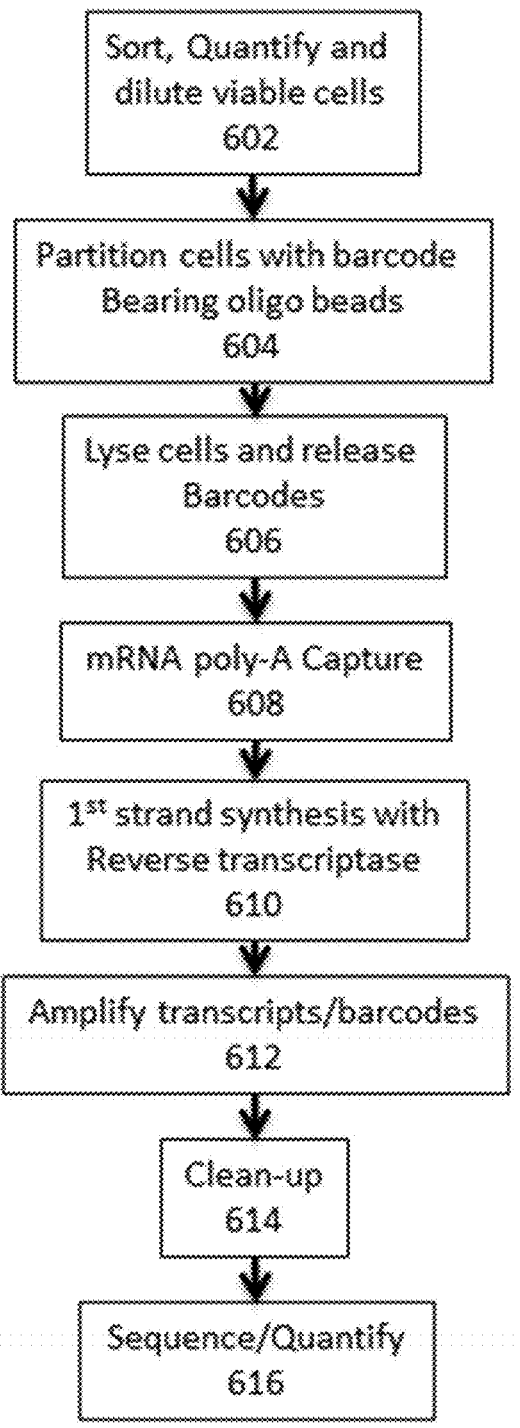
FIG. 6 provides a schematic illustration of an example workflow for performing RNA analysis using the methods described herein.

FIG. 6 provides a schematic of one example method for RNA expression analysis in individual cells using the methods described herein. As shown, at operation 602 a cell containing sample is sorted for viable cells, which are quantified and diluted for subsequent partitioning. At operation 604, the individual cells separately co-partitioned with gel beads bearing the barcoding oligonucleotides as described herein. The cells are lysed and the barcoded oligonucleotides released into the partitions at operation 606, where they interact with and hybridize to the mRNA at operation 608, e.g., by virtue of a poly-dT primer sequence, which is complementary to the poly-A tail of the mRNA. Using the poly-dT barcode oligonucleotide as a priming sequence, a reverse transcription reaction is carried out using the engineered reverse transcriptase enzymes described herein at operation 610 to synthesize a cDNA transcript of the mRNA that includes the barcode sequence. The barcoded cDNA transcripts are then subjected to additional amplification at operation 612, e.g., using a PCR process, purification at operation 614, before they are placed on a nucleic acid sequencing system for determination of the cDNA sequence and its associated barcode sequence(s). In some cases, as shown, operations 602 through 608 can occur while the reagents remain in their original droplet or partition, while operations 612 through 616 can occur in bulk (e.g., outside of the partition). In the case where a partition is a droplet in an emulsion, the emulsion can be broken and the contents of the droplet pooled in order to complete operations 612 through 616. In some cases, barcode oligonucleotides may be digested with exonucleases after the emulsion is broken. Exonuclease activity can be inhibited by ethylenediaminetetraacetic acid (EDTA) following primer digestion. In some cases, operation 610 may be performed either within the partitions based upon co-partitioning of the reverse transcription mixture, e.g., reverse transcriptase and associated reagents, or it may be performed in bulk.

As noted elsewhere herein, the structure of the barcode oligonucleotides may include a number of sequence elements in addition to the oligonucleotide barcode sequence. One example of a barcode oligonucleotide for use in RNA analysis as described above is shown in FIG. 7. As shown, the overall oligonucleotide 702 is coupled to a bead 704 by a releasable linkage 706, such as a disulfide linker. The oligonucleotide may include functional sequences that are used in subsequent processing, such as functional sequence 708, which may include one or more of a sequencer specific flow cell attachment sequence, e.g., a P5 sequence for Illumina sequencing systems, as well as sequencing primer sequences, e.g., a R1 primer for Illumina sequencing systems. A barcode sequence 710 is included within the structure for use in barcoding the sample RNA. An mRNA specific priming sequence, such as poly-dT sequence 712 is also included in the oligonucleotide structure. An anchoring sequence segment 714 may be included to ensure that the poly-dT sequence hybridizes at the sequence end of the mRNA. This anchoring sequence can include a random short sequence of nucleotides, e.g., 1-mer, 2-mer, 3-mer or longer sequence, which will ensure that the poly-dT segment is more likely to hybridize at the sequence end of the poly-A tail of the mRNA. An additional sequence segment 716 may be provided within the oligonucleotide sequence. In some cases, this additional sequence provides a unique molecular sequence segment, e.g., as a random sequence (e.g., such as a random N-mer sequence) that varies across individual oligonucleotides coupled to a single bead, whereas barcode sequence 710 can be constant among oligonucleotides tethered to an individual bead. This unique sequence serves to provide a unique identifier of the starting mRNA molecule that was captured, in order to allow quantitation of the number of original expressed RNA. As will be appreciated, although shown as a single oligonucleotide tethered to the surface of a bead, individual bead can include tens to hundreds of thousands or even millions of individual oligonucleotide molecules, where, as noted, the barcode segment can be constant or relatively constant for a given bead, but where the variable or unique sequence segment will vary across an individual bead. This unique molecular sequence segment may include from 5 to about 8 or more nucleotides within the sequence of the oligonucleotides. In some cases, the unique molecular sequence segment can be 2, 3, 4, 5, 6, 7, 8, 9, 10, 11, 12, 13, 14, 15, 16, 17, 18, 19 or 20 nucleotides in length or longer. In some cases, the unique molecular sequence segment can be at least 2, 3, 4, 5, 6, 7, 8, 9, 10, 11, 12, 13, 14, 15, 16, 17, 18, 19 or 20 nucleotides in length or longer. In some cases, the unique molecular sequence segment can be at most 2, 3, 4, 5, 6, 7, 8, 9, 10, 11, 12, 13, 14, 15, 16, 17, 18, 19 or 20 nucleotides in length or shorter.

Figure 7:
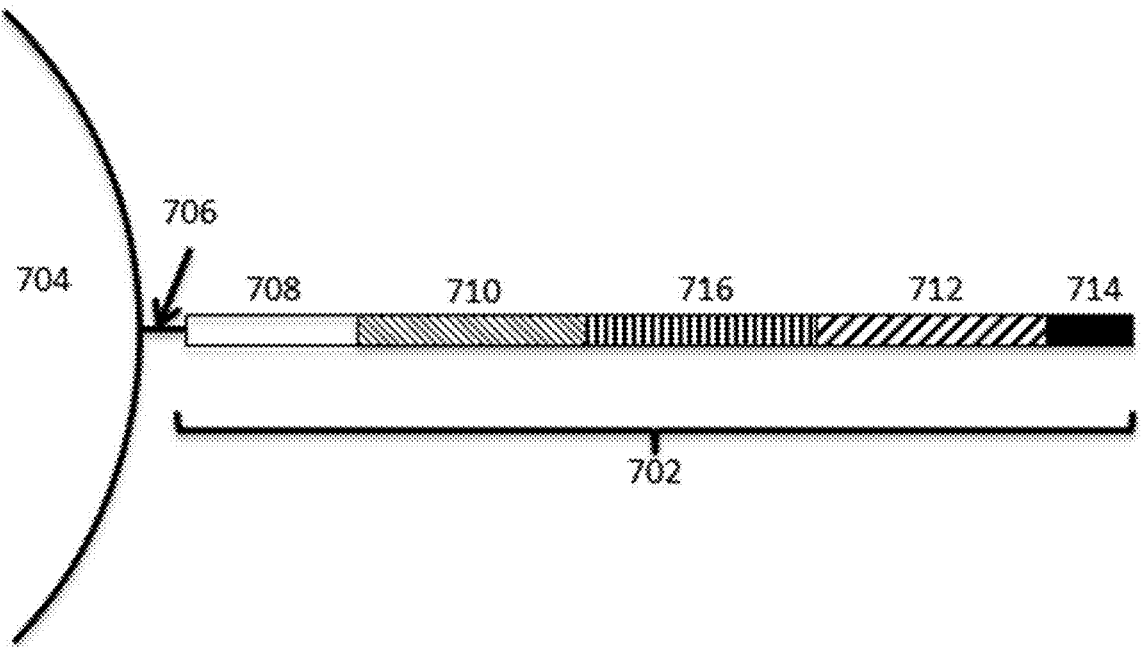
FIG. 7 provides a schematic illustration of an example barcoded oligonucleotide structure for use in analysis of ribonucleic (RNA) using the methods described herein.

In operation, and with reference to FIG. 6 and FIG. 7, a cell is co-partitioned along with a barcode bearing bead and lysed while the barcoded oligonucleotides are released from the bead. The poly-dT portion of the released barcode oligonucleotide then hybridizes to the poly-A tail of the mRNA. The poly-dT segment then primes the reverse transcription of the mRNA to produce a cDNA transcript of the mRNA, but which includes each of the sequence segments 708-716 of the barcode oligonucleotide. Again, because the oligonucleotide 702 includes an anchoring sequence 714, it will more likely hybridize to and prime reverse transcription at the sequence end of the poly-A tail of the mRNA. Within any given partition, all of the cDNA transcripts of the individual mRNA molecules will include a common barcode sequence segment 710. However, by including the unique random N-mer sequence, the transcripts made from different mRNA molecules within a given partition will vary at this unique sequence. This provides a quantitation feature that can be identifiable even following any subsequent amplification of the contents of a given partition, e.g., the number of unique segments associated with a common barcode can be indicative of the quantity of mRNA originating from a single partition, and thus, a single cell. As noted above, the transcripts are then amplified, cleaned up and sequenced to identify the sequence of the cDNA transcript of the mRNA, as well as to sequence the barcode segment and the unique sequence segment.

As noted elsewhere herein, while a poly-dT primer sequence is described, other targeted or random priming sequences may also be used in priming the reverse transcription reaction. Likewise, although described as releasing the barcoded oligonucleotides into the partition along with the contents of the lysed cells, it will be appreciated that in some cases, the gel bead bound oligonucleotides may be used to hybridize ad capture the mRNA on the solid phase of the gel beads, in order to facilitate the separation of the RNA from other cell contents.

Figure 9A:
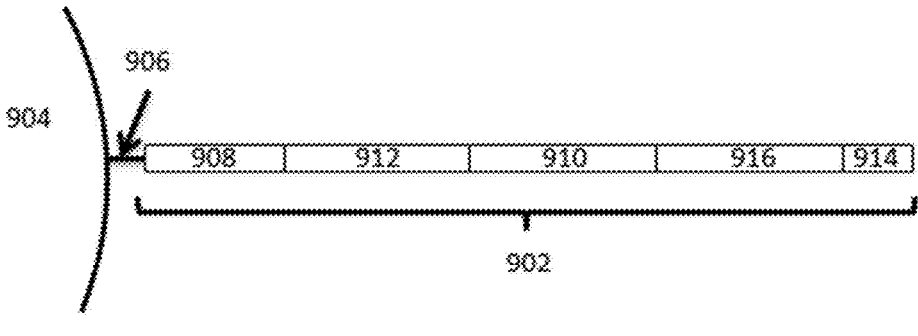
FIGS. 9A-9E disclose AAAAAAAAAAAAAAAA as SEQ ID NO:10.
Figure 9A:
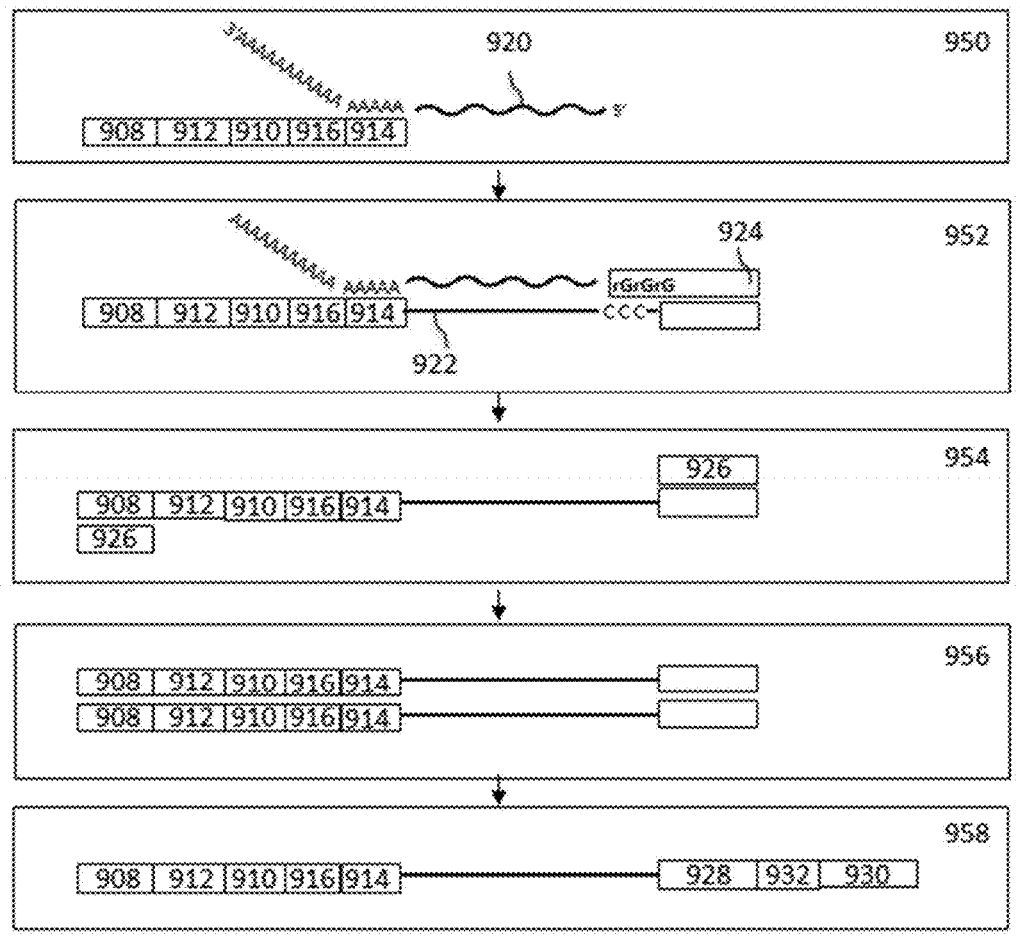

An additional example of a barcode oligonucleotide for use in RNA analysis, including messenger RNA (mRNA, including mRNA obtained from a cell) analysis, is shown in FIG. 9A. As shown, the overall oligonucleotide 902 can be coupled to a bead 904 by a releasable linkage 906, such as a disulfide linker. The oligonucleotide may include functional sequences that are used in subsequent processing, such as functional sequence 908, which may include a sequencer specific flow cell attachment sequence, e.g., a P5 sequence for Illumina sequencing systems, as well as functional sequence 910, which may include sequencing primer sequences, e.g., a R1 primer binding site for Illumina sequencing systems. A barcode sequence 912 is included within the structure for use in barcoding the sample RNA. An RNA specific (e.g., mRNA specific) priming sequence, such as poly-dT sequence 914 is also included in the oligonucleotide structure. An anchoring sequence segment (not shown) may be included to ensure that the poly-dT sequence hybridizes at the sequence end of the mRNA. An additional sequence segment 916 may be provided within the oligonucleotide sequence. This additional sequence can provide a unique molecular sequence segment, e.g., as a random N-mer sequence that varies across individual oligonucleotides coupled to a single bead, whereas barcode sequence 912 can be constant among oligonucleotides tethered to an individual bead. As described elsewhere herein, this unique sequence can serve to provide a unique identifier of the starting mRNA molecule that was captured, in order to allow quantitation of the number of original expressed RNA, e.g., mRNA counting. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

In an example method of cellular RNA (e.g., mRNA) analysis and in reference to FIG. 9A, a cell is co-partitioned along with a barcode bearing bead, switch oligo 924, and other reagents such as reverse transcriptase, a reducing agent and dNTPs into a partition (e.g., a droplet in an emulsion). In operation 950, the cell is lysed while the barcoded oligonucleotides 902 are released from the bead (e.g., via the action of the reducing agent) and the poly-dT segment 914 of the released barcode oligonucleotide then hybridizes to the poly-A tail of mRNA 920 that is released from the cell. Next, in operation 952 the poly-dT segment 914 is extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the additional bases added to the cDNA transcript and facilitate template switching. A sequence complementary to the switch oligo sequence can then be incorporated into the cDNA transcript 922 via extension of the cDNA transcript 922 using the switch oligo 924 as a template. Within any given partition, all of the cDNA transcripts of the individual mRNA molecules will include a common barcode sequence segment 912. However, by including the unique random N-mer sequence 916, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. Following operation 952, the cDNA transcript 922 is then amplified with primers 926 (e.g., PCR primers) in operation 954. Next, the amplified product is then purified (e.g., via solid phase reversible immobilization (SPRI)) in operation 956. At operation 958, the amplified product is then sheared, ligated to additional functional sequences, and further amplified (e.g., via PCR). The functional sequences may include a sequencer specific flow cell attachment sequence 930, e.g., a P7 sequence for Illumina sequencing systems, as well as functional sequence 928, which may include a sequencing primer binding site, e.g., for a R2 primer for Illumina sequencing systems, as well as functional sequence 932, which may include a sample index, e.g., an i7 sample index sequence for Illumina sequencing systems. In some cases, operations 950 and 952 can occur in the partition, while operations 954, 956 and 958 can occur in bulk solution (e.g., in a pooled mixture outside of the partition). In the case where a partition is a droplet in an emulsion, the emulsion can be broken and the contents of the droplet pooled in order to complete operations 954, 956 and 958. In some cases, operation 954 may be completed in the partition. In some cases, barcode oligonucleotides may be digested with exonucleases after the emulsion is broken. Exonuclease activity can be inhibited by ethylenediaminetetraacetic acid (EDTA) following primer digestion. Although described in terms of specific sequence references used for certain sequencing systems, e.g., Illumina systems, it will be understood that the reference to these sequences is for illustration purposes only, and the methods described herein may be configured for use with other sequencing systems incorporating specific priming, attachment, index, and other operational sequences used in those systems, e.g., systems available from Ion Torrent, Oxford Nanopore, Genia, Pacific Biosciences, Complete Genomics, and the like.

In an alternative example of a barcode oligonucleotide for use in RNA (e.g., cellular RNA) analysis as shown in FIG. 9A, functional sequence 908 may be a P7 sequence and functional sequence 910 may be a R2 primer binding site. Moreover, the functional sequence 930 may be a P5 sequence, functional sequence 928 may be a R1 primer binding site, and functional sequence 932 may be an i5 sample index sequence for Illumina sequencing systems. The configuration of the constructs generated by such a barcode oligonucleotide can help minimize (or avoid) sequencing of the poly-dT sequence during sequencing.

Figure 9B:
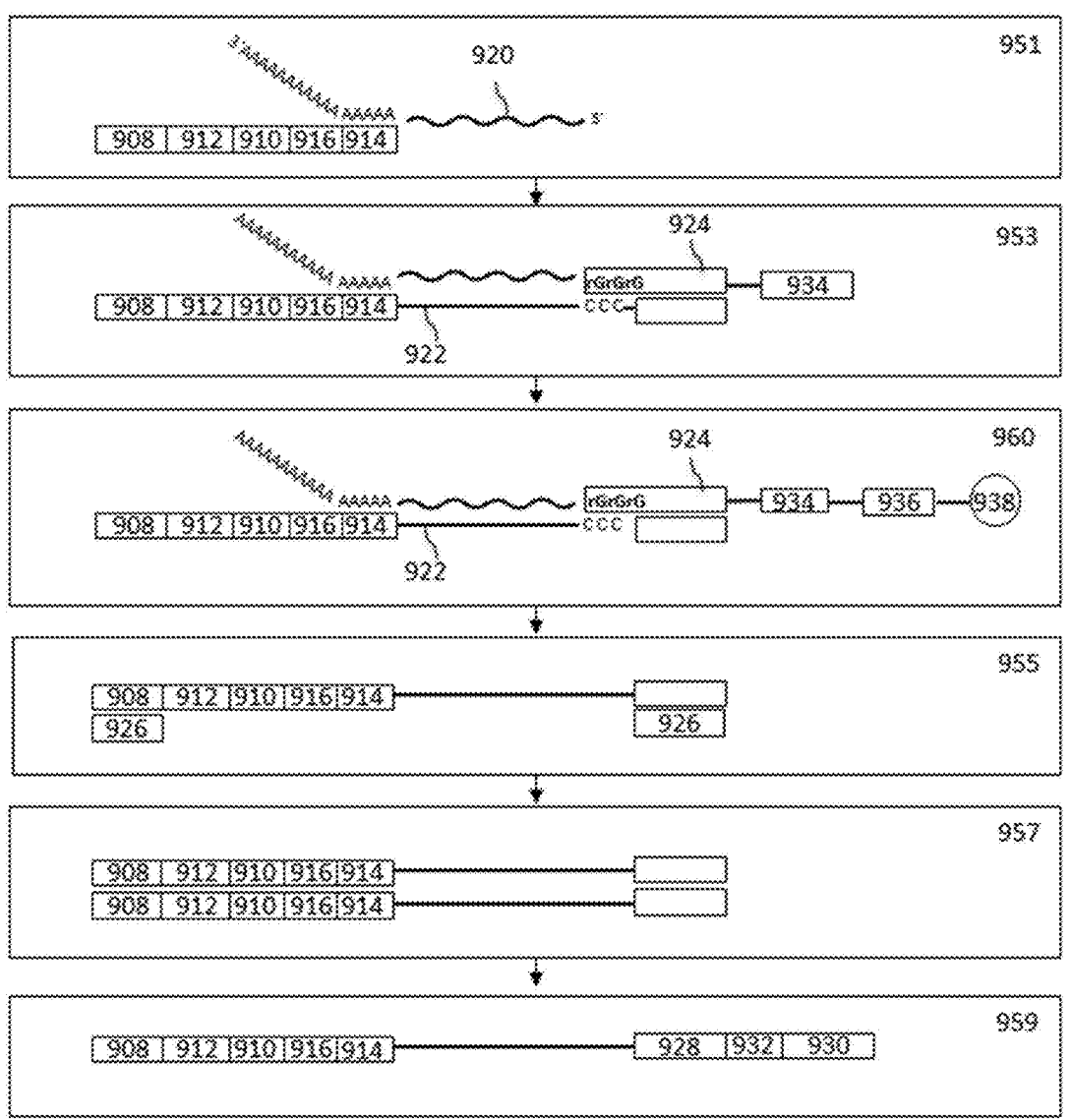

Shown in FIG. 9B is another example method for RNA analysis, including cellular mRNA analysis. In this method, the switch oligo 924 is co-partitioned with the individual cell and barcoded bead along with reagents such as reverse transcriptase, a reducing agent and dNTPs into a partition (e.g., a droplet in an emulsion). The switch oligo 924 may be labeled with an additional tag 934, e.g. biotin. In operation 951, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-dT segment 914 of the released barcode oligonucleotide hybridizes to the poly-A tail of mRNA 920 that is released from the cell. In operation 953, the poly-dT segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. Next, an isolation operation 960 can be used to isolate the cDNA transcript 922 from the reagents and oligonucleotides in the partition. The additional tag 934, e.g. biotin, can be contacted with an interacting tag 936, e.g., streptavidin, which may be attached to a magnetic bead 938. At operation 960 the cDNA can be isolated with a pull-down operation (e.g., via magnetic separation, centrifugation) before amplification (e.g., via PCR) in operation 955, followed by purification (e.g., via solid phase reversible immobilization (SPRI)) in operation 957 and further processing (shearing, ligation of sequences 928, 932 and 930 and subsequent amplification (e.g., via PCR)) in operation 959. In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, as shown, operations 951 and 953 can occur in the partition, while operations 960, 955, 957 and 959 can occur in bulk solution (e.g., in a pooled mixture outside of the partition). In the case where a partition is a droplet in an emulsion, the emulsion can be broken and the contents of the droplet pooled in order to complete operation 960. The operations 955, 957, and 959 can then be carried out following operation 960 after the transcripts are pooled for processing.

Figure 9C:
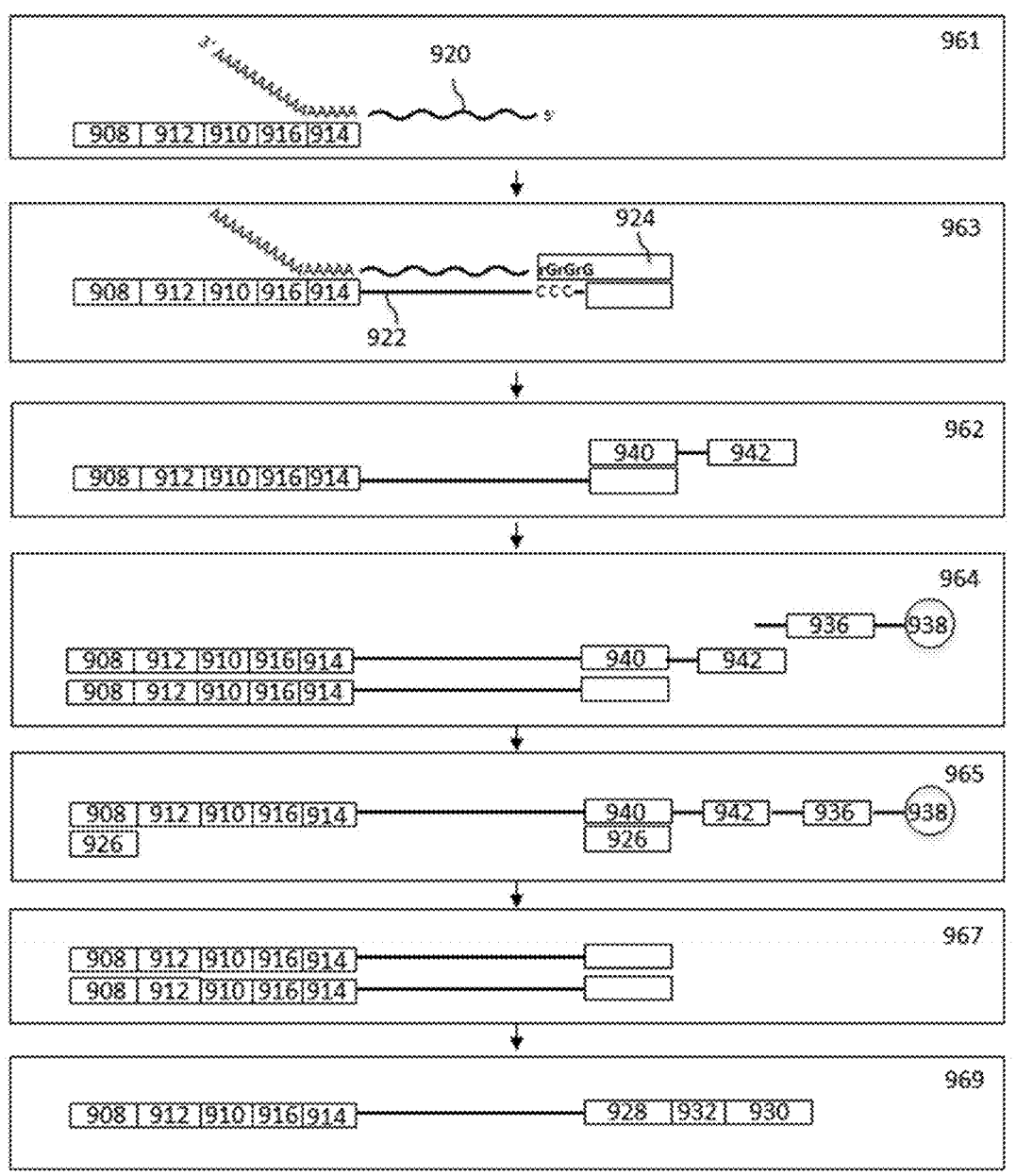

Shown in FIG. 9C is another example method for RNA analysis, including cellular mRNA analysis. In this method, the switch oligo 924 is co-partitioned with the individual cell and barcoded bead along with reagents such as reverse transcriptase, a reducing agent and dNTPs in a partition (e.g., a droplet in an emulsion). In operation 961, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-dT segment 914 of the released barcode oligonucleotide then hybridizes to the poly-A tail of mRNA 920 that is released from the cell. Next, in operation 963 the poly-dT segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. Following operation 961 and operation 963, mRNA 920 and cDNA transcript 922 are denatured in operation 962. At operation 964, a second strand is extended from a primer 940 having an additional tag 942, e.g. biotin, and hybridized to the cDNA transcript 922. Also in operation 964, the biotin labeled second strand can be contacted with an interacting tag 936, e.g. streptavidin, which may be attached to a magnetic bead 938. The cDNA can be isolated with a pull-down operation (e.g., via magnetic separation, centrifugation) before amplification (e.g., via polymerase chain reaction (PCR)) in operation 965, followed by purification (e.g., via solid phase reversible immobilization (SPRI)) in operation 967 and further processing (shearing, ligation of sequences 928, 932 and 930 and subsequent amplification (e.g., via PCR)) in operation 969. In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, operations 961 and 963 can occur in the partition, while operations 962, 964, 965, 967, and 969 can occur in bulk (e.g., outside the partition). In the case where a partition is a droplet in an emulsion, the emulsion can be broken and the contents of the droplet pooled in order to complete operations 962, 964, 965, 967 and 969.

Figure 9D:
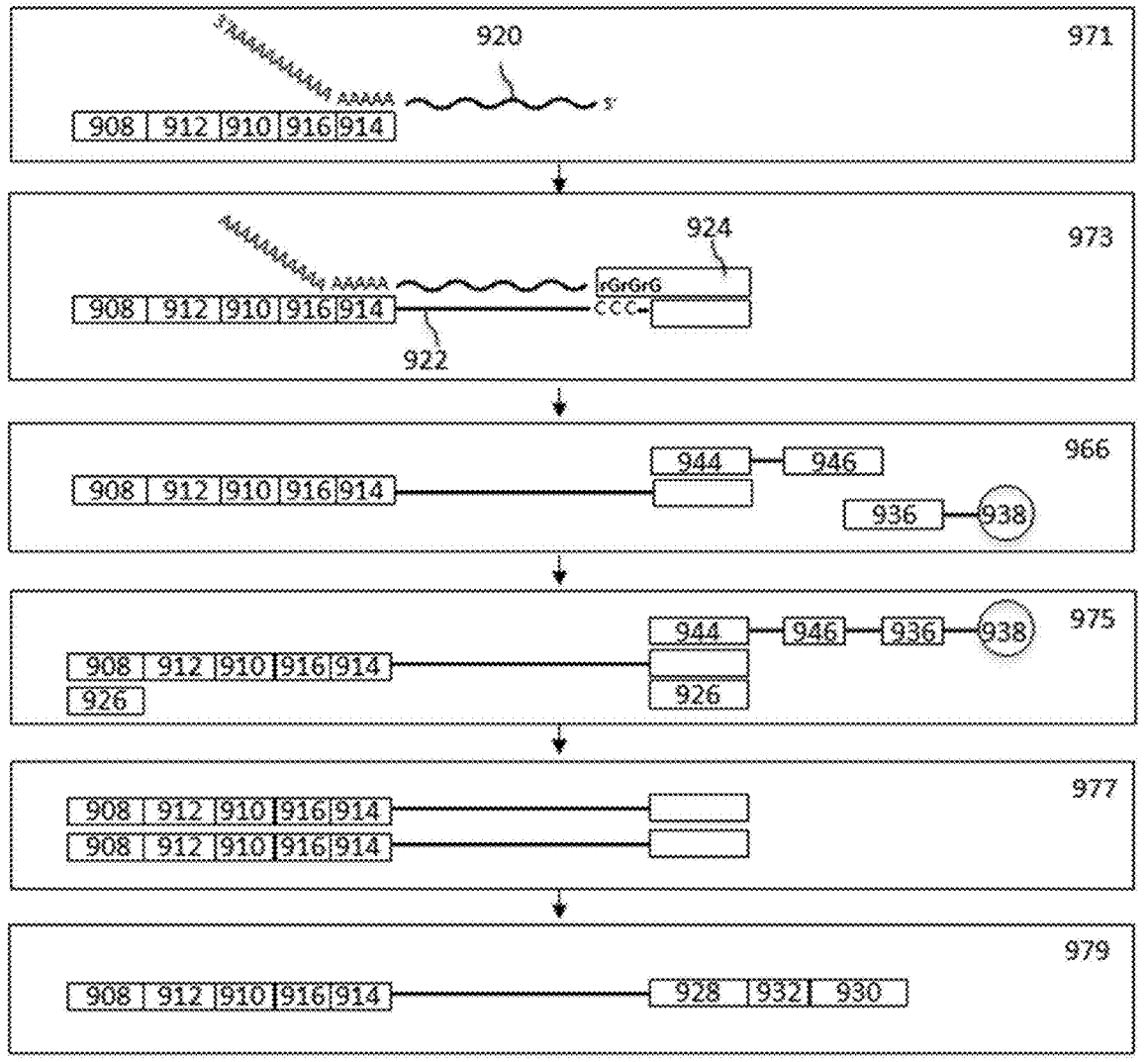

Shown in FIG. 9D is another example method for RNA analysis, including cellular mRNA analysis. In this method, the switch oligo 924 is co-partitioned with the individual cell and barcoded bead along with reagents such as reverse transcriptase, a reducing agent and dNTPs. In operation 971, the cell is lysed while the barcoded oligonucleotides 902 (e.g., as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next the poly-dT segment 914 of the released barcode oligonucleotide then hybridizes to the poly-A tail of mRNA 920 that is released from the cell. Next in operation 973, the poly-dT segment 914 is then extended in a reverse transcription reaction using the mRNA as a template to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 924 may then hybridize with the cDNA transcript and facilitate template switching. A sequence complementary to the switch oligo sequence can then be incorporated into the cDNA transcript 922 via extension of the cDNA transcript 922 using the switch oligo 924 as a template. In operation 966, the mRNA 920, cDNA transcript 922 and switch oligo 924 can be denatured, and the cDNA transcript 922 can be hybridized with a capture oligonucleotide 944 labeled with an additional tag 946, e.g. biotin. In this operation, the biotin-labeled capture oligonucleotide 944, which is hybridized to the cDNA transcript, can be contacted with an interacting tag 936, e.g. streptavidin, which may be attached to a magnetic bead 938. Following separation from other species (e.g., excess barcoded oligonucleotides) using a pull-down operation (e.g., via magnetic separation, centrifugation), the cDNA transcript can be amplified (e.g., via PCR) with primers 926 at operation 975, followed by purification (e.g., via solid phase reversible immobilization (SPRI)) in operation 977 and further processing (shearing, ligation of sequences 928, 932 and 930 and subsequent amplification (e.g., via PCR)) in operation 979. In some cases where sequence 908 is a P7 sequence and sequence 910 is a R2 primer binding site, sequence 930 is a P5 sequence and sequence 928 is a R1 primer binding site and sequence 932 is an i5 sample index sequence. In other cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, operations 971 and 973 can occur in the partition, while operations 966, 975, 977 (purification), and 979 can occur in bulk (e.g., outside the partition). In the case where a partition is a droplet in an emulsion, the emulsion can be broken and the contents of the droplet pooled in order to complete operations 966, 975, 977 and 979.

Figure 9E:
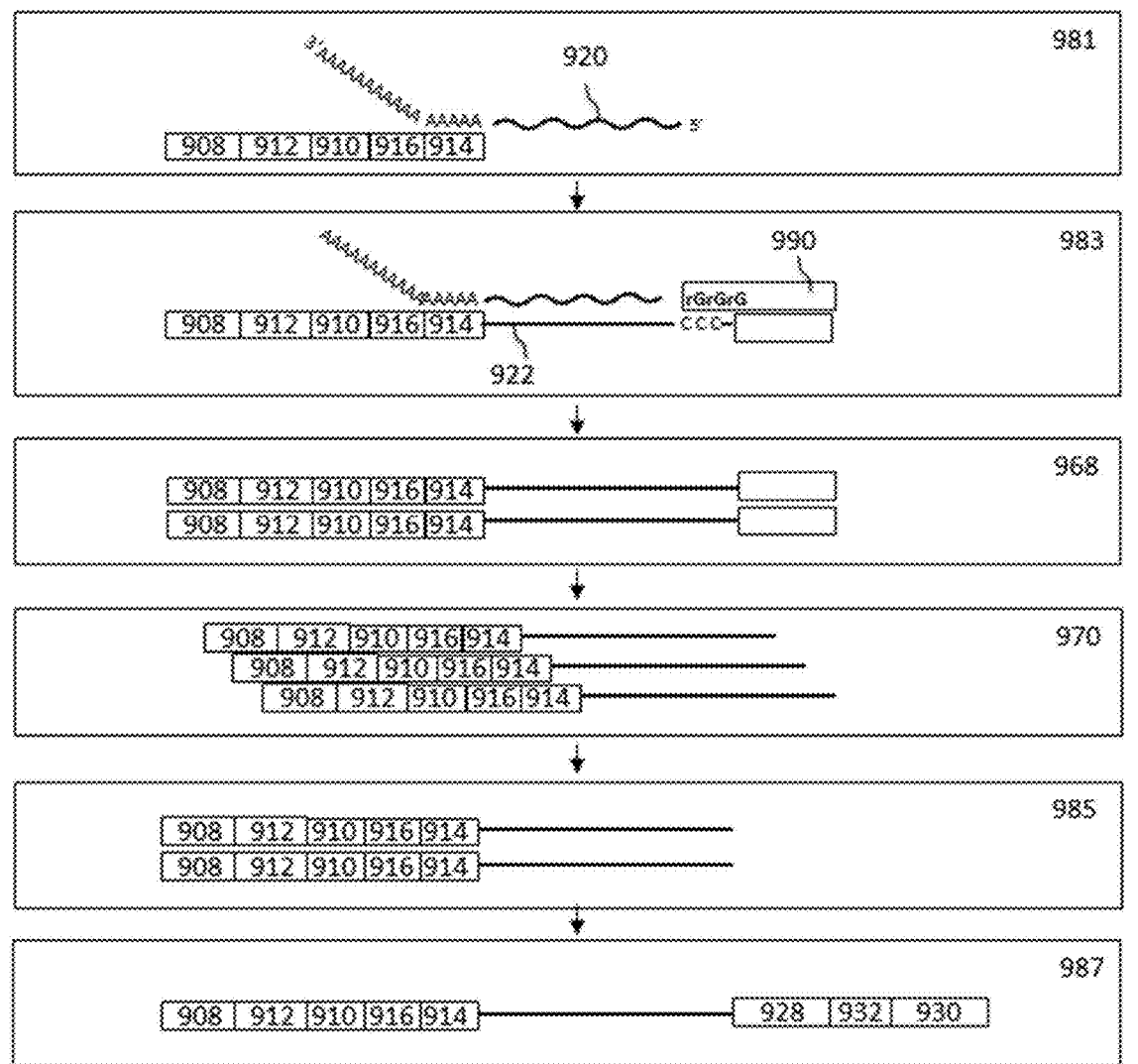

Shown in FIG. 9E is another example method for RNA analysis, including cellular RNA analysis. In this method, an individual cell is co-partitioned along with a barcode bearing bead, a switch oligo 990, and other reagents such as reverse transcriptase, a reducing agent and dNTPs into a partition (e.g., a droplet in an emulsion). In operation 981, the cell is lysed while the barcoded oligonucleotides (e.g., 902 as shown in FIG. 9A) are released from the bead (e.g., via the action of the reducing agent). In some cases, sequence 908 is a P7 sequence and sequence 910 is a R2 primer binding site. In other cases, sequence 908 is a P5 sequence and sequence 910 is a R1 primer binding site. Next, the poly-dT segment of the released barcode oligonucleotide then hybridizes to the poly-A tail of mRNA 920 released from the cell. Next at operation 983, the poly-dT segment is then extended in a reverse transcription reaction to produce a cDNA transcript 922 complementary to the mRNA and also includes each of the sequence segments 908, 912, 910, 916 and 914 of the barcode oligonucleotide. Terminal transferase activity of the reverse transcriptase can add additional bases to the cDNA transcript (e.g., polyC). The switch oligo 990 may then hybridize with the cDNA transcript and facilitate template switching. A sequence complementary to the switch oligo sequence and including a T7 promoter sequence, can be incorporated into the cDNA transcript 922. At operation 968, a second strand is synthesized and at operation 970 the T7 promoter sequence can be used by T7 polymerase to produce RNA transcripts in in vitro transcription. At operation 985 the RNA transcripts can be purified (e.g., via solid phase reversible immobilization (SPRI)), reverse transcribed to form DNA transcripts, and a second strand can be synthesized for each of the DNA transcripts. In some cases, prior to purification, the RNA transcripts can be contacted with a DNase (e.g., DNAase I) to break down residual DNA. At operation 987 the DNA transcripts are then fragmented and ligated to additional functional sequences, such as sequences 928, 932 and 930 and, in some cases, further amplified (e.g., via PCR). In some cases where sequence 908 is a P7 sequence and sequence 910 is a R2 primer binding site, sequence 930 is a P5 sequence and sequence 928 is a R1 primer binding site and sequence 932 is an i5 sample index sequence. In some cases where sequence 908 is a P5 sequence and sequence 910 is a R1 primer binding site, sequence 930 is a P7 sequence and sequence 928 is a R2 primer binding site and sequence 932 is an i7 sample index sequence. In some cases, prior to removing a portion of the DNA transcripts, the DNA transcripts can be contacted with an RNase to break down residual RNA. In some cases, operations 981 and 983 can occur in the partition, while operations 968, 970, 985 and 987 can occur in bulk (e.g., outside the partition). In the case where a partition is a droplet in an emulsion, the emulsion can be broken and the contents of the droplet pooled in order to complete operations 968, 970, 985 and 987.

Another example of a barcode oligonucleotide for use in RNA analysis, including messenger RNA (mRNA, including mRNA obtained from a cell) analysis is shown in FIG.

10. As shown, the overall oligonucleotide 1002 is coupled to a bead 1004 by a releasable linkage 1006, such as a disulfide linker. The oligonucleotide may include functional sequences that are used in subsequent processing, such as functional sequence 1008, which may include a sequencer specific flow cell attachment sequence, e.g., a P7 sequence, as well as functional sequence 1010, which may include sequencing primer sequences, e.g., a R2 primer binding site. A barcode sequence 1012 is included within the structure for use in barcoding the sample RNA. An RNA specific (e.g., mRNA specific) priming sequence, such as poly-dT sequence 1014 may be included in the oligonucleotide structure. An anchoring sequence segment (not shown) may be included to ensure that the poly-dT sequence hybridizes at the sequence end of the mRNA. An additional sequence segment 1016 may be provided within the oligonucleotide sequence. This additional sequence can provide a unique molecular sequence segment, as described elsewhere herein. An additional functional sequence 1020 may be included for in vitro transcription, e.g., a T7 RNA polymerase promoter sequence. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

Figure 10:
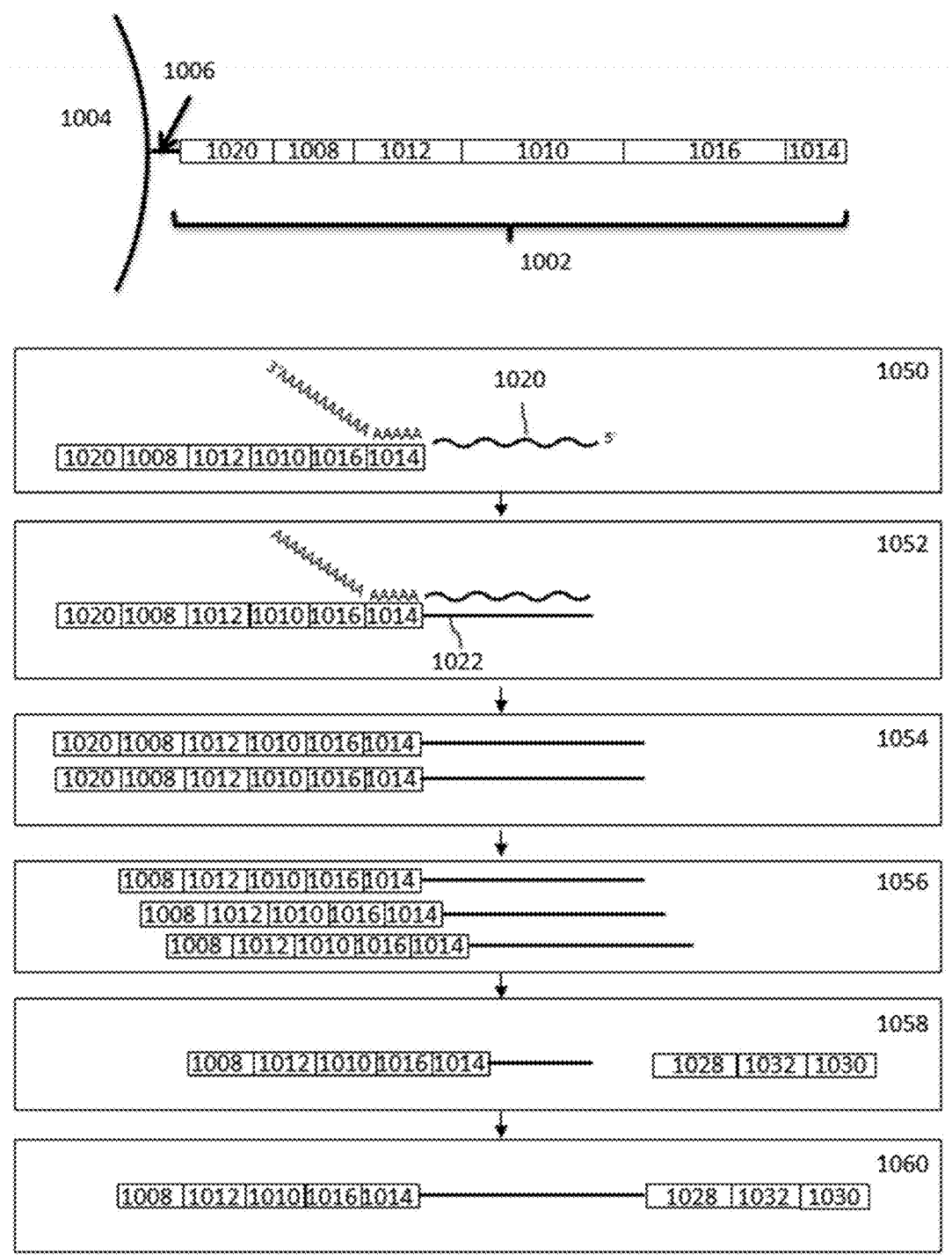
FIG. 10 provides schematic illustration of example barcoded oligonucleotide structure for use in example analysis of RNA and use of a sequence for in vitro transcription.

In an example method of cellular RNA analysis and in reference to FIG. 10, a cell is co-partitioned along with a barcode bearing bead, and other reagents such as reverse transcriptase, reducing agent and dNTPs into a partition (e.g., a droplet in an emulsion). In operation 1050, the cell is lysed while the barcoded oligonucleotides 1002 are released (e.g., via the action of the reducing agent) from the bead, and the poly-dT segment 1014 of the released barcode oligonucleotide then hybridizes to the poly-A tail of mRNA 1020. Next at operation 1052, the poly-dT segment is then extended in a reverse transcription reaction using the mRNA as template to produce a cDNA transcript 1022 of the mRNA and also includes each of the sequence segments 1020, 1008, 1012, 1010, 1016, and 1014 of the barcode oligonucleotide. Within any given partition, all of the cDNA transcripts of the individual mRNA molecules will include a common barcode sequence segment 1012. However, by including the unique random N-mer sequence, the transcripts made from different mRNA molecules within a given partition will vary at this unique sequence. As described elsewhere herein, this provides a quantitation feature that can be identifiable even following any subsequent amplification of the contents of a given partition, e.g., the number of unique segments associated with a common barcode can be indicative of the quantity of mRNA originating from a single partition, and thus, a single cell. At operation 1054 a second strand is synthesized and at operation 1056 the T7 promoter sequence can be used by T7 polymerase to produce RNA transcripts in in vitro transcription. At operation 1058 the transcripts are fragmented (e.g., sheared), ligated to additional functional sequences, and reverse transcribed. The functional sequences may include a sequencer specific flow cell attachment sequence 1030, e.g., a P5 sequence, as well as functional sequence 1028, which may include sequencing primers, e.g., a R1 primer binding sequence, as well as functional sequence 1032, which may include a sample index, e.g., an i5 sample index sequence. At operation 1060 the RNA transcripts can be reverse transcribed to DNA, the DNA amplified (e.g., via PCR), and sequenced to identify the sequence of the cDNA transcript of the mRNA, as well as to sequence the barcode segment and the unique sequence segment. In some cases, operations 1050 and 1052 can occur in the partition, while operations 1054, 1056, 1058 and 1060 can occur in bulk (e.g., outside the partition). In the case where a partition is a droplet in an emulsion, the emulsion can be broken and the contents of the droplet pooled in order to complete operations 1054, 1056, 1058 and 1060.

In an alternative example of a barcode oligonucleotide for use in RNA (e.g., cellular RNA) analysis as shown in FIG. 10, functional sequence 1008 may be a P5 sequence and functional sequence 1010 may be a R1 primer binding site. Moreover, the functional sequence 1030 may be a P7 sequence, functional sequence 1028 may be a R2 primer binding site, and functional sequence 1032 may be an i7 sample index sequence.

Figure 11:
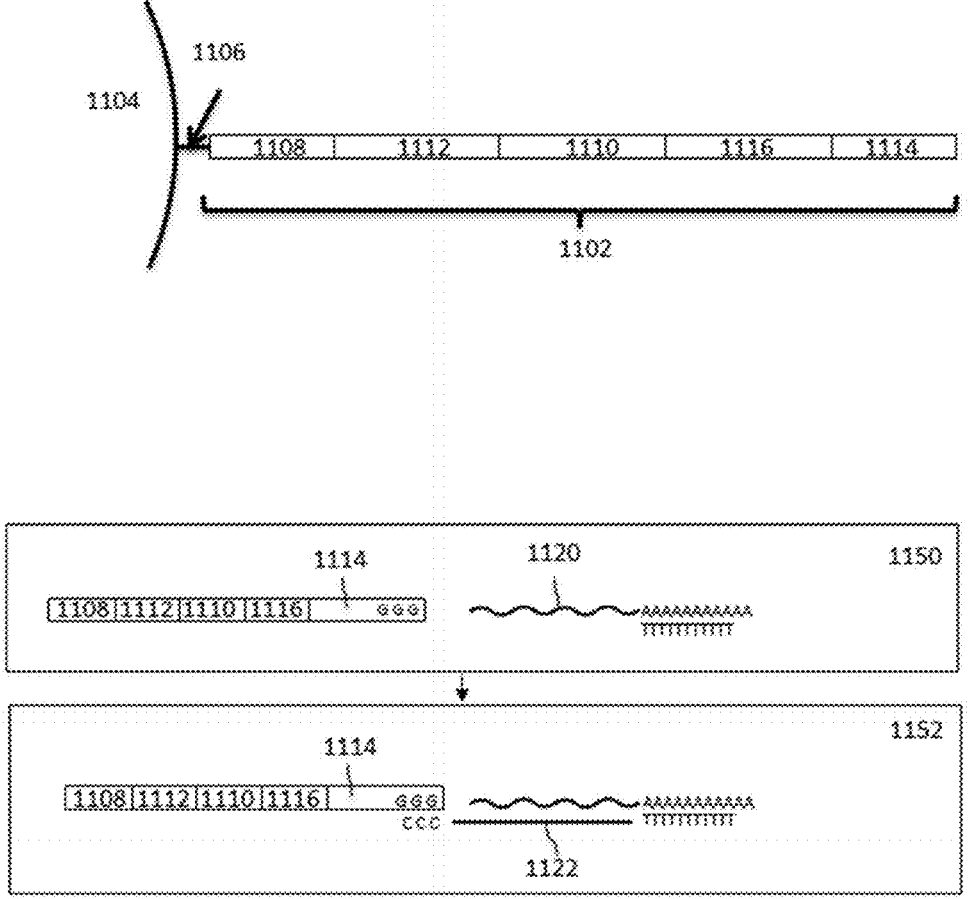
FIG. 11 provides schematic illustration of an example barcoded oligonucleotide structure for use in analysis of RNA and example operations for performing RNA analysis.

An additional example of a barcode oligonucleotide for use in RNA analysis, including messenger RNA (mRNA, including mRNA obtained from a cell) analysis is shown in FIG. 11. As shown, the overall oligonucleotide 1102 is coupled to a bead 1104 by a releasable linkage 1106, such as a disulfide linker. The oligonucleotide may include functional sequences that are used in subsequent processing, such as functional sequence 1108, which may include a sequencer specific flow cell attachment sequence, e.g., a P5 sequence, as well as functional sequence 1110, which may include sequencing primer sequences, e.g., a R1 primer binding site. In some cases, sequence 1108 is a P7 sequence and sequence 1110 is a R2 primer binding site. A barcode sequence 1112 is included within the structure for use in barcoding the sample RNA. An additional sequence segment 1116 may be provided within the oligonucleotide sequence. In some cases, this additional sequence can provide a unique molecular sequence segment, as described elsewhere herein. An additional sequence 1114 may be included to facilitate template switching, e.g., polyG. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead.

In an example method of cellular mRNA analysis and in reference to FIG. 11, a cell is co-partitioned along with a barcode bearing bead, poly-dT sequence, and other reagents such as reverse transcriptase, a reducing agent and dNTPs into a partition (e.g., a droplet in an emulsion). In operation 1150, the cell is lysed while the barcoded oligonucleotides are released from the bead (e.g., via the action of the reducing agent) and the poly-dT sequence hybridizes to the poly-A tail of mRNA 1120 released from the cell. Next, in operation 1152, the poly-dT sequence is then extended in a reverse transcription reaction using the mRNA as a template to produce a cDNA transcript 1122 complementary to the mRNA. Terminal transferase activity of the reverse transcriptase can add additional bases to the cDNA transcript (e.g., polyC). The additional bases added to the cDNA transcript, e.g., polyC, can then to hybridize with 1114 of the barcoded oligonucleotide. This can facilitate template switching and a sequence complementary to the barcode oligonucleotide can be incorporated into the cDNA transcript. The transcripts can be further processed (e.g., amplified, portions removed, additional sequences added, etc.) and characterized as described elsewhere herein, e.g., by sequencing. The configuration of the constructs generated by such a method can help minimize (or avoid) sequencing of the poly-dT sequence during sequencing.

Figure 12A:
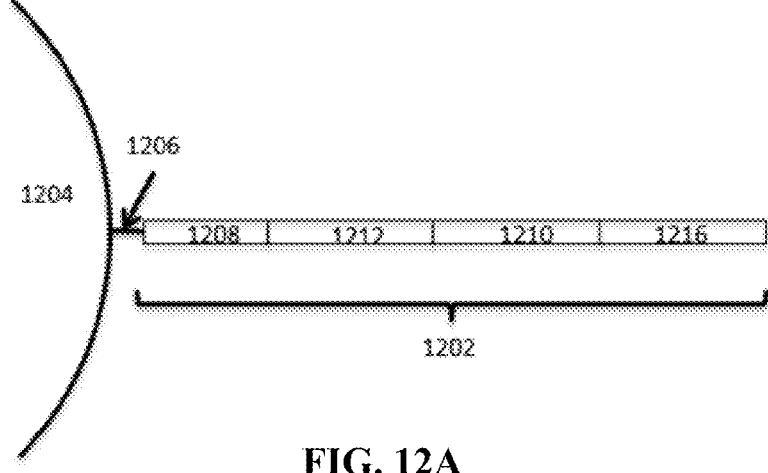
FIG. 12A-FIG. 12B provides schematic illustration of example barcoded oligonucleotide structure for use in analysis of RNA.

An additional example of a barcode oligonucleotide for use in RNA analysis, including cellular RNA analysis is shown in FIG. 12A. As shown, the overall oligonucleotide 1202 is coupled to a bead 1204 by a releasable linkage 1206, such as a disulfide linker. The oligonucleotide may include functional sequences that are used in subsequent processing, such as functional sequence 1208, which may include a sequencer specific flow cell attachment sequence, e.g., a P5 sequence, as well as functional sequence 1210, which may include sequencing primer sequences, e.g., a R1 primer binding site. In some cases, sequence 1208 is a P7 sequence and sequence 1210 is a R2 primer binding site. A barcode sequence 1212 is included within the structure for use in barcoding the sample RNA. An additional sequence segment 1216 may be provided within the oligonucleotide sequence. In some cases, this additional sequence can provide a unique molecular sequence segment, as described elsewhere herein. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead. In an example method of cellular RNA analysis using this barcode, a cell is co-partitioned along with a barcode bearing bead and other reagents such as RNA ligase and a reducing agent into a partition (e.g. a droplet in an emulsion). The cell is lysed while the barcoded oligonucleotides are released (e.g., via the action of the reducing agent) from the bead. The barcoded oligonucleotides can then be ligated to the 5' end of mRNA transcripts while in the partitions by RNA ligase. Subsequent operations may include purification (e.g., via solid phase reversible immobilization (SPRI)) and further processing (shearing, ligation of functional sequences, and subsequent amplification (e.g., via PCR)), and these operations may occur in bulk (e.g., outside the partition). In the case where a partition is a droplet in an emulsion, the emulsion can be broken and the contents of the droplet pooled for the additional operations.

Figure 12B:
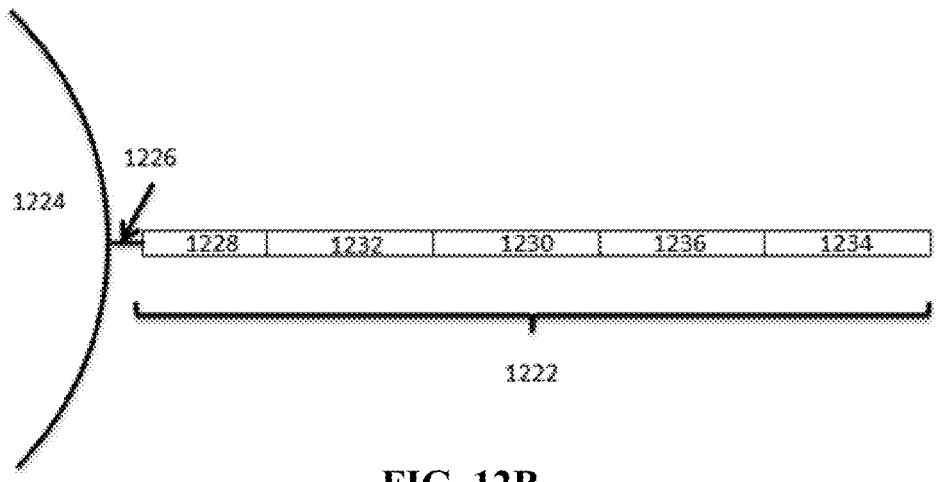

An additional example of a barcode oligonucleotide for use in RNA analysis, including cellular RNA analysis is shown in FIG. 12B. As shown, the overall oligonucleotide 1222 is coupled to a bead 1224 by a releasable linkage 1226, such as a disulfide linker. The oligonucleotide may include functional sequences that are used in subsequent processing, such as functional sequence 1228, which may include a sequencer specific flow cell attachment sequence, e.g., a P5 sequence, as well as functional sequence 1230, which may include sequencing primer sequences, e.g., a R1 primer binding site. In some cases, sequence 1228 is a P7 sequence and sequence 1230 is a R2 primer binding site. A barcode sequence 1232 is included within the structure for use in barcoding the sample RNA. A priming sequence 1234 (e.g., a random priming sequence) can also be included in the oligonucleotide structure, e.g., a random hexamer. An additional sequence segment 1236 may be provided within the oligonucleotide sequence. In some cases, this additional sequence provides a unique molecular sequence segment, as described elsewhere herein. As will be appreciated, although shown as a single oligonucleotide tethered to the surface of a bead, individual beads can include tens to hundreds of thousands or even millions of individual oligonucleotide molecules, where, as noted, the barcode segment can be constant or relatively constant for a given bead, but where the variable or unique sequence segment will vary across an individual bead. In an example method of cellular mRNA analysis using the barcode oligonucleotide of FIG. 12B, a cell is co-partitioned along with a barcode bearing bead and additional reagents such as reverse transcriptase, a reducing agent and dNTPs into a partition (e.g., a droplet in an emulsion). The cell is lysed while the barcoded oligonucleotides are released from the bead (e.g., via the action of the reducing agent). In some cases, sequence 1228 is a P7 sequence and sequence 1230 is a R2 primer binding site. In other cases, sequence 1228 is a P5 sequence and sequence 1230 is a R1 primer binding site. The priming sequence 1234 of random hexamers can randomly hybridize cellular mRNA. The random hexamer sequence can then be extended in a reverse transcription reaction using mRNA from the cell as a template to produce a cDNA transcript complementary to the mRNA and also includes each of the sequence segments 1228, 1232, 1230, 1236, and 1234 of the barcode oligonucleotide. Subsequent operations can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-dT sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method. The single cell analysis methods described herein may also be useful in the analysis of the whole transcriptome. Referring back to the barcode of FIG. 12B, the priming sequence 1234 may be a random N-mer. In some cases, sequence 1228 is a P7 sequence and sequence 1230 is a R2 primer binding site. In other cases, sequence 1228 is a P5 sequence and sequence 1230 is a R1 primer binding site. In an example method of whole transcriptome analysis using this barcode, the individual cell is co-partitioned along with a barcode bearing bead, poly-dT sequence, and other reagents such as reverse transcriptase, polymerase, a reducing agent and dNTPs into a partition (e.g., droplet in an emulsion). In an operation of this method, the cell is lysed while the barcoded oligonucleotides are released from the bead (e.g., via the action of the reducing agent) and the poly-dT sequence hybridizes to the poly-A tail of cellular mRNA. In a reverse transcription reaction using the mRNA as template, cDNA transcripts of cellular mRNA can be produced. The RNA can then be degraded with an RNase. The priming sequence 1234 in the barcoded oligonucleotide can then randomly hybridize to the cDNA transcripts. The oligonucleotides can be extended using polymerase enzymes and other extension reagents co-partitioned with the bead and cell similar to as shown in FIG. 3 to generate amplification products (e.g., barcoded fragments), similar to the example amplification product shown in FIG. 3 (panel F). The barcoded nucleic acid fragments may, in some cases subjected to further processing (e.g., amplification, addition of additional sequences, clean up processes, etc. as described elsewhere herein)

characterized, e.g., through sequence analysis. In this operation, sequencing signals can come from full length RNA.

Although operations with various barcode designs have been discussed individually, individual beads can include barcode oligonucleotides of various designs for simultaneous use.

In addition to characterizing individual cells or cell subpopulations from larger populations, the processes and systems described herein may also be used to characterize individual cells as a way to provide an overall profile of a cellular, or other organismal population. A variety of applications require the evaluation of the presence and quantification of different cell or organism types within a population of cells, including, for example, microbiome analysis and characterization, environmental testing, food safety testing, epidemiological analysis, e.g., in tracing contamination or the like. In particular, the analysis processes described above may be used to individually characterize, sequence and/or identify large numbers of individual cells within a population. This characterization may then be used to assemble an overall profile of the originating population, which can provide important prognostic and diagnostic information.

For example, shifts in human microbiomes, including, e.g., gut, buccal, epidermal microbiomes, etc., have been identified as being both diagnostic and prognostic of different conditions or general states of health. Using the single cell analysis methods and systems described herein, one can again, characterize, sequence and identify individual cells in an overall population, and identify shifts within that population that may be indicative of diagnostic ally relevant factors. By way of example, sequencing of bacterial 16S ribosomal RNA genes has been used as a highly accurate method for taxonomic classification of bacteria. Using the targeted amplification and sequencing processes described above can provide identification of individual cells within a population of cells. One may further quantify the numbers of different cells within a population to identify current states or shifts in states over time. See, e.g., Morgan et al, PLoS Comput. Biol., Ch. 12, December 2012, 8(12):e1002808, and Ram et al., Syst. Biol. Reprod. Med., June 2011, 57(3):162-170, each of which is incorporated herein by reference in its entirety for all purposes. Likewise, identification and diagnosis of infection or potential infection may also benefit from the single cell analyses described herein, e.g., to identify microbial species present in large mixes of other cells or other biological material, cells and/or nucleic acids, including the environments described above, as well as any other diagnostically relevant environments, e.g., cerebrospinal fluid, blood, fecal or intestinal samples, or the like.

The foregoing analyses may also be particularly useful in the characterization of potential drug resistance of different cells, e.g., cancer cells, bacterial pathogens, etc., through the analysis of distribution and profiling of different resistance markers/mutations across cell populations in a given sample. Additionally, characterization of shifts in these markers/mutations across populations of cells over time can provide valuable insight into the progression, alteration, prevention, and treatment of a variety of diseases characterized by such drug resistance issues.

Although described in terms of cells, it will be appreciated that any of a variety of individual biological organisms, or components of organisms are encompassed within this description, including, for example, cells, viruses, organelles, cellular inclusions, vesicles, or the like. Additionally, where referring to cells, it will be appreciated that such reference includes any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms.

Similarly, analysis of different environmental samples to profile the microbial organisms, viruses, or other biological contaminants that are present within such samples, can provide important information about disease epidemiology, and potentially aid in forecasting disease outbreaks, epidemics an pandemics.

As described above, the methods, systems and compositions described herein may also be used for analysis and characterization of other aspects of individual cells or populations of cells. In one example process, a sample is provided that contains cells that are to be analyzed and characterized as to their cell surface proteins. Also provided is a library of antibodies, antibody fragments, or other molecules having a binding affinity to the cell surface proteins or antigens (or other cell features) for which the cell is to be characterized (also referred to herein as cell surface feature binding groups). For ease of discussion, these affinity groups are referred to herein as binding groups. The binding groups can include a reporter molecule that is indicative of the cell surface feature to which the binding group binds. In particular, a binding group type that is specific to one type of cell surface feature will comprise a first reporter molecule, while a binding group type that is specific to a different cell surface feature will have a different reporter molecule associated with it. In some aspects, these reporter molecules will comprise oligonucleotide sequences. Oligonucleotide based reporter molecules provide advantages of being able to generate significant diversity in terms of sequence, while also being readily attachable to most biomolecules, e.g., antibodies, etc., as well as being readily detected, e.g., using sequencing or array technologies. In the example process, the binding groups include oligonucleotides attached to them. Thus, a first binding group type, e.g., antibodies to a first type of cell surface feature, will have associated with it a reporter oligonucleotide that has a first nucleotide sequence. Different binding group types, e.g., antibodies having binding affinity for other, different cell surface features, will have associated therewith reporter oligonucleotides that comprise different nucleotide sequences, e.g., having a partially or completely different nucleotide sequence. In some cases, for each type of cell surface feature binding group, e.g., antibody or antibody fragment, the reporter oligonucleotide sequence may be known and readily identifiable as being associated with the known cell surface feature binding group. These oligonucleotides may be directly coupled to the binding group, or they may be attached to a bead, molecular lattice, e.g., a linear, globular, cross-slinked, or other polymer, or other framework that is attached or otherwise associated with the binding group, which allows attachment of multiple reporter oligonucleotides to a single binding group.

In the case of multiple reporter molecules coupled to a single binding group, such reporter molecules can comprise the same sequence, or a particular binding group will include a known set of reporter oligonucleotide sequences. As between different binding groups, e.g., specific for different cell surface features, the reporter molecules can be different and attributable to the particular binding group.

Attachment of the reporter groups to the binding groups may be achieved through any of a variety of direct or indirect, covalent or non-covalent associations or attachments. For example, in the case of oligonucleotide reporter groups associated with antibody based binding groups, such oligonucleotides may be covalently attached to a portion of an antibody or antibody fragment using chemical conjugation techniques (e.g., Lightning-Link® antibody labeling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available (See, e.g., Fang, et al., Fluoride-Cleavable Biotinylation Phosphoramidite for 5'-end-Labeling and Affinity Purification of Synthetic Oligonucleotides, Nucleic Acids Res. Jan. 15, 2003; 31(2):708-715; DNA 3' End Biotinylation Kit, available from Thermo Scientific; and the SiteClick™ Antibody Labeling System available from Thermo Fisher Scientific, the full disclosures of which are incorporated herein by reference in their entirety for all purposes). Likewise, protein and peptide biotinylation techniques have been developed and are readily available (See, e.g., U.S. Pat. No. 6,265,552, the full disclosures of which are incorporated herein by reference in their entirety for all purposes).

The reporter oligonucleotides may be provided having any of a range of different lengths, depending upon the diversity of reporter molecules desired or a given analysis, the sequence detection scheme employed, and the like. In some cases, these reporter sequences can be greater than about 5 nucleotides in length, greater than about 10 nucleotides in length, greater than about 20, 30, 40, 50, 60, 70, 80, 90, 100, 120, 150 or even 200 nucleotides in length. In some cases, these reporter nucleotides may be less than about 250 nucleotides in length, less than about 200, 180, 150, 120 100, 90, 80, 70, 60, 50, 40, or even 30 nucleotides in length. In many cases, the reporter oligonucleotides may be selected to provide barcoded products that are already sized, and otherwise configured to be analyzed on a sequencing system. For example, these sequences may be provided at a length that ideally creates sequenceable products of a desired length for particular sequencing systems. Likewise, these reporter oligonucleotides may include additional sequence elements, in addition to the reporter sequence, such as sequencer attachment sequences, sequencing primer sequences, amplification primer sequences, or the complements to any of these.

In operation, a cell-containing sample is incubated with the binding molecules and their associated reporter oligonucleotides, for any of the cell surface features desired to be analyzed. Following incubation, the cells are washed to remove unbound binding groups. Following washing, the cells are partitioned into separate partitions, e.g., droplets, along with the barcode carrying beads described above, where each partition includes a limited number of cells, e.g., in some cases, a single cell. Upon releasing the barcodes from the beads, they will prime the amplification and barcoding of the reporter oligonucleotides. As noted above, the barcoded replicates of the reporter molecules may additionally include functional sequences, such as primer sequences, attachment sequences or the like.

The barcoded reporter oligonucleotides are then subjected to sequence analysis to identify which reporter oligonucleotides bound to the cells within the partitions. Further, by also sequencing the associated barcode sequence, one can identify that a given cell surface feature likely came from the same cell as other, different cell surface features, whose reporter sequences include the same barcode sequence, i.e., they were derived from the same partition. Based upon the reporter molecules that emanate from an individual partition based upon the presence of the barcode sequence, one may then create a cell surface profile of individual cells from a population of cells. Profiles of individual cells or populations of cells may be compared to profiles from other cells, e.g., 'normal' cells, to identify variations in cell surface features, which may provide diagnostically relevant information. In particular, these profiles may be particularly useful in the diagnosis of a variety of disorders that are characterized by variations in cell surface receptors, such as cancer and other disorders.

IV. Engineered Reverse Transcription Enzyme Variants

One of the major challenges in cDNA synthesis reactions are interference in cDNA synthesis from RNA secondary structures. While a higher reaction temperature can remove secondary structure from the template RNA, elevated temperatures typically lead to lower reverse-transcriptase (RT) enzyme activity without the use of an efficient, thermostable RT enzyme. Additionally, RT enzyme activity can be reduced by inhibitors, such as cell lysates and associated reagents.

Wild-type (WT) Moloney Murine Leukemia Virus (MMLV) reverse-transcriptase is an RT enzyme that is typically inactivated at higher temperatures. However, several commercially available mutant MMLV RT enzymes exhibit improved thermostability, fidelity, substrate affinity, and/or reduced terminal deoxynucleotidyltransferase activity.

Disclosed herein, in some embodiments, are engineered reverse transcription enzymes, comprising an amino acid sequence that is at least 80% identical to SEQ ID NO: 3, wherein said amino acid sequence comprises: (a) a truncation of at least 15 amino acids from the N-terminus relative to SEQ ID NO: 3; and (b) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3. In some instances, the one or more mutations in (b) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, engineered reverse transcription enzymes further comprise an affinity tag at said N-terminus or at a C-terminus of said amino acid sequence. In some instances, said affinity tag include, but are not limited to, albumin binding protein (ABP), AU1 epitope, AU5 epitope, T7-tag, V5-tag, B-tag, Chloramphenicol Acetyl Transferase (CAT), Dihydrofolate reductase (DHFR), AviTag, Calmodulin-tag, polyglutamate tag, E-tag, FLAG-tag, HA-tag, Myc-tag, NE-tag, S-tag, SBP-tag, Doftag 1, Softag 3, Spot-tag, tetracysteine (TC) tag, Ty tag, VSV-tag, Xpress tag, biotin carboxyl carrier protein (BCCP), green fluorescent protein tag, HaloTag, Nus-tag, thioredoxin-tag, Fc-tag, cellulose binding domain, chitin binding protein (CBP), choline-binding domain, galactose binding domain, maltose binding protein (MBP), Horseradish Peroxidase (HRP), Strep-tag, HSV epitope, Ketosteroid isomerase (KSI), KT3 epitope, LacZ, Luciferase, PDZ domain, PDZ ligand, Polyarginine (Arg-tag), Polyaspartate (Asp-tag), Polycysteine (Cys-tag), Polyphenylalanine (Phe-tag), Profinity eXact, Protein C, S1-tag, S1-tag, Staphylococcal protein A (Protein A), Staphylococcal protein G (Protein G), Small Ubiquitin-like Modifier (SUMO), Tandem Affinity Purification (TAP), TrpE, Ubiquitin, Universal, glutathione-S-transferase (GST), and poly(His) tag. In some instances, said affinity tag is at least 5 histidine amino acids.

In some embodiments, engineered reverse transcription enzymes further comprises a protease cleavage sequence, wherein cleavage of said protease cleavage sequence by a protease results in cleavage of said affinity tag from said engineered reverse transcription enzyme. In some instances, protease cleavage sequence is the protease cleavage sequence recognized by a protease including, but not limited to, alanine carboxypeptidase, *Armillaria mellea* astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, Iga-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase. In some instances, said protease cleavage sequence is a thrombin cleavage sequence.

Disclosed herein, in some embodiments, are engineered reverse transcription enzyme variants, comprising an amino acid sequence that is at least 80% identical to the amino acid (polypeptide) sequence of SEQ ID NO: 3, wherein said amino acid sequence is characterized by two or more of: (i) a truncation of at least 15 amino acids from an N terminus of said amino acid sequence; (ii) a sequence of at least 5 histidine amino acids at said N terminus of said amino acid sequence; (iii) a thrombin cleavage recognition site; and (iv) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3. Disclosed herein, in some embodiments, are engineered reverse transcription enzyme variants, comprising an amino acid sequence that is at least 80% identical to the amino acid (polypeptide) sequence of SEQ ID NO: 3, wherein said amino acid sequence is characterized by two or more of: (i) a truncation of at least 15 amino acids from an N terminus of said amino acid sequence; (ii) a sequence of at least 5 histidine amino acids at said N terminus of said amino acid sequence; (iii) a thrombin cleavage recognition site; and (iv) one or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

Wild-type MMLV expresses a 1738-amino acid polypeptide chain (see, e.g., UniProt P03355) which is processed by viral protease p14 into a number of mature proteins, including the wild-type MMLV p80 reverse transcriptase enzyme (see, e.g., SEQ ID NO: 3).

Table 1

| Sequences |
| --- |

SEQ ID NO: 1 ATGGGTAGCTCACATCACCATCATCATCATTCTTCT
GGTCTGGTCCCACGCGGCAGCACTTGGCTGTCTGAT
TTCCCTCAGGCGTGGGCCGAAACGGGTGGCATGGGT
CTGGCAGTGCGTCAGGCACCGCTGATTATTCCGCTG
AAAGCGACGTCGACCCCGGTGAGCATCAAGCAATAT
CCGATGTCCCAAGAGGCGCGCTTAGGTATTAAGCCG
CACATTCAGCGTCTGCTGGATCAAGGTATTCTGGTT
CCGTGTCAGAGCCCGTGGAATACCCCGCTTCTCCCG
GTGAAGAAACCGGGCACGAACGATTACCGTCCAGTC
CAAGACTTGCGCGAAGTTAACAAGCGCGTTGAAGAT
ATTCACCCGACCGTCCCGAACCCGTACAATCTGCTG
AGCGGTCTGCCGCCAAGCCACCAATGGTACACCGTG
CTGGATCTGAAAGATGCTTTCTTCTGTCTGCGTCTG
CACCCAACCAGCCAGCCTCTGTTTGCATTTGAGTGG
CGTGACCCTGAGATGGGTATTAGCGGCCAGCTGACG
TGGACCCGCCTGCCGCAAGGTTTTAAGAATTCCCCT
ACGCTGTTTGACGAAGCGCTGCACCGTGACCTGGCG
GATTTCCGTATCCAGCACCCGGACCTGATCTTGCTG
CAGTACGTTGATGACCTGTTGCTGGCGGCGACGAGC
GAGCTGGATTGCCAACAGGGCACCCGTGCGCTGTTG
CAGACCTTGGGTAACCTGGGTTATCGCGCTAGCGCG
AAGAAAGCGCAGATTTGCCAAAAACAAGTTAAGTAT
CTGGGCTACCTGTTAAAGGAAGGCCAACGTTGGCTG
ACCGAAGCCCGCAAAGAAACTGTCATGGGTCAGCCG
ACCCCGAAAACGCCACGCCAACTGCGTGAGTTCTTG
GGCACCGCGGGTTTCTGCCGCCTGTGGATCCCGGGC
TTTGCCGAAATGGCAGCCCGCTGTATCCGTTGACC
AAGACCGGCACCCTGTTCAACTGGGGTCCGGACCAG
CAGAAAGCGTACCAAGAAATTAAACAAGCACTGCTG
ACGGCACCGGCGCTGGGTCTGCCGGACCTGACCAAG
CCGTTTGAGCTGTTCGTGGATGAGAAGCAAGGTTAC
GCGAAGGGCGTGTTGACCCAGAAATTGGGTCCGTGG
CGTCGTCCGGTTGCATACCTGTCCAAGAAACTGGAC
CCGGTTGCTGCTGGTTGGCCGCCTTGCCTGCGCATG
GTTGCCGCTATCGCGGTGCTGACTAAAGACGCGGGT
AAGCTGACGATGGGTCAACCGCTGGTGATCAAGGCA
CCGCATGCAGTCGAGGCCCCTTGTTAAGCAACCGCCA
GATAGATGGCTGAGCAACGCGCGTATGACGCATTAC
CAGGCACTGCTGTTGGACACCGATCGTGTGCAGTTT
GGCCCGGTCGTTGCCGCTCAACCCGGCGACCCTGCTG
CCGCTCCCGGAAGAAGGCTTGCAGCACAACTGTTTG
GACATCCTGGCAGAGGCGCACGGCACTCGCCCGGAT
CTGACGGACCAGCCGCTGCCGGACGCCGATCATACC
TGGTATACGAATGGTAGCAGCCTGTTGCAAGAGGGT
CAGCGTAAGGCCGGTGCCGCGGTCACCACCGAGACT
GAAGTGATTTGGGCTAAAGCATTGCCTGCGGGTACC
AGCGCGCAGCGTGCCGAGCTGATCGCACTGACCCAA
GCGCTGAAAATGGCTGAGGGTAAGAAACTGAATGTG
TACACGGATAGCCGTTATGCCTTTGCGACCGCCCAC
ATTCACGGCGAGATCTATCGCCGTCGCGGCCTGCTG
ACGTCCGAAGGCAAAGAGATCAAGAATAAAGACGAA
ATTCTGGCGCTGCTGAAAGCGCTGTTCCTGCCGAAA
CGTCTGTCGATCATCCATTGCCCGGGTCACCAGAAA
GGCCACAGCGCAGAGGCGCGTGGTAATCGCATGGCT
GACCAGGCTGCGCGTAAAGCCGCAATTACCGAAACC
CCGGACACCAGCACGCTGCTGATCGAGAATAGCAGC
CCGAACAGCCGTCTGATCAATTGATAA

SEQ ID NO: 2 MGSSHHHHHHSSGLVPRGSTWLSDFPQAWAETGGMG
LAVRQAPLIIPLKATSTPVSIKQYPMSQEARLGIKP
HIQRLLDQGILVPCQSPWNTPLLPVKKPGTNDYRPV
QDLREVNKRVEDIHPTVPNPYNLLSGLPPSHQWYTV
LDLKDAFFCLRLHPTSQPLFAFEWRDPEMGISGQLT
WTRLPQGFKNSPTLFDEALHRDLADFRIQHPDLILL
QYVDDLLLAATSELDCQQGTRALLQTLGNLGYRASA
KKAQICQKQVKYLGYLLKEGQRWLTEARKETVMGQP
TPKTPRQLREFLGTAGFCRLWIPGFAEMAAPLYPLT
KTGTLFNWGPDQQKAYQEIKQALLTAPALGLPDLTK
PFELFVDEKQGYAKGVLTQKLGPWRRPVAYLSKKLD
PVAAGWPPCLRMVAAIAVLTKDAGKLTMGQPLVIKA
PHAVEALVKQPPDRWLSNARMTHYQALLLDTDRVQF
GPVVALNPATLLPLPEEGLQHNCLDILAEAHGTRPD
LTDQPLPDADHTWYTNGSSLLQEGQRKAGAAVTTET
EVIWAKALPAGTSAQRAELIALTQALKMAEGKKLNV
YTDSRYAFATAHIHGEIYRRRGLLTSEGKEIKNKDE
ILALLKALFLPKRLSIIHCPGHQKGHSAEARGNRMA
DQAARKAAITETPDTSTLLIENSSPNSRLIN

Table 1-continued

Sequences

SEQ ID NO: 3    TLNIEDEHRLHETSKEPDVSLGSTWLSDFPQAWAET
GGMGLAVRQAPLIIPLKATSTPVSIKQYPMSQEARL
GIKPHIQRLLDQGILVPCQSPWNTPLLPVKKPGTND
YRPVQDLREVNKRVEDIHPTVPNPYNLLSGLPPSHQ
WYTVLDLKDAFFCLRLHPTSQPLFAFEWRDPEMGIS
GQLTWTRLPQGFKNSPTLFDEALHRDLADFRIQHPD
LILLQYVDDLLLAATSELDCQQGTRALLQTLGNLGY
RASAKKAQICQKQVKYLGYLLKEGQRWLTEARKETV
MGQPTPKTPRQLREFLGTAGFCRLWIPGFAEMAAPL
YPLTKTGTLFNWGPDQQKAYQEIKQALLTAPALGLP
DLTKPFELFVDEKQGYAKGVLTQKLGPWRRPVAYLS
KKLDPVAAGWPPCLRMVAAIAVLTKDAGKLTMGQPL
VILAPHAVEALVKQPPDRWLSNARMTHYQALLLDTD
RVQFGPVVALNPATLLPLPEEGLQHNCLDILAEAHG
TRPDLTDQPLPDADHTWYTDGSSLLQEGQRKAGAAV
TTETEVIWAKALPAGTSAQRAELIALTQALKMAEGK
EKLNVYTDSRYAFATAHIHGEIYRRRGLLTSGKEIK
NKDEILALLKALFLPKRLSIIHCPGHQKGHSAEARG
NRMADQAARKAAITETPDTSTLL

SEQ ID NO: 4    ATGGGTAGCTCACATCACCATCATCATCATTCTTCT
GGTCTGGTCCCACGCGGCAGCACTTGGCTGTCTGAT
TTCCCTCAGGCGTGGGCCGAAACGGGTGGCATGGGT
CTGGCAGTGCGTCAGGCACCGCTGATTATTCCGCTG
AAAGCGACGTCGACCCCGGTGAGCATCAAGCAATAT
CCGATGTCCCAAAAGGCGCGCTTAGGTATTAAGCCG
CACATTCAGCGTCTGCTGGATCAAGGTATTCTGGTT
CCGTGTCAGAGCCCGTGGAATACCCCGCTTCTCCCG
GTGAAGAAACCGGGCACGAACGATTACCGTCCAGTC
CAAGACTTGCGCGAAGTTAACAAGCGCGTTGAAGAT
ATTCACCCGACCGTCCCGAACCCGTACAATCTGCTG
AGCGGTCCGCCGCCAAGCCACCAATGGTACACCGTG
CTGGATCTGAAAGATGCTTTCTTCTGTCTGCGTCTG
CACCCAACCAGCCAGCCTCTGTTTGCATTTGAGTGG
CGTGACCCTGAGATGGGTATTAGCGGCCAGCTGACG
TGGACCCGCCTGCCGCAAGGTTTTAAGAATTCCCCT
ACGCTGTTTAACGAAGCGCTGCACCGTGACCTGGCG
GATTTCCGTATCCAGCACCCGGACCTGATCTTGCTG
CAGTACGTTGATGACCTGTTGCTGGCGGCGACGAGC
GAGCTGGATTGCCAACAGGGCACCCGTGCGCTGTTG
CAGACCTTGGGTAACCTGGGTTATCGCGCTAGCGCG
AAGAAAGCGCAGATTTGCCAAAAACAAGTTAAGTAT
CTGGGCTACCTGTTAAAGGAAGGCCAACGTTGGCTG
ACCGAAGCCCGCAAAGAAACTGTCATGGGTCAGCCG
ACCCCGAAAACGCCACGCCAACTGCGTAGGTTCTTG
GGCAAAGCGGGTTTCTGCCGCCTGTTCATCCCGGGC
TTTGCCGAAATGGCAGCCCCGCTGTATCCGTTGACC
AAGCCGGGCACCCTGTTCAACTGGGGTCCGGACCAG
CAGAAAGCGTACCAAGAAATTAAACAAGCACTGCTG
ACGGCACCGGCGCTGGGTCTGCCGGACCTGACCAAG
CCGTTTGAGCTGTTCGTGGATGAGAAGCAAGGTTAC
GCGAAGGGCGTGTTGACCCAGAAATTGGGTCCGTGG
CGTCGTCCGGTTGCATACCTGTCCAAGAAACTGGAC
CCGGTTGCTGCTGGTTGGCCGCCTTGCCTGCGCATG
GTTGCCGCTATCGCGGTGCTGACTAAAGACGCGGGT
AAGCTGACGATGGGTCAACCGCTGGTGATCAAGGCA
CCGCATGCAGTCGAGGCCCTTGTTAAGCAACCGGCA
GGCAGATGGCTGAGCAAGGCGCGTATGACGCATTAC
CAGGCACTGCTGTTGGACACCGATCGTGTGCAGTTT
GGCCCGGTCGTTGCGCTCAACCCGGCGACCCTGCTG
CCGCTCCCGGAAGAAGGCTTGCAGCACAACTGTTTG
GACATCCTGGCAGAGGCGCACGGCACTCGCCCGGAT
CTGACGGACCAGCCGCTGCCGGACGCCGATCATACC
TGGTATACGAATGGTAGCAGCCTGTTGCAAGAGGGT
CAGCGTAAGGCCGGTGCCGCGGTCACCACCGAGACT
GAAGTGATTTGGGCTAAAGCATTGCCTGCGGGTACC
AGCGCGCAGCGTGCCGAGCTGATCGCACTGACCCAA
GCGCTGAAAATGGCTGAGGGTAAGAAACTGAATGTG
TACACGGATAGCCGTTATGCCTTTGCGACCGCCCAC
ATTCACGGCGAGATCTATCGCCGTCGCGGCTGGCTG
ACGTCCAAAGGCAAGAGATCAAGAATAAAGACGAA
ATTCTGGCGCTGCTGAAAGCGCTGTTCCTGCCGAAA
CGTCTGTCGATCATCCATTGCCCGGGTCACCAGAAA
GGCCACAGCGCAGAGGCGCGTGGTAATCGCATGGCT
GACCAGGCTGCGCGTAAAGCCGCAATTACCGAAACC
CCGGACACCAGCACGCTGCTGATCGAGAATAGCAGC
CCGAACAGCCGTCTGATCAATTGATAA

Table 1-continued

Sequences

SEQ ID NO: 5    MGSSHHHHHHSSGLVPRGSTWLSDFPQAWAETGGMG
LAVRQAPLIIPLKATSTPVSIKQYPMSQKARLGIKP
HIQRLLDQGILVPCQSPWNTPLLPVKKPGTNDYRPV
QDLREVNKRVEDIHPTVPNPYNLLSGPPPSHQWYTV
LDLKDAFFCLRLHPTSQPLFAFEWRDPEMGISGQLT
WTRLPQGFKNSPTLFNEALHRDLADFRIQHPDLILL
QYVDDLLLAATSELDCQQGTRALLQTLGNLGYRASA
KKAQICQKQVKYLGYLLKEGQRWLTEARKETVMGQP
TPKTPRQLRRFLGKAGFCRLFIPGFAEMAAPLYPLT
KPGTLFNWGPDQQKAYQEIKQALLTAPALGLPDLTK
PFELFVDEKQGYAKGVLTQKLGPWRRPVAYLSKKLD
PVAAGWPPCLRMVAAIAVLTKDAGKLTMGQPLVIKA
PHAVEALVKQPAGRWLSKARMTHYQALLLDTDRVQF
GPVVALNPATLLPLPEEGLQHNCLDILAEAHGTRPD
LTDQPLPDADHTWYTNGSSLLQEGQRKAGAAVTTET
EVIWAKALPAGTSAQRAELIALTQALKMAEGKKLNV
YTDSRYAFATAHIHGEIYRRRGWLTSKGKEIKNKDE
ILALLKALFLPKRLSIIHCPGHQKGHSAEARGNRMA
DQAARKAAITETPDTSTLLIENSSPNSRLIN

SEQ ID NO: 6    TWLSDFPQAWAETGGMGLAVRQAPLIIPLKATSTPV
SIKQYPMSQKARLGIKPHIQRLLDQGILVPCQSPWN
TPLLPVKKPGTNDYRPVQDLREVNKRVEDIHPTVPN
PYNLLSGPPPSHQWYTVLDLKDAFFCLRLHPTSQPL
FAFEWRDPEMGISGQLTWTRLPQGFKNSPTLFNEAL
HRDLADFRIQHPDLILLQYVDDLLLAATSELDCQQG
TRALLQTLGNLGYRASAKKAQICQKQVKYLGYLLKE
GQRWLTEARKETVMGQPTPKTPRQLRRFLGKAGFCR
LFIPGFAEMAAPLYPLTKPGTLFNWGPDQQKAYQEI
KQALLTAPALGLPDLTKPFELFVDEKQGYAKGVLTQ
KLGPWRRPVAYLSKKLDPVAAGWPPCLRMVAAIAVL
TKDAGKLTMGQPLVIKAPHAVEALVKQPAGRWLSKA
RMTHYQALLLDTDRVQFGPVVALNPATLLPLPEEGL
QHNCLDILAEAHGTRPDLTDQPLPDADHTWYTNGSS
LLQEGQRKAGAAVTTETEVIWAKALPAGTSAQRAEL
AHIALTQALKMAEGKKLNVYTDSRYAFATIHGEIYR
RRGWLTSKGKEIKNKDEILALLKALFLPKRLSIIHC
PGHQKGHSAEARGNRMADQAARKAAITETPDTSTLL

As used herein, the term "variant" may have at least about 45%, at least about 50%, at least about 55%, at least about 60%, at least about 65%, at least about 70%, at least about 75%, at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, or at least about 99.5% sequence identity to a polypeptide sequence when optimally aligned for comparison.

As used herein, a polypeptide having a certain percent (e.g., at least 80%, at least 85%, at least 90%, at least 95%, or at least 99%) of sequence identity with another sequence means that, when aligned, that percentage of bases or amino acid residues are the same in comparing the two sequences. This alignment and the percent homology or identity can be determined using any suitable software program known in the art, for example those described in CURRENT PROTOCOLS IN MOLECULAR BIOLOGY, Ausubel et al., eds., 1987, Supplement 30, section 7.7.18. Representative programs include the Vector NTI Advance™ 9.0 (Invitrogen Corp. Carlsbad, Calif.), GCG Pileup, FASTA (Pearson et al. (1988) Proc. Natl Acad. ScL USA 85:2444-2448), and BLAST (BLAST Manual, Altschul et al., Nat'l Cent. Biotechnol. Inf., Nat'l Lib. Med. (NCIB NLM NIH), Bethesda, Md., and Altschul et al., (1997) Nucleic Acids Res. 25:3389-3402) programs. Another typical alignment program is ALIGN Plus (Scientific and Educational Software, PA), generally using default parameters. Another sequence software program that finds use is the TFASTA Data Searching Program available in the Sequence Software Package Version 6.0 (Genetics Computer Group, University of Wisconsin, Madison, Wis.).

In some embodiments, the engineered reverse transcription enzyme comprises an amino acid sequence that is at least 80% identical to a WT MMLV RT enzyme (SEQ ID NO: 3). In some embodiments, the engineered reverse transcription enzyme comprises a nucleotide sequence that is at least 80% identical to a nucleotide sequence according to SEQ ID NO: 1. In some embodiments, the engineered reverse transcription enzyme comprises an amino acid sequence that is at least 80% identical to SEQ ID NO: 2. In some embodiments, the engineered reverse transcription enzyme comprises a nucleotide sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleotide sequence according to SEQ ID NO. 1. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 2. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 3.

In some embodiments, the engineered reverse transcription enzyme comprises an amino acid sequence that is at least 80% identical to a WT MMLV RT enzyme (SEQ ID NO: 3) over a span of at least 150 amino acid residues. In some embodiments, the engineered reverse transcription enzyme comprises a nucleotide sequence that is at least 80% identical to a nucleotide sequence according to SEQ ID NO: 1 over a span of at least 450 nucleotides. In some embodiments, the engineered reverse transcription enzyme comprises an amino acid sequence that is at least 80% identical to SEQ ID NO: 2 over a span of at least 150 amino acid residues. In some embodiments, the engineered reverse transcription enzyme comprises a nucleotide sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleotide sequence according to SEQ ID NO. 1 over a span of at least 450 nucleotides. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 2 over a span of at least 150 amino acid residues. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 3 over a span of at least 150 amino acid residues.

In some embodiments, the engineered reverse transcription enzyme comprises an amino acid sequence that is at least 80% identical to a WT MMLV RT enzyme (SEQ ID NO: 3) over a span of at least 300 amino acid residues. In some embodiments, the engineered reverse transcription enzyme comprises a nucleotide sequence that is at least 80% identical to a nucleotide sequence according to SEQ ID NO: 1 over a span of at least 900 nucleotides. In some embodiments, the engineered reverse transcription enzyme comprises an amino acid sequence that is at least 80% identical to SEQ ID NO: 2 over a span of at least 300 amino acid residues. In some embodiments, the engineered reverse transcription enzyme comprises a nucleotide sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleotide sequence according to SEQ ID NO. 1 over a span of at least 900 nucleotides. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 2 over a span of at least 300 amino acid residues. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 3 over a span of at least 300 amino acid residues.

In some embodiments, the engineered reverse transcription enzyme comprises an amino acid sequence that is at least 80% identical to a WT MMLV RT enzyme (SEQ ID NO: 3) over a span of at least 450 amino acid residues. In some embodiments, the engineered reverse transcription enzyme comprises a nucleotide sequence that is at least 80% identical to a nucleotide sequence according to SEQ ID NO: 1 over a span of at least 1,350 nucleotides. In some embodiments, the engineered reverse transcription enzyme comprises an amino acid sequence that is at least 80% identical to SEQ ID NO: 2 over a span of at least 450 amino acid residues. In some embodiments, the engineered reverse transcription enzyme comprises a nucleotide sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleotide sequence according to SEQ ID NO. 1 over a span of at least 1,350 nucleotides. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 2 over a span of at least 450 amino acid residues. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 3 over a span of at least 450 amino acid residues.

In some embodiments, the engineered reverse transcription enzyme comprises an amino acid sequence that is at least 80% identical to a WT MMLV RT enzyme (SEQ ID NO: 3) over a span of at least 600 amino acid residues. In some embodiments, the engineered reverse transcription enzyme comprises a nucleotide sequence that is at least 80% identical to a nucleotide sequence according to SEQ ID NO: 1 over a span of at least 1,800 nucleotides. In some embodiments, the engineered reverse transcription enzyme comprises an amino acid sequence that is at least 80% identical to SEQ ID NO: 2 over a span of at least 600 amino acid residues. In some embodiments, the engineered reverse transcription enzyme comprises a nucleotide sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleotide sequence according to SEQ ID NO. 1 over a span of at least 1,800 nucleotides. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 2 over a span of at least 600 amino acid residues. In some embodiments, the engineered reverse transcription enzyme comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO. 3 over a span of at least 600 amino acid residues.

In some embodiments, the engineered reverse transcription enzyme comprises a truncation of at least 15 amino acids from the N terminus of the engineered reverse transcription enzyme, as compared to a WT MMLV RT enzyme (e.g., SEQ ID NO: 3). In some embodiments, the engineered reverse transcription enzyme comprises a truncation of at least 20 amino acids from the N terminus of the engineered reverse transcription enzyme, as compared to a WT MMLV RT enzyme. In some embodiments, the engineered reverse transcription enzyme comprises a truncation of at least 21 amino acids from the N terminus of the engineered reverse transcription enzyme, as compared to a WT MMLV RT enzyme. In some embodiments, the engineered reverse transcription enzyme comprises a truncation of at least 25 amino acids from the N terminus of the engineered reverse transcription enzyme, as compared to a WT MMLV RT enzyme. In some embodiments, the engineered reverse transcription enzyme comprises a truncation of at least 30 amino acids from the N terminus of the engineered reverse transcription enzyme, as compared to a WT MMLV RT enzyme. In some embodiments, the engineered reverse transcription enzyme comprises a truncation of at least 35 amino acids from the N terminus of the engineered reverse transcription enzyme, as compared to a WT MMLV RT enzyme. In some embodiments, the engineered reverse transcription enzyme comprises a truncation of at least 40 amino acids from the N terminus of the engineered reverse transcription enzyme, as compared to a WT MMLV RT enzyme. In some embodiments, the engineered reverse transcription enzyme comprises a truncation of at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 amino acids from the N terminus of the engineered reverse transcription enzyme, as compared to a WT MMLV RT enzyme (SEQ ID NO: 3). In some embodiments, the N-terminal truncation in the engineered reverse transcription enzyme increase protein solubility as compared to a WT MMLV RT.

In some embodiments, the engineered reverse transcription enzyme comprises a sequence of at least 5 histidine amino acids at the N terminus of the enzyme. In some embodiments, the engineered reverse transcription enzyme comprises 6 histidine amino acids (SEQ ID NO:9) at the N terminus of the engineered reverse transcription enzyme. In some embodiments, the engineered reverse transcription enzyme comprises a thrombin cleavage recognition site. In some embodiments, the engineered reverse transcription enzyme comprises a sequence of at least 5 histidine amino acids at the N terminus of the enzyme and a thrombin cleavage recognition site. In some embodiments, the engineered reverse transcription enzyme comprises 6 histidine amino acids (SEQ ID NO:9) and a thrombin cleavage recognition site at the N-terminus of the engineered reverse transcription enzyme. In some embodiments, the 6 histidine amino acids (SEQ ID NO:9) and thrombin cleavage recognition site at the N-terminus of the engineered reverse transcription enzyme has an amino acid sequence of MRSSHHHHHHSSGLVPR (SEQ ID NO: 8).

In some embodiments, the engineered reverse transcription enzyme comprises at least 5 histidine amino acids at the N-terminus and/or a thrombin cleavage sequence at the N terminus of the engineered reverse transcription enzyme in addition to the N-terminal truncations described above. For example, in some embodiments, the engineered reverse transcription enzyme comprises (a) a truncation of at least 15 amino acids from the N terminus of the engineered RT enzyme as compared to a WT MMLV RT enzyme, (b) at least 5 histidine amino acids at the N-terminus of the engineered reverse transcription enzyme, and (c) a thrombin cleavage recognition site at the N terminus of the enzyme. In some embodiments, the engineered reverse transcription enzyme comprises (a) a truncation of at least 21 amino acids from the N terminus of the engineered RT enzyme as compared to a WT MMLV RT enzyme, (b) at least 5 histidine amino acids at the N-terminus of the engineered reverse transcription enzyme, and (c) a thrombin cleavage recognition site at the N terminus of the enzyme. In some embodiments, the engineered reverse transcription enzyme comprises (a) a truncation of at least 25 amino acids from the N terminus of the engineered RT enzyme as compared to a WT MMLV RT enzyme, (b) at least 5 histidine amino acids at the N-terminus of the engineered reverse transcription enzyme, and (c) a thrombin cleavage recognition site at the N terminus of the enzyme.

In some embodiments, the engineered reverse transcription enzyme comprises a truncation of at least 15 amino acids from the N terminus of the engineered RT enzyme as compared to a WT MMLV RT enzyme and a MRSSHHHHHHSSGLVPR (SEQ ID NO: 8) amino acid sequence at the N terminus of the engineered reverse transcription enzyme. In some embodiments, the engineered reverse transcription enzyme comprises a truncation of at least 21 amino acids from the N terminus of the engineered RT enzyme as compared to a WT MMLV RT enzyme and further comprises a MRSSHHHHHHSSGLVPR (SEQ ID NO:8) amino acid sequence at the N terminus of the engineered reverse transcription enzyme. In some embodiments, the engineered reverse transcription enzyme comprises a truncation of at least 25 amino acids from the N terminus of the engineered RT enzyme as compared to a WT MMLV RT enzyme and further comprises a MRSSHHHHHHSSGLVPR (SEQ ID NO:8) amino acid sequence at the N terminus of the engineered reverse transcription enzyme.

In some embodiments, the engineered reverse transcription enzyme comprises one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises two or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises three or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises four or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises five or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises six or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises seven or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises eight or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises nine or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises ten or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises eleven or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises twelve or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises thirteen or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises a E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3.

In some embodiments, the engineered reverse transcription enzyme comprises one or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises two or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises three or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises four or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises five or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises six or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises seven or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises eight or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603

W mutation, and an E607K mutation relative to an amino acid sequence of SEQ ID NO: 3.

In some embodiments, the engineered reverse transcription enzyme comprises nine or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises ten or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises eleven or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises twelve or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises thirteen or more mutations selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises a E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to an amino acid sequence of SEQ ID NO: 3.

In some embodiments, the engineered reverse transcription enzyme comprises (i) a truncation of at least 15 amino acids from the N terminus; (ii) a sequence of at least 5 histidine amino acids at the N terminus; (iii) a thrombin cleavage recognition site; and (iv) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (iv) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises (i) a truncation of at least 21 amino acids from the N terminus; (ii) a sequence of at least 5 histidine amino acids at the N terminus; (iii) a thrombin cleavage recognition site; and (iv) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (iv) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises (i) a truncation of at least 21 amino acids from the N terminus; (ii) a MRSSHHHHHHSSGLVPR (SEQ ID NO:8) amino acid sequence at the N terminus of the engineered reverse transcription enzyme; and (iii) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (iii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises (i) a truncation of at least 21 amino acids from the N terminus; (ii) a MRSSHHHHHHSSGLVPR (SEQ ID NO:8) amino acid sequence at the N terminus of the engineered reverse transcription enzyme; and (iii) an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (iii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises: (i) one or more mutations selected from the group consisting of an L139 mutation, a D200 mutation, a T330 mutation, a P448 mutation, a D449 mutation, a D524 mutation, and a L603 mutation relative to SEQ ID NO: 3; and (ii) one or more mutations selected from the group consisting of an E69 mutation, an E302 mutation, a T306 mutation, a W313 mutation, an L435 mutation, and an N454 mutation relative to SEQ ID NO: 3. In some instances, the mutations in (i) and (ii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises: (i) two or more mutations selected from the group consisting of an L139 mutation, a D200 mutation, a T330 mutation, a P448 mutation, a D449 mutation, a D524 mutation, and a L603 mutation relative to SEQ ID NO: 3; and (ii) two or more mutations selected from the group consisting of an E69 mutation, an E302 mutation, a T306 mutation, a W313 mutation, an L435 mutation, and an N454 mutation relative to SEQ ID NO: 3. In some instances, the mutations in (i) and (ii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises: (i) three or more mutations selected from the group consisting of an L139 mutation, a D200 mutation, a T330 mutation, a P448 mutation, a D449 mutation, a D524 mutation, and a L603 mutation relative to SEQ ID NO: 3; and (ii) three or more mutations selected from the group consisting of an E69 mutation, an E302 mutation, a T306 mutation, a W313 mutation, an L435 mutation, and an N454 mutation relative to SEQ ID NO: 3. In some instances, the mutations in (i) and (ii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises: (i) four or more mutations selected from the group consisting of an L139 mutation, a D200 mutation, a T330 mutation, a P448 mutation, a D449 mutation, a D524 mutation, and a L603 mutation relative to SEQ ID NO: 3; and (ii) four or more mutations selected from the group consisting of an E69 mutation, an E302 mutation, a T306 mutation, a W313 mutation, an L435 mutation, and an N454 mutation relative to SEQ ID NO: 3. In some instances, the mutations in (i) and (ii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises: (i) five or more mutations selected from the group consisting of an L139 mutation, a D200 mutation, a T330 mutation, a P448 mutation, a D449 mutation, a D524 mutation, and a L603 mutation relative to SEQ ID NO: 3; and (ii) five or more mutations selected from the group consisting of an E69 mutation, an E302 mutation, a T306 mutation, a W313 mutation, an L435 mutation, and an N454 mutation relative to SEQ ID NO: 3. In some instances, the mutations in (i) and (ii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme comprises: (i) six or more mutations selected from the group consisting of an L139 mutation, a D200 mutation, a T330 mutation, a P448 mutation, a D449 mutation, a D524 mutation, and a L603 mutation relative to SEQ ID NO: 3; and (ii) five or more mutations selected from the group consisting of an E69 mutation, an E302 mutation, a T306 mutation, a W313 mutation, an L435 mutation, and an N454 mutation relative to SEQ ID NO: 3. In some instances, the mutations in (i) and (ii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the engineered reverse transcription enzyme has a nucleotide sequence according to SEQ ID NO: 4. In some embodiments, the engineered reverse transcription enzyme has an amino acid sequence according to SEQ ID NO: 5.

In some embodiments, the engineered reverse transcription enzyme is engineered to have reduced and/or abolished RNase activity. In some embodiments, the engineered reverse transcription enzyme is engineered to have reduced and/or abolished RNase H activity. In some embodiments, the engineered reverse transcription enzyme engineered to have reduced and/or abolished RNase H activity comprises a D524 mutation. In some embodiments, the engineered reverse transcription enzyme engineered to have reduced and/or abolished RNase H activity comprises a D524A or a D524N mutation.

The engineered reverse transcription enzyme variants of the present disclosure have unexpectedly provided various improved benefits over other described and/or commercially available enzymes, such as improved thermal stability, processive reverse transcription, nontemplated base addition, and template switching ability. Furthermore, the engineered reverse transcription enzyme variants described herein also exhibit unexpectedly higher resistance to cell lysate (i.e., are less inhibited by cell lysate) than commercially available RT enzymes. Lastly, the engineered reverse transcription enzyme variants of the present disclosure have an unexpectedly greater ability to capture full-length transcripts (e.g., in T-cell receptor paired transcriptional profiling), as compared to other described and commercially available MMLV reverse transcription enzymes.

V. Nucleic Acid Sample Processing Using Engineered Reverse Transcription Enzymes Disclosed herein, in some embodiments, are methods for nucleic acid sample processing, comprising: providing a template ribonucleic acid (RNA) molecule in a reaction volume; and using an engineered reverse transcription enzyme to reverse transcribe said RNA molecule to a complementary DNA molecule, wherein said engineered reverse transcription enzyme comprises an amino acid sequence that is at least 80% identical to SEQ ID NO: 3, wherein said amino acid sequence comprises: (i) a truncation of at least 15 amino acids from the N-terminus relative to SEQ ID NO: 3; and (ii) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3. In some instances, the mutations in (ii) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the template nucleic acid molecule is ribonucleic acid (RNA) molecules. In some embodiments, the RNA molecules are messenger RNA (mRNA). In some embodiments, the engineered reverse transcription enzymes descried herein are used in a reaction volume is less than 1 nL. In some embodiments, the engineered reverse transcription enzymes descried herein are used in a reaction volume is less than 500 pL. In some embodiments, the reaction volume is contained within a partition. In some embodiments, the reaction volume is contained within a droplet in an emulsion. In some embodiments, the reaction volume is contained within a droplet emulsion having a reaction volume of less than 1 nL. In some embodiments, the reaction volume is contained within a droplet emulsion having a reaction volume of less than 500 pL. In some embodiments, the reaction volume is contained within a well. In some embodiments, the reaction volume is contained within a well having a reaction volume less than 1 nL. In some embodiments, the reaction volume is contained within a well. In some embodiments, the reaction volume is contained within a well having a reaction volume less than 500 pL. In some embodiments, the reaction volume is contained within a well in an array of wells having an extracted nucleic acid molecule, and wherein said template nucleic acid molecule is the extracted nucleic acid molecule. In some embodiments, the reaction volume is contained within a well in an array of wells having a cell comprising a template nucleic acid molecule, and wherein said template nucleic acid molecule is released from the cell.

In some embodiments, the reaction volume further comprises a particle comprising molecular tags (e.g., barcodes). In some embodiments, the particle is a gel bead. In some embodiments, said molecular tags are releasably attached to said gel bead. In some embodiments, the gel bead comprises a polyacrylamide polymer.

In some embodiments, a cross-section of a gel bead is less than about 100 μm. In some embodiments, a cross-section of a gel bead is less than about 60 μm. In some embodiments, a cross-section of a gel bead is less than about 50 μm. In some embodiments, a cross-section of a gel bead is less than about 40 μm. In some embodiments, a cross-section of a gel bead is less than about 100 μm, less than about 99 μm, less than about 98 μm, less than about 97 μm, less than about 96 μm, less than about 95 μm, less than about 94 μm, less than about 93 μm, less than about 92 μm, less than about 91 μm, less than about 90 μm, less than about 89 μm, less than about 88 μm, less than about 87 μm, less than about 86 μm, less than about 85 μm, less than about 84 μm, less than about 83 μm, less than about 82 μm, less than about 81 μm, less than about 80 μm, less than about 79 μm, less than about 78 μm, less than about 77 µm, less than about 76 µm, less than about 75 µm, less than about 74 µm, less than about 73 µm, less than about 72 µm, less than about 71 µm, less than about 70 µm, less than about 69 µm, less than about 68 µm, less than about 67 µm, less than about 66 µm, less than about 65 µm, less than about 64 µm, less than about 63 µm, less than about 62 µm, less than about 61 µm, or less than about 60 µm.

In some embodiments, the molecular tags (e.g., barcode oligonucleotides) include unique molecular identifiers (UMIs). In some embodiments, the UMIs comprise oligonucleotides. In some embodiments, the molecular tags are coupled to priming sequences. In some embodiments, each of said priming sequences comprises a random N-mer sequence. In some embodiments, the random N-mer sequence is complementary to a 3' sequence of said RNA molecules. In some embodiments, the priming sequence comprises a poly-dT sequence having a length of at least 5 bases. In some embodiments, the priming sequence comprises a poly-dT sequence having a length of at least 10 bases. In some embodiments, the priming sequence comprises a poly-dT sequence having a length of at least 5 bases, at least 6 bases, at least 7 bases, at least 8 bases, at least 9 bases, at least 10 bases.

In some embodiments, the reaction volume further comprises a cell and the template nucleic acid molecule is from said cell. In some embodiments, the reaction volume further comprises a plurality of cells and the template nucleic acid molecule is from said plurality of cells.

In some embodiments, the reverse transcription is initiated by hybridization of said priming sequences to said RNA molecules and is extended by the engineered reverse transcription enzyme in a template directed fashion. In some embodiments, the reverse transcription enzyme adds a plurality of non-template oligonucleotides upon reverse transcription of a ribonucleic acid molecule from said nucleic acid molecules. In some embodiments, the reverse transcription reaction produces single stranded complementary deoxyribonucleic acid (cDNA) molecules each having a molecular tag from said molecular tags on a 5' end thereof, followed by amplification of cDNA to produce a double stranded cDNA having the molecular tag on the 5' end and a 3' end of the double stranded cDNA.

In some embodiments, the methods for nucleic acid sample processing disclosed herein utilize the engineered reverse transcription enzymes described herein. In some embodiments, the methods for nucleic acid sample processing methods disclosed herein utilize engineered reverse transcription enzymes comprising an amino acid sequence that is at least 80% identical to an amino acid sequence of SEQ ID NO: 3, wherein said amino acid sequence is characterized by two or more of: (a) a truncation of at least 15 amino acids from an N terminus of said amino acid sequence; (b) a sequence of at least 5 histidine amino acids at said N terminus of said amino acid sequence; (c) a thrombin cleavage recognition site; and (d) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (d) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the methods for nucleic acid sample processing disclosed herein utilize engineered reverse transcription enzymes comprising an amino acid sequence that is at least 80% identical to an amino acid sequence of SEQ ID NO: 3, wherein said amino acid sequence is characterized by three or more of: (a) a truncation of at least 15 amino acids from an N terminus of said amino acid sequence; (b) a sequence of at least 5 histidine amino acids at said N terminus of said amino acid sequence; (c) a thrombin cleavage recognition site; and (d) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (d) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the methods for nucleic acid sample processing disclosed herein utilize engineered reverse transcription enzymes comprising an amino acid sequence that is at least 80% identical to an amino acid sequence of SEQ ID NO: 3, wherein said amino acid sequence is characterized by: (a) a truncation of at least 15 amino acids from an N terminus of said amino acid sequence; (b) a sequence of at least 5 histidine amino acids at said N terminus of said amino acid sequence; (c) a thrombin cleavage recognition site; and (d) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (d) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the nucleic acid sample processing methods disclosed herein utilize the engineered reverse transcription enzyme comprising an amino acid sequence that is at least 80% identical to an amino acid sequence of SEQ ID NO: 3, wherein said amino acid sequence comprises (a) a truncation of at least 21 amino acids from the N terminus; (b) a MRSSHHHHHHSSGLVPR (SEQ ID NO:8) amino acid sequence at the N terminus of the engineered reverse transcription enzyme; and (c) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607mutation relative to an amino acid sequence of SEQ ID NO: 3. In some instances, one or more mutations in (c) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the nucleic acid sample processing methods disclosed herein utilize an engineered reverse transcription enzymes having an amino acid sequence according to SEQ ID NO: 5.

VI. Nucleic Acid Sample Processing in Sub-Nanoliter Sized Droplets Using Engineered Reverse Transcription Enzymes Reverse transcription of mRNA from a single cell can be inhibited when the reaction volume is less than ~1 nL. To-date, there have been no published studies describing how to overcome this effect.

Disclosed herein, in some embodiments, are method for nucleic acid sample processing, comprising: (a) generating a plurality of droplets in an emulsion, wherein an individual droplet of said plurality of droplets comprises (i) a particle comprising molecular tags, and (ii) a cell having nucleic acid molecules, wherein a ratio of a volume of said particle to a volume of said individual droplet is less than 0.9, and wherein said volume of said individual droplet is less than 1 nanoliter; (b) using said molecular tags to barcode said nucleic acid molecules in a barcoding reaction that has a rate that deviates from a control rate of reaction by at most about 20%, which control rate of reaction is as determined for a control barcoding reaction in a control droplet having a control droplet volume of 1 nanoliter and comprising a single cell, thereby providing barcoded nucleic acid molecules; and (c) subjecting said barcoded nucleic acid molecule to nucleic acid sequencing to generate sequence information for at least a subset of said nucleic acid molecules.

In some embodiments, at least 1% of said plurality of droplets comprise cells. In some embodiments, at least 10% of said plurality of droplets comprise cells. In some embodiments, at least 20% of said plurality of droplets comprise cells. In some embodiments, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% of said plurality of droplets comprise cells. In some embodiments, an individual droplet in said plurality of droplets comprises a plurality of cells.

In some embodiments, an individual droplet in said plurality of droplets comprises a gel bead comprising molecular tags. In some embodiments, said molecular tags are releasably attached to said gel bead. In some embodiments, an individual droplet in said plurality of droplets comprises a gel bead comprising a polyacrylamide polymer. In some embodiments, an individual droplet in said plurality of droplets comprises a degradable gel bead. In some embodiments, said molecular tags include unique molecular identifiers (UMIs). In some embodiments, said UMIs comprise oligonucleotides.

In some embodiments, a cross-section of a gel bead is less than about 100 μm. In some embodiments, a cross-section of a gel bead is less than about 60 μm. In some embodiments, a cross-section of a gel bead is less than about 50 μm. In some embodiments, a cross-section of a gel bead is less than about 40 μm. In some embodiments, a cross-section of a gel bead is less than about 100 μm, less than about 99 μm, less than about 98 μm, less than about 97 μm, less than about 96 μm, less than about 95 μm, less than about 94 μm, less than about 93 μm, less than about 92 μm, less than about 91 μm, less than about 90 μm, less than about 89 μm, less than about 88 μm, less than about 87 μm, less than about 86 μm, less than about 85 μm, less than about 84 μm, less than about 83 μm, less than about 82 μm, less than about 81 μm, less than about 80 μm, less than about 79 μm, less than about 78 μm, less than about 77 μm, less than about 76 μm, less than about 75 μm, less than about 74 μm, less than about 73 μm, less than about 72 μm, less than about 71 μm, less than about 70 μm, less than about 69 μm, less than about 68 μm, less than about 67 μm, less than about 66 μm, less than about 65 μm, less than about 64 μm, less than about 63 μm, less than about 62 μm, less than about 61 μm, or less than about 60 μm.

In some embodiments, the ratio of a volume of said particle to a volume of said individual droplet is less than 0.9. In some embodiments, the ratio of a volume of said particle to a volume of said individual droplet is less than 0.8. In some embodiments, the ratio of a volume of said particle to a volume of said individual droplet is less than 0.7. In some embodiments, the ratio of a volume of said particle to a volume of said individual droplet is less than 0.2. In some embodiments, the ratio of a volume of said particle to a volume of said individual droplet is less than about 0.9, less than about 0.85, less than about 0.8, less than about 0.75, less than about 0.7, less than about 0.65, less than about 0.6, less than about 0.55, less than about 0.5, less than about 0.45, less than about 0.4, less than about 0.35, less than about 0.3, less than about 0.25, or less than about 0.2.

In some embodiments, the control barcoding reaction is a reverse transcription reaction conducted on nucleic acid molecules from said single cell. In some embodiments, the reverse transcription reaction is conducted in said control droplet using a reverse transcription enzyme having an amino acid sequence as set forth in SEQ ID NO: 3. In some embodiments, the reverse transcription reaction is conducted in said control droplet using a reverse transcription enzyme having a sequence as set forth in SEQ ID NO: 5. In some embodiments, the control droplet comprises an additional particle comprising molecular tags. In some embodiments, the barcoding reaction is an enzymatic reaction. In some embodiments, the barcoding reaction is a reverse transcription amplification reaction that generates complementary deoxyribonucleic acid (cDNA) molecules upon reverse transcription of ribonucleic acid (RNA) molecules of said cell. In some embodiments, the RNA molecules are released from said cell. In some embodiments, the RNA molecules are released from said cell by lysing said cell. In some embodiments, the RNA molecules are messenger RNA (mRNA).

In some embodiments, the molecular tags are coupled to priming sequences and the barcoding reaction is initiated by hybridization of said priming sequences to said RNA molecules. In some embodiments, each of said priming sequences comprises a random N-mer sequence. In some embodiments, said random N-mer sequence is complementary to a 3' sequence of a ribonucleic acid molecule of said cell. In some embodiments, said random N-mer sequence comprises a poly-dT sequence having a length of at least 5 bases. In some embodiments, said random N-mer sequence comprises a poly-dT sequence having a length of at least 10 bases. In some embodiments, the barcoding reaction is performed by extending each of said priming sequences in a template directed fashion using reagents for reverse transcription. In some embodiments, the reagents for reverse transcription comprise a reverse transcription enzyme, a buffer and a mixture of nucleotides. In some embodiments, the reverse transcription enzyme adds a plurality of non-template oligonucleotides upon reverse transcription of a ribonucleic acid molecule from said nucleic acid molecules. In some embodiments, the reverse transcription enzyme is an engineered reverse transcription enzyme as disclosed herein.

In some embodiments, the barcoding reaction produces single stranded complementary deoxyribonucleic acid (cDNA) molecules each having a molecular tag from said molecular tags on a 5' end thereof, followed by amplification of cDNA to produce a double stranded cDNA having the molecular tag on the 5' end and a 3' end of the double stranded cDNA.

In some embodiments, the barcoded nucleic acid molecules comprising the double stranded cDNA from an individual droplet are released prior to sequencing the barcoded nucleic acid molecules. In some embodiments, the barcoded nucleic acid molecules from said plurality of droplets are pooled prior to sequencing the barcoded nucleic acid molecules.

In some embodiments, the methods for nucleic acid sample processing disclosed herein wherein an individual droplet is less than 1 nanoliter, utilize the engineered reverse transcription enzymes described herein. In some embodiments, the methods for nucleic acid sample processing disclosed herein wherein an individual droplet is less than 1 nanoliter, utilize engineered reverse transcription enzymes comprising an amino acid sequence that is at least 80% identical to an amino acid sequence of SEQ ID NO: 3, wherein said amino acid sequence is characterized by two or more of: (a) a truncation of at least 15 amino acids from an N terminus of said amino acid sequence; (b) a sequence of at least 5 histidine amino acids at said N terminus of said amino acid sequence; (c) a thrombin cleavage recognition site; and (d) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607mutation relative to an amino acid sequence of SEQ ID NO: 3. In some instances, one or more mutations in (d) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the methods for nucleic acid sample processing disclosed herein wherein an individual droplet is less than 1 nanoliter, utilize engineered reverse transcription enzymes comprising an amino acid sequence that is at least 80% identical to an amino acid sequence of SEQ ID NO: 3, wherein said amino acid sequence is characterized by three or more of: (a) a truncation of at least 15 amino acids from an N terminus of said amino acid sequence; (b) a sequence of at least 5 histidine amino acids at said N terminus of said amino acid sequence; (c) a thrombin cleavage recognition site; and (d) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (d) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the methods for nucleic acid sample processing disclosed herein wherein an individual droplet is less than 1 nanoliter, utilize engineered reverse transcription enzymes comprising an amino acid sequence that is at least 80% identical to an amino acid sequence of SEQ ID NO: 3, wherein said amino acid sequence is characterized by: (a) a truncation of at least 15 amino acids from an N terminus of said amino acid sequence; (b) a sequence of at least 5 histidine amino acids at said N terminus of said amino acid sequence; (c) a thrombin cleavage recognition site; and (d) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607mutation relative to an amino acid sequence of SEQ ID NO: 3. In some instances, one or more mutations in (d) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the nucleic acid sample processing methods disclosed herein wherein an individual droplet is less than 1 nanoliter, utilize the engineered reverse transcription enzyme comprising an amino acid sequence that is at least 80% identical to an amino acid sequence of SEQ ID NO: 3, wherein said amino acid sequence comprises (a) a truncation of at least 21 amino acids from the N terminus; (b) a MRSSHHHHHHSSGLVPR (SEQ ID NO:8) amino acid sequence at the N terminus of the engineered reverse transcription enzyme; and (c) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to an amino acid sequence of SEQ ID NO: 3. In some instances, one or more mutations in (c) are selected from the group consisting of an E69K mutation, an L139P mutation, a D200N mutation, an E302R mutation, a T306K mutation, a W313F mutation, a T330P mutation, an L435G or L435K mutation, a P448A mutation, a D449G mutation, an N454K mutation, a D524N or D524A mutation, an L603 W mutation, and an E607K mutation relative to SEQ ID NO: 3.

In some embodiments, the nucleic acid sample processing methods disclosed herein wherein an individual droplet is less than 1 nanoliter, utilize an engineered reverse transcription enzymes having an amino acid sequence according to SEQ ID NO: 5.

VII. Devices and Systems

Also provided herein are the microfluidic devices used for partitioning the cells as described above. Such microfluidic devices can comprise channel networks for carrying out the partitioning process like those set forth in FIG. 1 and FIG. 2. Examples of particularly useful microfluidic devices are described in U.S. Provisional Patent Application No. 61/977,804, filed Apr. 4, 2014, and incorporated herein by reference in its entirety for all purposes. Briefly, these microfluidic devices can comprise channel networks, such as those described herein, for partitioning cells into separate partitions, and co-partitioning such cells with oligonucleotide barcode library members, e.g., disposed on beads. These channel networks can be disposed within a solid body, e.g., a glass, semiconductor or polymer body structure in which the channels are defined, where those channels communicate at their termini with reservoirs for receiving the various input fluids, and for the ultimate deposition of the partitioned cells, etc., from the output of the channel networks.

Also provided are systems that control flow of these fluids through the channel networks e.g., through applied pressure differentials, centrifugal force, electrokinetic pumping, capillary or gravity flow, or the like.

VIII. Kits

Also provided herein are kits for performing reverse transcription reaction, the kit comprising (a) an engineered reverse transcription enzyme of the present disclosure and (b) instructions for using said engineered reverse transcription enzyme to perform a reverse transcription reaction. The engineered reverse transcription enzyme may comprise (i) a truncation of at least 15 amino acids from the N-terminus relative to SEQ ID NO: 3; and (ii) one or more mutations selected from the group consisting of an E69 mutation, an L139 mutation, a D200 mutation, an E302 mutation, a T306 mutation, a W313 mutation, a T330 mutation, an L435 mutation, a P448 mutation, a D449 mutation, an N454 mutation, a D524 mutation, an L603 mutation, and an E607 mutation relative to SEQ ID NO: 3. The kit may also include suitable reaction buffers, dNTPs, one or more primers, one or more control reagents, or any other reagents disclosed for performing the methods of the present disclosure. The engineered reverse transcription enzyme, reaction buffer, and dNTPs may be provided separately or may be provided together in a master mix solution. In cases which the engineered reverse transcription enzyme, reaction buffer, and dNTPs are provided in a master mix, the master mix is present at a concentration at least two times the working concentration indicated in instructions for use in the reverse transcription reaction. In other cases, the master mix may be present at a concentration at least three times, at least four times, at least five times, at least six times, at least seven times, at least eight times, at least nine times, or at least ten times, the working concentration indicated. The primer in the kits may be a poly-dT primer, a random N-mer primer, or a target-specific primer.

The kits may further include one, two, three, four, five or more, up to all of partitioning fluids, including both aqueous buffers and non-aqueous partitioning fluids or oils, nucleic acid barcode libraries that are releasably associated with beads, as described herein, microfluidic devices, reagents for disrupting cells amplifying nucleic acids, and providing additional functional sequences on fragments of cellular nucleic acids or replicates thereof, as well as instructions for using any of the foregoing in the methods described herein.

Figure 17:
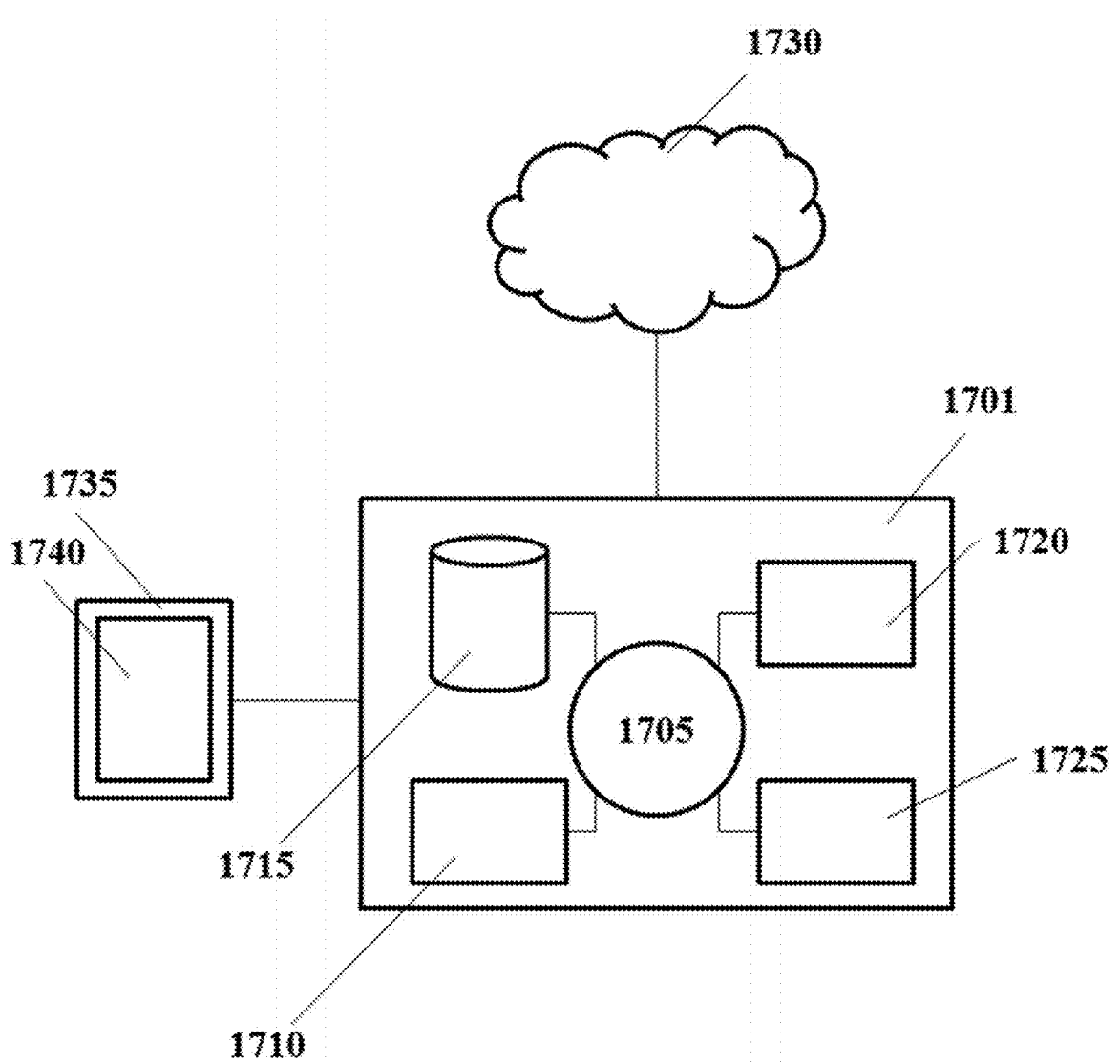
FIG. 17 shows an example computer control system that is programmed or otherwise configured to implement methods provided herein.

The instructions for using any of the methods are generally recorded on a suitable recording medium (e.g. printed on a substrate such as paper or plastic). As such, the instructions may be present in the kits as a package insert, in the labeling of the container of the kit or components thereof (i.e., associated with the packaging or subpackaging). In some cases, the instructions may be present as an electronic storage data file present on a suitable computer readable storage medium, e.g. CD-ROM, diskette, etc. In other cases, the actual instructions may not be present in the kit, but means for obtaining the instructions from a remote source, e.g. via the internet, may be provided. For example, a kit that includes a web address where the instructions may be viewed and/or from which the instructions may be downloaded. As with the instructions, this means for obtaining the instructions is recorded on a suitable substrate. IX. Computer Control Systems The present disclosure provides computer control systems that are programmed to implement methods of the disclosure. FIG. 17 shows a computer system 1701 that is programmed or otherwise configured to implement methods of the disclosure including nucleic acid sequencing methods, interpretation of nucleic acid sequencing data and analysis of cellular nucleic acids, such as RNA (e.g., mRNA), and characterization of cells from sequencing data. The computer system 1701 can be an electronic device of a user or a computer system that is remotely located with respect to the electronic device. The electronic device can be a mobile electronic device.

The computer system 1701 includes a central processing unit (CPU, also "processor" and "computer processor" herein) 1705, which can be a single core or multi core processor, or a plurality of processors for parallel processing. The computer system 1701 also includes memory or memory location 1710 (e.g., random-access memory, read-only memory, flash memory), electronic storage unit 1715 (e.g., hard disk), communication interface 1720 (e.g., network adapter) for communicating with one or more other systems, and peripheral devices 1725, such as cache, other memory, data storage and/or electronic display adapters. The memory 1710, storage unit 1715, interface 1720 and peripheral devices 1725 are in communication with the CPU 1705 through a communication bus (solid lines), such as a motherboard. The storage unit 1715 can be a data storage unit (or data repository) for storing data. The computer system 1701 can be operatively coupled to a computer network ("network") 1730 with the aid of the communication interface 1720. The network 1730 can be the Internet, an internet and/or extranet, or an intranet and/or extranet that is in communication with the Internet. The network 1730 in some cases is a telecommunication and/or data network. The network 1730 can include one or more computer servers, which can enable distributed computing, such as cloud computing. The network 1730, in some cases with the aid of the computer system 1701, can implement a peer-to-peer network, which may enable devices coupled to the computer system 1701 to behave as a client or a server.

The CPU 1705 can execute a sequence of machine-readable instructions, which can be embodied in a program or software. The instructions may be stored in a memory location, such as the memory 1710. The instructions can be directed to the CPU 1705, which can subsequently program or otherwise configure the CPU 1705 to implement methods of the present disclosure. Examples of operations performed by the CPU 1705 can include fetch, decode, execute, and writeback.

The CPU 1705 can be part of a circuit, such as an integrated circuit. One or more other components of the system 1701 can be included in the circuit. In some cases, the circuit is an application specific integrated circuit (ASIC).

The storage unit 1715 can store files, such as drivers, libraries and saved programs. The storage unit 1715 can store user data, e.g., user preferences and user programs. The computer system 1701 in some cases can include one or more additional data storage units that are external to the computer system 1701, such as located on a remote server that is in communication with the computer system 1701 through an intranet or the Internet.

The computer system 1701 can communicate with one or more remote computer systems through the network 1730. For instance, the computer system 1701 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1701 via the network 1730.

Methods as described herein can be implemented by way of machine (e.g., computer processor) executable code stored on an electronic storage location of the computer system 1701, such as, for example, on the memory 1710 or electronic storage unit 1715. The machine executable or machine readable code can be provided in the form of software. During use, the code can be executed by the processor 1705. In some cases, the code can be retrieved from the storage unit 1715 and stored on the memory 1710 for ready access by the processor 1705. In some situations, the electronic storage unit 1715 can be precluded, and machine-executable instructions are stored on memory 1710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1701 can include or be in communication with an electronic display 1735 that comprises a user interface (UI) 1740 for providing, for example, results of nucleic acid sequencing, analysis of nucleic acid sequencing data, characterization of nucleic acid sequencing samples, cell characterizations, etc. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1705. The algorithm can, for example, initiate nucleic acid sequencing, process nucleic acid sequencing data, interpret nucleic acid sequencing results, characterize nucleic acid samples, characterize cells, etc.

EXAMPLES

Example 1. Cellular RNA Analysis Using Emulsions

In an example, reverse transcription with template switching and cDNA amplification (via PCR) is performed in emulsion droplets with operations as shown in FIG. 9A. The reaction mixture that is partitioned for reverse transcription and cDNA amplification (via PCR) includes 1,000 cells or 10,000 cells or 10 ng of RNA, beads bearing barcoded oligonucleotides/0.2% Tx-100/5× Kapa buffer, 2× Kapa HS HiFi Ready Mix, 4 μM switch oligo, and Smartscribe. Where cells are present, the mixture is partitioned such that a majority or all of the droplets comprise a single cell and single bead. The cells are lysed while the barcoded oligonucleotides are released from the bead, and the poly-dT segment of the barcoded oligonucleotide hybridizes to the poly-A tail of mRNA that is released from the cell as in operation 950. The poly-dT segment is extended in a reverse transcription reaction as in operation 952 and the cDNA transcript is amplified as in operation 954. The thermal cycling conditions are 42° C. for 130 minutes; 98° C. for 2 min; and 35 cycles of the following 98° C. for 15 sec, 60° C. for 20 sec, and 72° C. for 6 min. Following thermal cycling, the emulsion is broken and the transcripts are purified with Dynabeads and 0.6×SPRI as in operation 956.

Figure 13A:
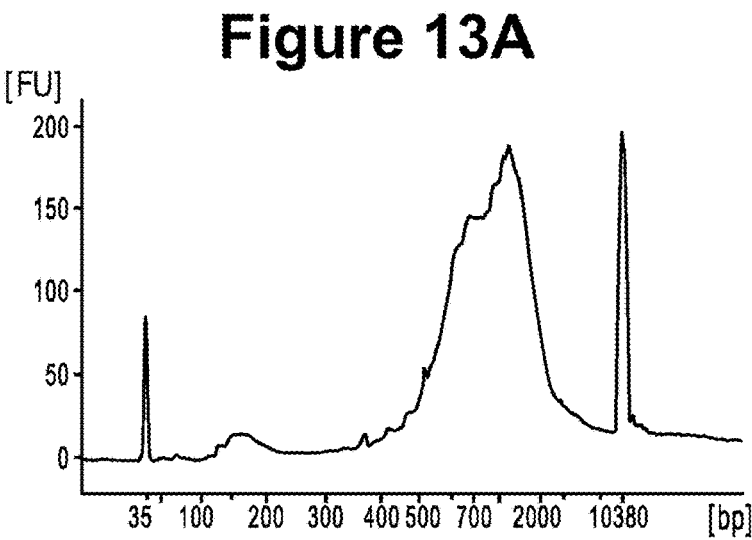
FIG. 13A-FIG. 13C provides illustrations of example yields from template switch reverse transcription and PCR in partitions.
Figure 13B:
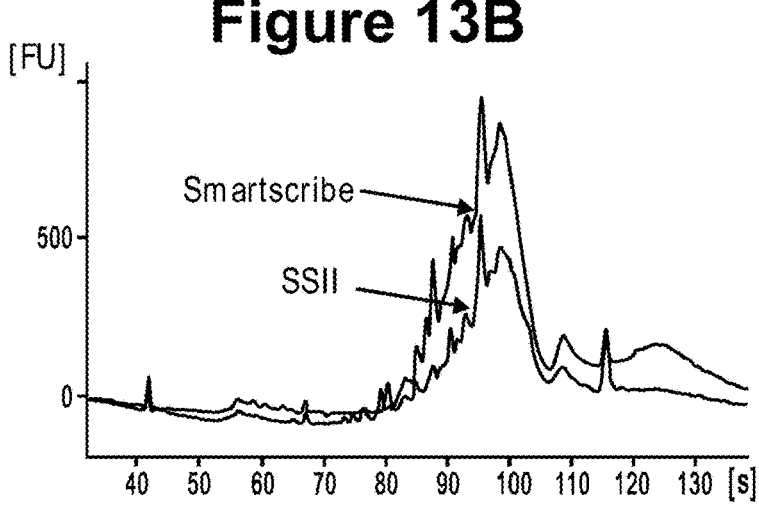
Figure 13C:
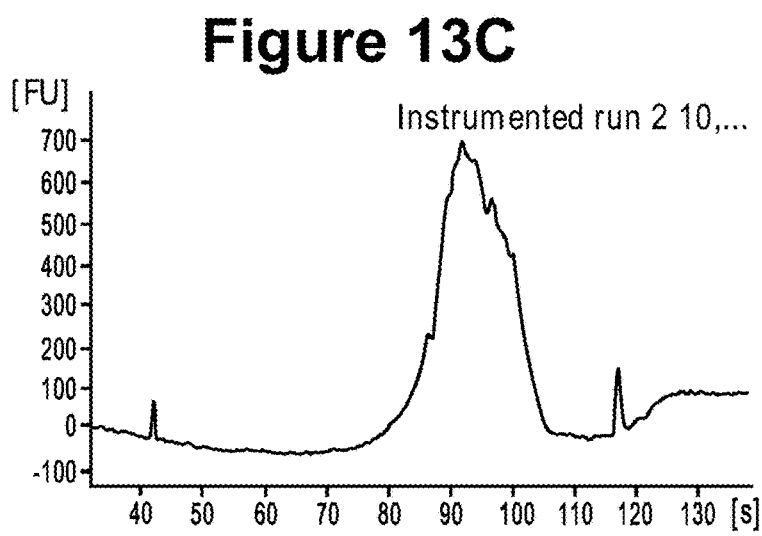

The yield from template switch reverse transcription and PCR in emulsions is shown for 1,000 cells in FIG. 13A and 10,000 cells in FIG. 13C and 10 ng of RNA in FIG. 13B (Smartscribe line). The cDNA transcripts from RT and PCR performed in emulsions for 10 ng RNA is sheared and ligated to functional sequences, cleaned up with 0.8×SPRI, and is further amplified by PCR as in operation 958. The amplification product is cleaned up with 0.8×SPRI. The yield from this processing is shown in FIG. 13B (SSII line).

Example 2. Cellular RNA Analysis Using Emulsions

Figure 14A:
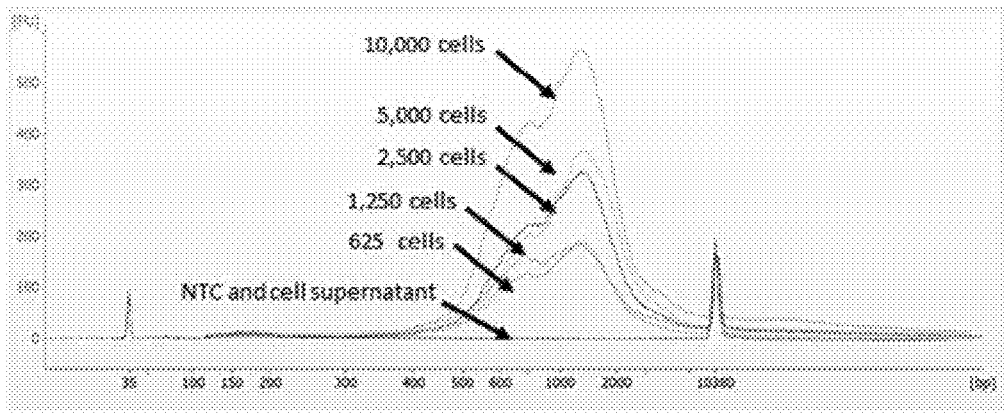
FIG. 14A-FIG. 14B provides illustrations of example yields from reverse transcription and cDNA amplification in partitions with various cell numbers.
Figure 14B:
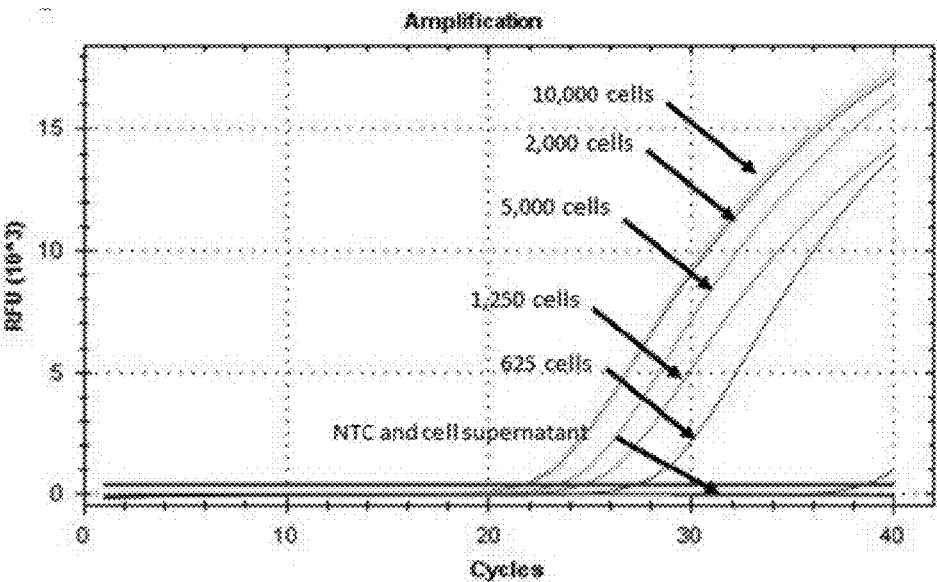

In another example, reverse transcription with template switching and cDNA amplification (via PCR) is performed in emulsion droplets with operations as shown in FIG. 9A. The reaction mixture that is partitioned for reverse transcription and cDNA amplification (via PCR) includes Jurkat cells, beads bearing barcoded oligonucleotides/0.2% Triton X-100/5× Kapa buffer, 2× Kapa HS HiFi Ready Mix, 4 μM switch oligo, and Smartscribe. The mixture is partitioned such that a majority or all of the droplets comprise a single cell and single bead. The cells are lysed while the barcoded oligonucleotides are released from the bead, and the poly-dT segment of the barcoded oligonucleotide hybridizes to the poly-A tail of mRNA that is released from the cell as in operation 950. The poly-dT segment is extended in a reverse transcription reaction as in operation 952 and the cDNA transcript is amplified as in operation 954. The thermal cycling conditions are 42° C. for 130 minutes; 98° C. for 2 min; and 35 cycles of the following 98° C. for 15 sec, 60° C. for 20 sec, and 72° C. for 6 min. Following thermal cycling, the emulsion is broken and the transcripts are cleaned-up with Dynabeads and 0.6×SPRI as in operation 956. The yield from reactions with various cell numbers (625 cells, 1,250 cells, 2,500 cells, 5,000 cells, and 10,000 cells) is shown in FIG. 14A. These yields are confirmed with GADPH qPCR assay results shown in FIG. 14B.

Example 3. RNA Analysis Using Emulsions

Figure 15:
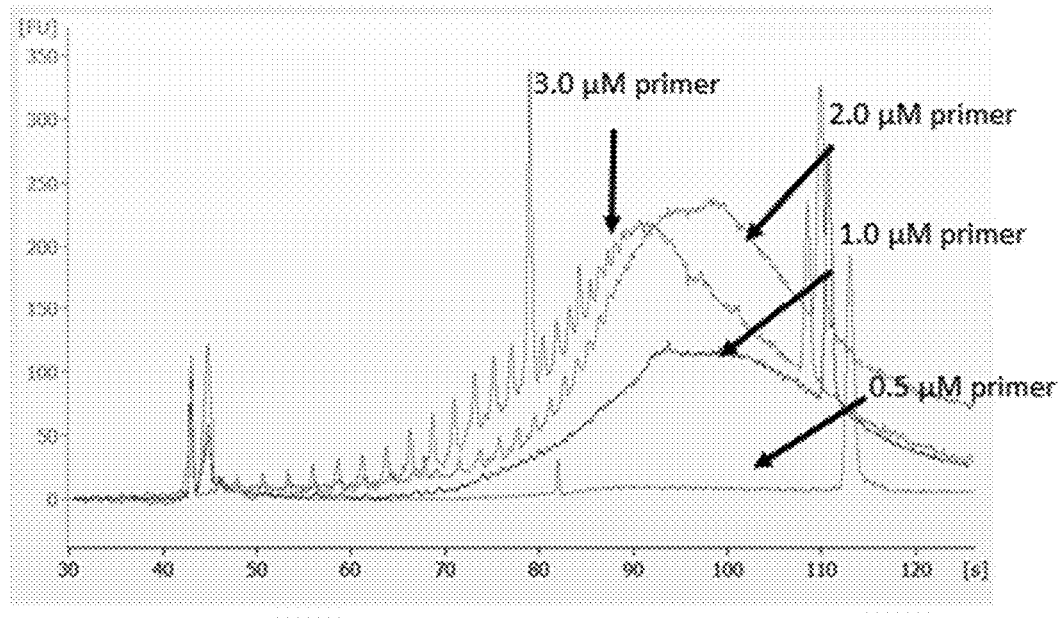
FIG. 15 provides an illustration of example yields from cDNA synthesis and real-time quantitative PCR at various input cell concentrations and also the effect of varying primer concentration on yield at a fixed cell input concentration.

In another example, reverse transcription is performed in emulsion droplets and cDNA amplification is performed in bulk in a manner similar to that as shown in FIG. 9C. The reaction mixture that is partitioned for reverse transcription includes beads bearing barcoded oligonucleotides, 10 ng Jurkat RNA (e.g., Jurkat mRNA), 5× First-Strand buffer, and Smartscribe. The barcoded oligonucleotides are released from the bead, and the poly-dT segment of the barcoded oligonucleotide hybridizes to the poly-A tail of the RNA as in operation 961. The poly-dT segment is extended in a reverse transcription reaction as in operation 963. The thermal cycling conditions for reverse transcription are one cycle at 42° C. for 2 hours and one cycle at 70° C. for 10 min. Following thermal cycling, the emulsion is broken and RNA and cDNA transcripts are denatured as in operation 962. A second strand is then synthesized by primer extension with a primer having a biotin tag as in operation 964. The reaction conditions for this primer extension include cDNA transcript as the first strand and biotinylated extension primer ranging in concentration from 0.5-3.0 μM. The thermal cycling conditions are one cycle at 98° C. for 3 min and one cycle of 98° C. for 15 sec, 60° C. for 20 sec, and 72° C. for 30 min. Following primer extension, the second strand is pulled down with Dynabeads MyOne Streptavidin C1 and T1, and cleaned-up with Agilent SureSelect XT buffers. The second strand is pre-amplified via PCR as in operation 965 with the following cycling conditions—one cycle at 98° C. for 3 min and one cycle of 98° C. for 15 sec, 60° C. for 20 sec, and 72° C. for 30 min. The yield for various concentrations of biotinylated primer (0.5 μM, 1.0 μM, 2.0 μM, and 3.0 μM) is shown in FIG. 15.

Example 4. RNA Analysis Using Emulsions

Figure 16:
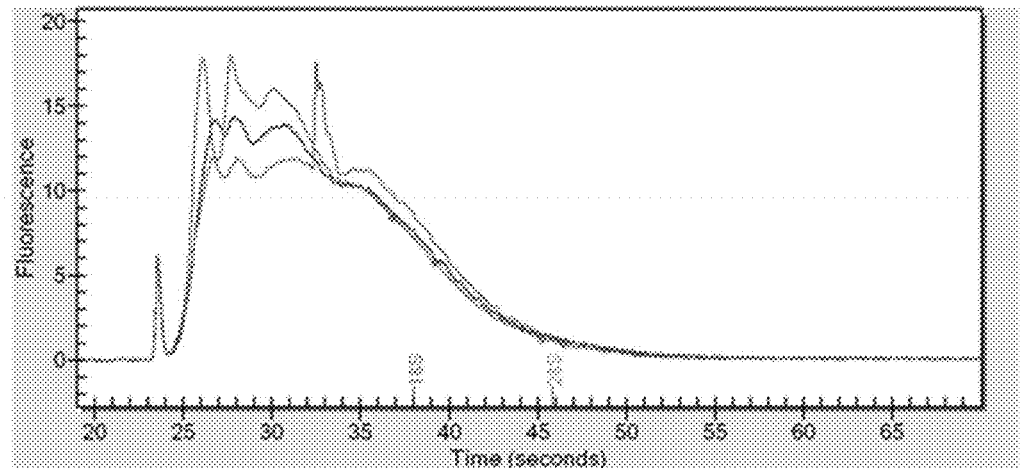
FIG. 16 provides an illustration of example yields from in vitro transcription.

In another example, in vitro transcription by T7 polymerase is used to produce RNA transcripts as shown in FIG. 10. The mixture that is partitioned for reverse transcription includes beads bearing barcoded oligonucleotides which also include a T7 RNA polymerase promoter sequence, 10 ng human RNA (e.g., human mRNA), 5× First-Strand buffer, and Smartscribe. The mixture is partitioned such that a majority or all of the droplets comprise a single bead. The barcoded oligonucleotides are released from the bead, and the poly-dT segment of the barcoded oligonucleotide hybridizes to the poly-A tail of the RNA as in operation 1050. The poly-dT segment is extended in a reverse transcription reaction as in operation 1052. The thermal cycling conditions are one cycle at 42° C. for 2 hours and one cycle at 70° C. for 10 min. Following thermal cycling, the emulsion is broken and the remaining operations are performed in bulk. A second strand is then synthesized by primer extension as in operation 1054. The reaction conditions for this primer extension include cDNA transcript as template and extension primer. The thermal cycling conditions are one cycle at 98° C. for 3 min and one cycle of 98° C. for 15 sec, 60° C. for 20 sec, and 72° C. for 30 min. Following this primer extension, the second strand is purified with 0.6× SPRI. As in operation 1056, in vitro transcription is then performed to produce RNA transcripts. In vitro transcription is performed overnight, and the transcripts are purified with 0.6×SPRI. The RNA yields from in vitro transcription are shown in FIG. 16.

Example 5. RNA Analysis of Droplets of Less than 1 nL

A clear body of evidence shows that reverse transcription of mRNA from a single cell is inhibited from an unknown component(s) present in the cell lysate when the reaction volume is less than ~1 nL. To overcome this inhibition and facilitate the utilization of smaller reaction volumes for increased sample throughput, engineered MMLV RT enzymes as disclosed herein were generated and tested in droplets containing picoliter-sized reaction volumes. One such engineered MMLV RT enzyme, enzyme 42B (SEQ ID NO: 5), demonstrated reduced inhibition of reverse transcription in a 350 pL reaction volume as compared to a commercially available mutant MMLV RT enzyme (CA-MMLV).

TABLE 2

| Sample Conditions | | | |
| --- | --- | --- | --- |
| Condition | Sample | Droplet Volume | Enzyme |
| 1 | GEM-U | 1.1 nL | CA-MMLV (Control) |
| 2 | GEM-L | 350 pL | CA-MMLV |
| 3 | GEM-L | 350 pL | 42B |

Figure 18:
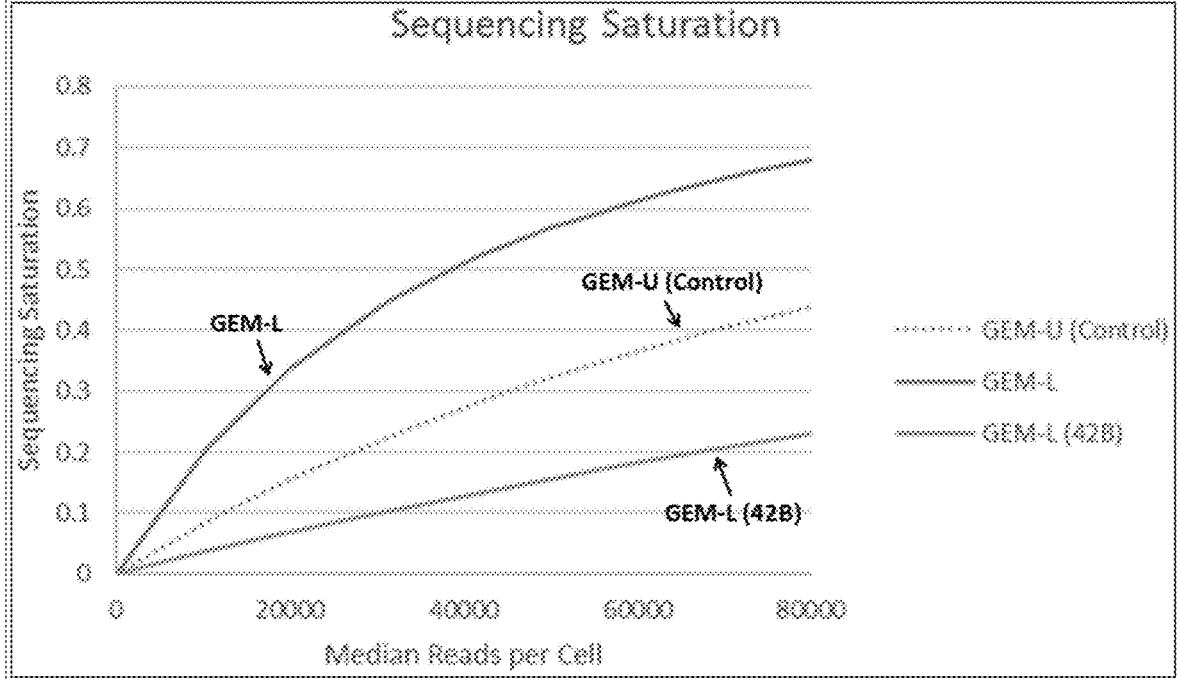
FIG. 18 provides an illustration of example sequencing saturation results in picoliter-sized droplets containing an engineered RT enzyme compared to a commercially-available counterpart.
Figure 19:
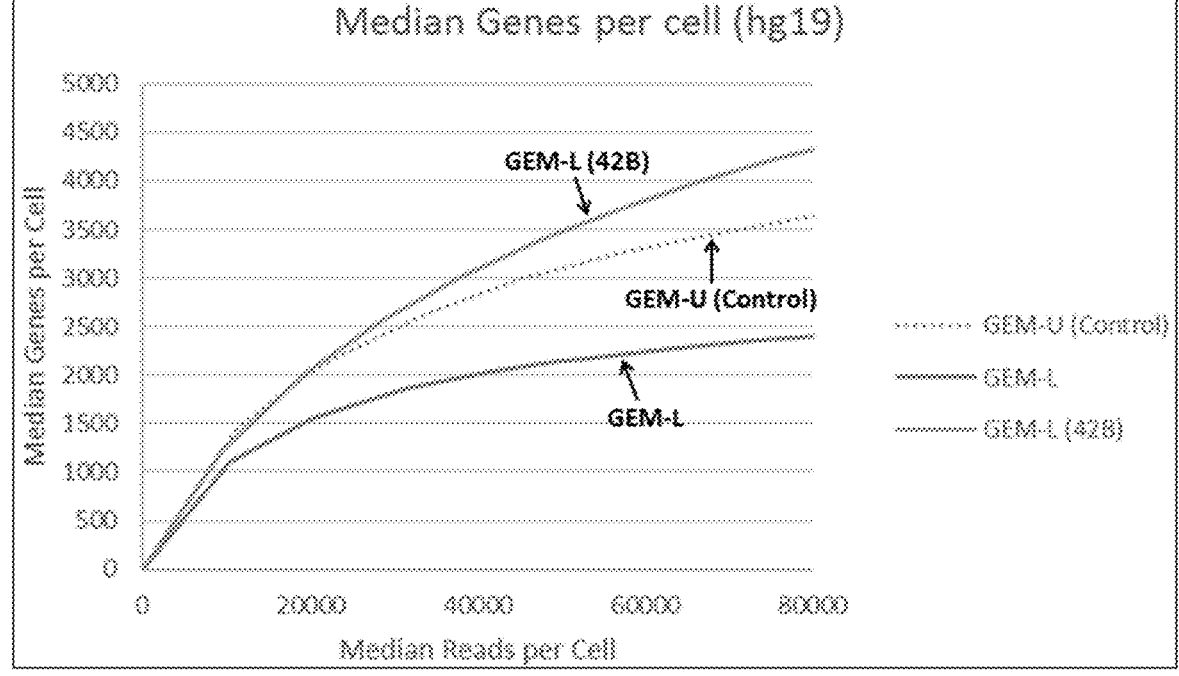
FIG. 19 provides an illustration of example median genes per cell (human genome hg19) obtained from cDNA libraries prepared in picoliter-sized droplets containing an engineered RT enzyme compared to a commercially available counterpart.
Figure 20:
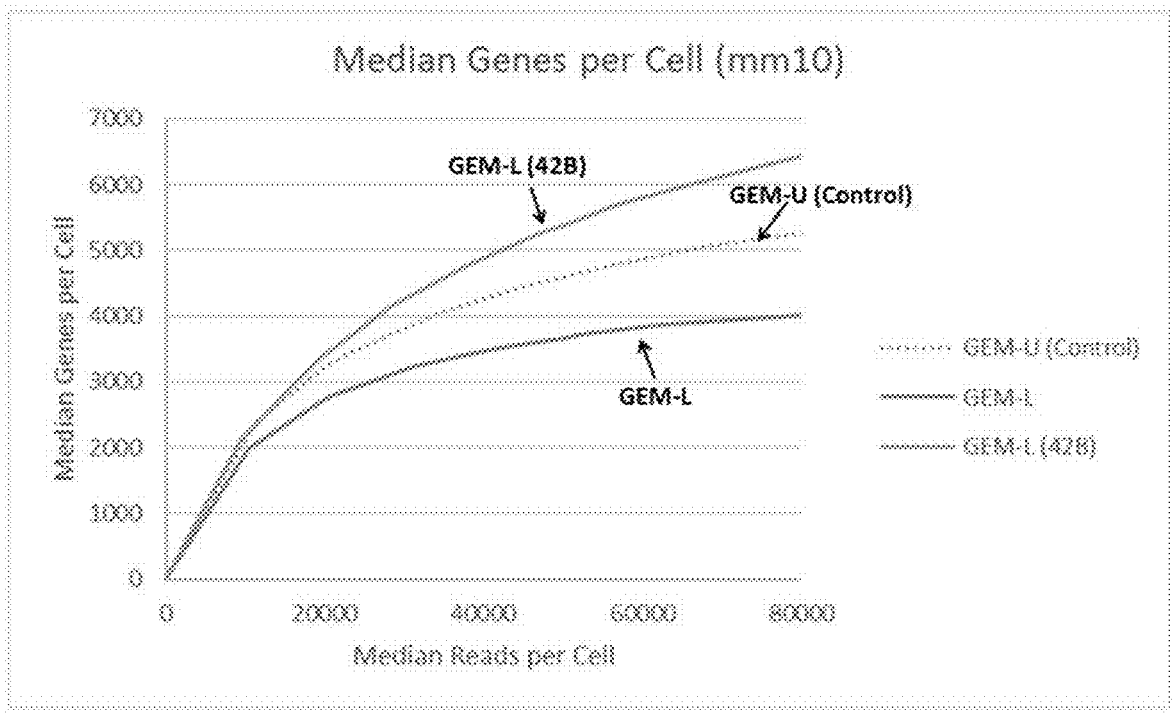
FIG. 20 provides an illustration of example median genes per cell (mouse genome mm10) obtained from cDNA libraries prepared in picoliter-sized droplets containing an engineered RT enzyme compared to a commercially available counterpart.

As shown in FIG. 18-FIG. 20 and Table 3, the RT reaction was inhibited when using the commercially available mutant MMLV RT enzyme in a 350 pL droplet volume. Conversely, no inhibition was observed when using enzyme 42B in a 350 pL droplet volume indicating that enzyme 42B is more tolerant to cell lysate inhibition in droplets <1 nL in volume and provided a greater library complexity as compared to a commercially available mutant MMLV RT enzyme.

TABLE 3

| | Specification | 1.1 nL (GEM-U) CA-MMLV | 350 pL (GEM-L) CA-MMLV | 350 pL (GEM-L) 42B |
|---|---|---|---|---|
| Comparative Results in 350 pL droplets | | | | |
| Down Sampled Metrics | | | | |
| hg19 Median Genes per Cell (50K RRPC) | | 4,598 | 3,671 | 5,386 |
| hg19 Median UMI Counts per Cell (50K RRPC) | | 24,473 | 13,481 | 21,478 |
| mm10 Median Genes per Cell (50K RRPC) | | 3,100 | 2,150 | 3,484 |
| mm10 Median UMI Counts per Cell (50K RRPC) | | 12,268 | 5,959 | 11,958 |
| Mean UMI Count Purity (50K RRPC) | ≥98% | 98.50% | 99.30% | 99.40% |
| cDNA PCR Duplication Rate (50K RRPC) | | 32.20% | 56.80% | 15.60% |
| Multiplet Rate (per 1000 Cells) | ≤2.0% | | | |
| Mapping Rate Metrics | | | | |
| Fraction of Reads Useable | | 56.40% | 46.00% | 43.50% |
| Fraction of Reads with Primer or Homopolymer Sequence | | 3.50% | 4.50% | 7.60% |
| Fraction of rRNA Reads | | 0.10% | 0.10% | 0.50% |
| Fraction of mtRNA Reads | | 4.30% | 3.70% | 6.60% |
| Fraction of Reads Mapping Confidently to the Transcriptome | ≥50.0% | 68.00% | 61.50% | 52.70% |
| Human (hg19) Reads Confidently Mapped to | | | | |
| Transcriptome | | 39.00% | 36.30% | 31.20% |
| Exonic Regions | | 41.60% | 39.10% | 33.80% |
| Intronic Regions | | 8.90% | 12.80% | 18.00% |
| Intergenic Regions | | 2.40% | 3.00% | 4.80% |
| Mouse (mm10) Reads Confidently Mapped to | | | | |
| Transcriptome | | 29.00% | 25.20% | 21.50% |
| Exonic Regions | | 30.30% | 26.50% | 22.50% |
| Intronic Regions | | 5.40% | 7.50% | 7.90% |
| Intergenic Regions | | 1.50% | 1.80% | 1.90% |

Example 6. Analysis of an Engineered MMLV RT Enzyme Variant in Single Cell Transcriptional Profiling Cells were harvested and washed to remove contaminants. Droplets comprising a single cell, a single gel bead, and RT Master Mix were generated as disclosed herein.

Barcoded gel beads containing primers were released from the gel bead and mixed with cell lysate and Master Mix to generate produce barcoded, full-length cDNA ready for next-generation sequencing. Barcoded cDNA was generated using either an engineered MMLV RT enzyme as disclosed herein (e.g., enzyme 42B) or a commercially available mutant MMLV RT enzyme (CA-MMLV).

TABLE 4

| Sample | CA-MMLV Results CA-MMLV Enzyme | | | |
|---|---|---|---|---|
| | 10 U/μL | 15 U/μL | 20 U/μL | 25 U/μL |
| Sample ID | 27325 | 27326 | 27327 | 27328 |
| hg19 Median UMI counts per cell (20K RRPC) | 10,478 | 10,738 | 10,749 | 10,577 |
| mm10 Median UMI counts per cell (20K RRPC) | 6,683 | 6,982 | 6,893 | 6,859 |
| Fraction UMI counts for genes <500 nt | 0.8% | 1.0% | 1.1% | 1.1% |
| Fraction UMI counts for genes 500-1000 nt | 29.4% | 30.9% | 32.4% | 32.7% |
| Fraction UMI counts for genes 1000-1500 nt | 29.0% | 28.7% | 28.3% | 28.5% |
| Fraction UMI counts for genes >1500 nt | 40.3% | 39.4% | 38.2% | 37.7% |

TABLE 4-continued

| | 10 U/μL | 15 U/μL | 20 U/μL | 25 U/μL |
|---|---|---|---|---|
| CA-MMLV Results CA-MMLV Enzyme | | | | |
| Sample | | | | |
| Fraction ribosomal protein UMI counts | 26.4% | 28.5% | 29.8% | 30.0% |
| Fraction mitochondrial UMI counts | 2.1% | 2.1% | 2.1% | 1.9% |

TABLE 5

| | 10 U/μL | 15 U/μL | 20 U/μL | 25 U/μL |
|---|---|---|---|---|
| CA-MMLV Results CA-MMLV Enzyme | | | | |
| Sample | | | | |
| Sample ID | 27325 | 27326 | 27327 | 27328 |
| Mean Reads per Cell | 51,623 | 87,837 | 93,780 | 57,701 |
| hg19 Fraction of Reads in Cells | 80.2% | 82.6% | 81.1% | 84.4% |
| mm10 Fraction of Reads in Cells | 84.6% | 85.4% | 85.2% | 86.6% |
| Fraction of Reads Useable | 54.1% | 54.2% | 53.5% | 58.8% |
| Fraction of mtRNA reads | 1.9% | 1.9% | 2.0% | 1.9% |
| Fraction of reads with primer or homopolymer sequence | 2.2% | 2.1% | 2.0% | 2.1% |
| cDNA PCR Duplication (20K RRPC) | 20.2% | 17.2% | 15.4% | 15.1% |
| hg19 Median genes per cell (20K RRPC) | 3,050 | 3,035 | 3,010 | 2,939 |
| mm10 Median genes per cell (20K RRPC) | 2,257 | 2,255 | 2,190 | 2,186 |

TABLE 6

| | 6 U/μL | 9 U/μL | 12 U/μL | 15 U/μL |
|---|---|---|---|---|
| Engineered RT Mutant Results Mutant 42B | | | | |
| Sample | | | | |
| Sample ID | 27329 | 27330 | 27331 | 27332 |
| Mean Reads per Cell | 55,525 | 53,843 | 28,539 | 47,768 |
| hg19 Fraction of Reads in Cells | 89.4% | 87.3% | 90.1% | 91.5% |
| mm10 Fraction of Reads in Cells | 90.5% | 90.7% | 90.8% | 91.6% |
| Fraction of Reads Useable | 60.2% | 58.6% | 59.2% | 58.8% |
| Fraction of mtRNA reads | 8.5% | 7.9% | 7.7% | 9.1% |
| Fraction of reads with primer or homopolymer sequence | 1.6% | 1.6% | 1.6% | 1.5% |
| cDNA PCR Duplication (20K RRPC) | 36.5% | 28.6% | 26.0% | 19.3% |
| hg19 Median genes per cell (20K RRPC) | 2,985 | 3,060 | 3,148 | 3,176 |
| mm10 Median genes per cell (20K RRPC) | 2,167 | 2,341 | 2,367 | 2,242 |

TABLE 7

| | | | | |
|---|---|---|---|---|
| | Engineered RT Mutant Results Mutant 42B | | | |
| Sample | ~6 U/µL | ~9 U/µL | ~12 U/µL | ~15 U/µL |
| Sample ID | 27329 | 27330 | 27331 | 27332 |
| hg19 Median UMI counts per cell (20K RRPC) | 8,742 | 9,484 | 10,070 | 11,253 |
| mm10 Median UMI counts per cell (20K RRPC) | 5,322 | 6,185 | 6,312 | 6,630 |
| Fraction UMI counts for genes <500 nt | 0.5% | 0.6% | 0.5% | 0.9% |
| Fraction UMI counts for genes 500-1000 nt | 23.6% | 24.4% | 24.2% | 30.1% |
| Fraction UMI counts for genes 1000-1500 nt | 26.1% | 26.7% | 27.2% | 27.7% |
| Fraction UMI counts for genes >1500 nt | 49.8% | 28.4% | 48.1% | 41.4% |
| Fraction ribosomal protein UMI counts | 17.3% | 18.5% | 18.5% | 22.3% |
| Fraction mitochondrial UMI counts | 9.4% | 8.7% | 8.1% | 9.7% |

As seen in Tables 4-7, while engineered RT enzyme 42B results in a roughly equal library complexity and a roughly equal duplication rate at a given sequencing depth, reactions including enzyme 42B generate a library biased toward longer genes.

Example 7. Analysis of an Engineered MMLV RT Enzyme Variant in Single Cell Full-Length Paired V(D)J Transcriptional Profiling Lymphocytes were harvested and partitioned into a droplet emulsion such that droplets were generated comprising a single cell, a single gel bead comprising barcode oligonucleotides, and reagents for reverse transcription as described elsewhere herein. Barcoded cDNA was generated (see, e.g., FIG. 11 and accompanying text) using either engineered MMLV RT enzyme 42B (SEQ ID NO: 5) or a comparable, commercially available MMLV RT enzyme (CA-MMLV) to analyze the performance of enzyme 42B in the characterization of lymphocyte T-cell receptor (TCR) alpha and beta chains.

TABLE 8

| | | |
|---|---|---|
| | Productive Pairs per Targeted Cell Recovery | |
| Targeted Cell Recovery | RT Enzyme | Cells with Productive V-J Spanning (TRA, TRB) Pair |
| 1K T-cells | CA-MMLV | 24.5% |
| | 42B | 39.4% |
| 6k T-cells | CA-MMLV | 24.0% |
| | 42B | 44.7% |

Figure 21:
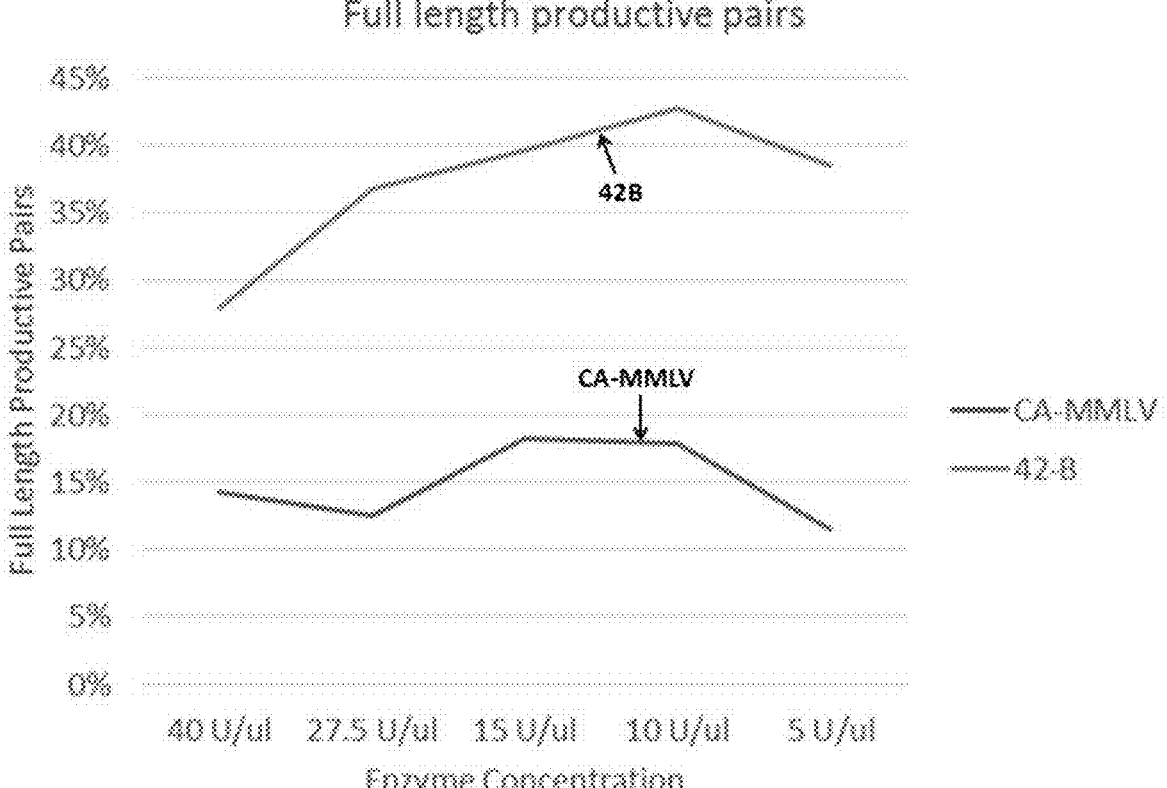
FIG. 21 shows an exemplary productive pair comparison from a TCR transcriptional profiling prepared from droplets containing an engineered RT enzyme compared to a commercially available counterpart.

As seen Table 8, enzyme 42B demonstrated improved sensitivity to low cell count compared to CA-MMLV. Additionally, as seen in FIG. 21 and FIG. 22, enzyme 42B-containing samples exhibited a higher fraction of cells with full-length productive TCR-alpha and TCR-beta pairs while exhibiting lower partial pR1 concatemer side products. Overall, use of enzyme 42B resulted in greatly enhanced TCR assembly, due to greater number of TCR mRNA molecules detected and reduced background of primer concatemers.

Example 8. Analysis of an Engineered MMLV RT Enzyme Variant in Transcriptional Profiling Human PBMCs were harvested and partitioned into a droplet emulsion such that droplets were generated comprising a single cell, a single gel bead comprising barcode oligonucleotides, and reagents for reverse transcription as previously described herein. Barcoded cDNA was generated using either engineered MMLV RT enzyme 42B (SEQ ID NO: 5) or a comparable, commercially available MMLV RT enzyme (CA-MMLV) to analyze the performance of enzyme 42B in both a 3' reverse transcription assay (see, e.g., FIG. 9A and accompanying text) and in a 5' reverse transcription assay (see, e.g., FIG. 11 and accompanying text). Gel beads comprising a releasable barcoded oligonucleotide comprising a poly-dT sequence (3' assay) or a template switching sequence (5' assay) were used to generate full-length cDNA, which was then pooled and processed as described elsewhere herein for next-generation sequencing and analysis.

TABLE 9

| | | | | |
|---|---|---|---|---|
| | Comparison between a CA-MMLV and Mutant Enzyme 42B in a 3'assay | | | |
| | CA-MMLV Enzyme | | Mutant 42B Enzyme | |
| Description | SC3'v2 - Maxima - Rep 1 | SC3'v2 - Maxima - Rep 2 | SC3'v2 - 42B - Rep 1 | SC3'v2 - 42B - Rep 2 |
| Cell Load | 1000 | 1000 | 1000 | 1000 |
| Mean Reads per Cell | 257,168 | 288,724 | 260,854 | 256,403 |

TABLE 9-continued

| Comparison between a CA-MMLV and Mutant Enzyme 42B in a 3'assay | | | | |
|---|---|---|---|---|
| | CA-MMLV Enzyme | | Mutant 42B Enzyme | |
| Valid Barcodes | 98.30% | 98.30% | 98.30% | 98.20% |
| Reads Mapped Confidently to Transcriptome | 59.20% | 59.80% | 52.50% | 52.70% |
| Reads Mapped Confidently to Intergenic Regions | 4.20% | 4.00% | 4.70% | 4.70% |
| Reads Mapped Confidently to Intronic Regions | 21.30% | 20.80% | 25.60% | 25.50% |
| Reads Mapped Confidently to Exonic Regions | 62.30% | 63.00% | 55.00% | 55.20% |
| Reads Mapped Antisense to Gene | 1.10% | 1.00% | 0.90% | 0.90% |
| Fraction rRNA reads | 0.10% | 0.10% | 0.10% | 0.10% |
| Fraction mtRNA reads | 2.40% | 2.30% | 6.30% | 6.60% |
| Fraction reads unmapped | 9.20% | 9.30% | 12.00% | 11.90% |
| Median genes per cell (50k raw reads per cell) | 987 | 1,016 | 1,311 | 1,343 |
| Median genes per cell (50k mapped cell-reads per cell) | 1,034 | 1,064 | 1,392 | 1,428 |
| Median UMI counts per cell (50k raw reads per cell) | 2,914 | 3,042 | 3,530 | 3,591 |
| Median UMI counts per cell (50k mapped cell-reads per cell) | 3,057 | 3,182 | 3,783 | 3,830 |
| Total genes detected >1500 nt (50k raw reads per cell) | 11,411 | 11,359 | 11,803 | 11,880 |
| Total genes detected >1500 nt (50k mapped cell-reads per cell) | 11,587 | 11,542 | 12,045 | 12,110 |
| Fraction UMI counts for genes <500 nt | 4.00% | 3.60% | 3.20% | 3.40% |
| Fraction UMI counts for genes 500-1000 nt | 31.70% | 31.70% | 25.00% | 25.00% |
| Fraction UMI counts for genes 1000-1500 nt | 24.90% | 24.80% | 20.00% | 20.20% |
| Fraction UMI counts for genes >1500 nt | 39.40% | 40.00% | 51.80% | 51.50% |
| Fraction ribosomal protein UMI counts | 37.80% | 37.80% | 23.20% | 22.80% |

TABLE 10

| Comparison between a CA-MMLV and Mutant Enzyme 42B in a 5'assay | | | | |
|---|---|---|---|---|
| | CA-MMLV Enzyme | | Mutant 42B Enzyme | |
| Sample ID | 41621 | 41622 | 41623 | 41624 |
| Description | SC5'- Maxima - Rep 1 | SC5' - Maxima - Rep 2 | SC5' - 42B - Rep 1 | SC5' - 42B - Rep 2 |
| Mean Reads per Cell | 280,128 | 269,343 | 280,848 | 257,745 |
| Valid Barcodes | 91.30% | 91.60% | 84.80% | 86.60% |
| Reads Mapped Confidently to Transcriptome | 58.80% | 60.20% | 50.00% | 52.70% |
| Reads Mapped Confidently to Intergenic Regions | 3.70% | 3.70% | 7.60% | 6.70% |
| Reads Mapped Confidently to Intronic Regions | 11.60% | 11.30% | 9.60% | 9.60% |
| Reads Mapped Confidently to Exonic Regions | 67.50% | 68.70% | 58.30% | 60.50% |
| Reads Mapped Antisense to Gene | 5.60% | 5.40% | 5.40% | 4.90% |
| Fraction rRNA reads | 2.10% | 2.00% | 6.50% | 5.60% |
| Fraction mtRNA reads | 0.80% | 0.80% | 2.80% | 2.30% |
| Fraction reads unmapped | 10.80% | 9.90% | 10.10% | 10.40% |
| Median genes per cell (50k raw reads per cell) | 602 | 651 | 1,365 | 1,367 |
| Median genes per cell (50k mapped cell-reads per cell) | 631 | 675 | 1,470 | 1,460 |
| Median UMI counts per cell (50k raw reads per cell) | 1,341 | 1,452 | 3,744 | 3,825 |
| Median UMI counts per cell (50k mapped cell-reads per cell) | 1,399 | 1,517 | 4,111 | 4,146 |
| Total genes detected >1500 nt (50k raw reads per cell) | 9,451 | 9,522 | 10,567 | 10,646 |
| Total genes detected >1500 nt (50k mapped cell-reads per cell) | 9,562 | 9,631 | 10,731 | 10,801 |

TABLE 10-continued

| Comparison between a CA-MMLV and Mutant Enzyme 42B in a 5'assay | | | | |
| --- | --- | --- | --- | --- |
| | CA-MMLV Enzyme | | Mutant 42B Enzyme | |
| Fraction UMI counts for genes <500 nt | 3.90% | 4.60% | 4.30% | 4.00% |
| Fraction UMI counts for genes 500-1000 nt | 37.70% | 37.60% | 34.60% | 34.60% |
| Fraction UMI counts for genes 1000-1500 nt | 25.50% | 25.20% | 25.00% | 24.90% |
| Fraction UMI counts for genes >1500 nt | 32.90% | 32.70% | 36.10% | 36.50% |
| Fraction ribosomal protein UMI counts | 36.60% | 36.30% | 30.60% | 30.20% |

As seen Tables 9 and 10, in both 3' and 5' assay formats, engineered RT enzyme 42B demonstrated an increase in sensitivity as measured by median UMIs detected per cell and median genes detected per cell. Additionally, enzyme 42B showed an increase in bias toward long genes as measured by the fraction of UMI counts for genes >1,500 nucleotides in length. In aggregate, the data shows that enzyme 42B unexpectedly exhibits different mapping rates to various types of RNA, different length bias, and, importantly, results in the generation of more complex cDNA libraries (more genes/cell and more UMIs/cell) than a comparable counterpart CA_MMLV, especially when utilized in a 5' mRNA assay.

While some embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An engineered reverse transcription enzyme comprising an amino acid sequence that is at least 95% identical to amino acids 26 to 671 of SEQ ID NO:3, wherein the amino acid sequence has a K at position 69, a P at position 139, an N at position 200, an R at position 302, a K at position 306, an F at position 313, a P at position 330, an amino acid that is not L at position 435, an A at position 448, a G at position 449, a K at position 454, an N at position 524, a W at position 603 and a K at position 607, wherein the positions correspond to positions in SEQ ID NO:3.

2. The engineered reverse transcription enzyme of claim 1, wherein the amino acid sequence comprises a K at position 435.

3. The engineered reverse transcription enzyme of claim 1, wherein the engineered reverse transcription enzyme lacks residues 1-20 of SEQ ID NO: 3.

4. The engineered reverse transcription enzyme of claim 1, wherein the engineered reverse transcription enzyme lacks residues 1-23 of SEQ ID NO: 3.

5. The engineered reverse transcription enzyme of claim 1, wherein said engineered reverse transcription enzyme further comprises an affinity tag.

6. The engineered reverse transcription enzyme of claim 5, wherein said affinity tag comprises at least 5 histidine amino acids.

7. The engineered reverse transcription enzyme of claim 1, wherein the engineered reverse transcription enzyme further comprises MRSSHHHHHHSSGLVPRGS (SEQ ID NO: 7) at the N-terminus of the engineered reverse transcription enzyme.

8. The engineered reverse transcription enzyme of claim 2, wherein said engineered reverse transcription enzyme comprises the amino acid sequence of SEQ ID NO: 6.

9. The engineered reverse transcription enzyme of claim 7, wherein said engineered reverse transcription enzyme comprises the amino acid sequence of SEQ ID NO: 5.

10. The engineered reverse transcription enzyme of claim 1, wherein the engineered reverse transcription enzyme comprises an amino acid sequence that is 100% identical to amino acids 26 to 671 of SEQ ID NO: 3.

*    *    *    *    *

SEQUENCE LISTING

```
<160> NUMBER OF SEQ ID NOS: 11

<210> SEQ ID NO 1
<211> LENGTH: 2043
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgggtagct cacatcacca tcatcatcat tcttctggtc tggtcccacg cggcagcact       60
tggctgtctg atttccctca ggcgtgggcc gaaacgggtg gcatgggtct ggcagtgcgt      120
caggcaccgc tgattattcc gctgaaagcg acgtcgaccc cggtgagcat caagcaatat      180
ccgatgtccc aagaggcgcg cttaggtatt aagccgcaca ttcagcgtct gctggatcaa      240
ggtattctgg ttccgtgtca gagcccgtgg aataccccgc ttctcccggt gaagaaaccg      300
ggcacgaacg attaccgtcc agtccaagac ttgcgcgaag ttaacaagcg cgttgaagat      360
attcacccga ccgtcccgaa cccgtacaat ctgctgagcg gtctgccgcc aagccaccaa      420
tggtacaccg tgctggatct gaaagatgct ttcttctgtc tgcgtctgca cccaaccagc      480
cagcctctgt ttgcatttga gtggcgtgac cctgagatgg gtattagcgg ccagctgacg      540
tggacccgcc tgccgcaagg ttttaagaat tcccctacgc tgtttgacga agcgctgcac      600
cgtgacctgg cggatttccg tatccagcac ccggacctga tcttgctgca gtacgttgat      660
gacctgttgc tggcggcgac gagcgagctg gattgccaac agggcacccg tgcgctgttg      720
```

-continued

```
cagaccttgg gtaacctggg ttatcgcgct agcgcgaaga aagcgcagat ttgccaaaaa    780
caagttaagt atctgggcta cctgttaaag gaaggccaac gttggctgac cgaagcccgc    840
aaagaaactg tcatgggtca gccgacccg aaaacgccac gccaactgcg tgagttcttg     900
ggcaccgcgg gtttctgccg cctgtggatc ccgggctttg ccgaaatggc agccccgctg    960
tatccgttga ccaagaccgg caccctgttc aactggggtc cggaccagca gaaagcgtac   1020
caagaaatta acaagcact gctgacggca ccggcgctgg gtctgccgga cctgaccaag    1080
ccgtttgagc tgttcgtgga tgagaagcaa ggttacgcga agggcgtgtt gacccagaaa   1140
ttgggtccgt ggcgtcgtcc ggttgcatac ctgtccaaga aactggaccc ggttgctgct   1200
ggttggccgc cttgcctgcg catggttgcc gctatcgcgg tgctgactaa agacgcgggt   1260
aagctgacga tgggtcaacc gctggtgatc aaggcaccgc atgcagtcga ggcccttgtt   1320
aagcaaccgc cagatagatg gctgagcaac gcgcgtatga cgcattacca ggcactgctg   1380
ttggacaccg atcgtgtgca gtttggcccg gtcgttgcgc tcaacccggc gaccctgctg   1440
ccgctcccgg aagaaggctt gcagcacaac tgtttggaca tcctggcaga ggcgcacggc   1500
actcgcccgg atctgacgga ccagccgctg ccggacgccg atcatacctg gtatacgaat   1560
ggtagcagcc tgttgcaaga gggtcagcgt aaggccggtg ccgcggtcac caccgagact   1620
gaagtgattt gggctaaagc attgcctgcg ggtaccagcg cgcagcgtgc cgagctgatc   1680
gcactgaccc aagcgctgaa aatggctgag ggtaagaaac tgaatgtgta cacggatagc   1740
cgttatgcct ttgcgaccgc ccacattcac ggcgagatct atcgccgtcg cggcctgctg   1800
acgtccgaag gcaaagagat caagaataaa gacgaaattc tggcgctgct gaaagcgctg   1860
ttcctgccga aacgtctgtc gatcatccat tgcccgggtc accagaaagg ccacagcgca   1920
gaggcgcgtg gtaatcgcat ggctgaccag gctgcgcgta aagccgcaat taccgaaacc   1980
ccggacacca gcacgctgct gatcgagaat agcagcccga acagccgtct gatcaattga   2040
taa                                                                 2043
```

<210> SEQ ID NO 2
<211> LENGTH: 679
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 2

```
Met Gly Ser Ser His His His His His His Ser Ser Gly Leu Val Pro
1               5                   10                  15

Arg Gly Ser Thr Trp Leu Ser Asp Phe Pro Gln Ala Trp Ala Glu Thr
            20                  25                  30

Gly Gly Met Gly Leu Ala Val Arg Gln Ala Pro Leu Ile Ile Pro Leu
        35                  40                  45

Lys Ala Thr Ser Thr Pro Val Ser Ile Lys Gln Tyr Pro Met Ser Gln
    50                  55                  60

Glu Ala Arg Leu Gly Ile Lys Pro His Ile Gln Arg Leu Leu Asp Gln
65                  70                  75                  80

Gly Ile Leu Val Pro Cys Gln Ser Pro Trp Asn Thr Pro Leu Leu Pro
                85                  90                  95

Val Lys Lys Pro Gly Thr Asn Asp Tyr Arg Pro Val Gln Asp Leu Arg
            100                 105                 110
```

```
Glu Val Asn Lys Arg Val Glu Asp Ile His Pro Thr Val Pro Asn Pro
        115                 120                 125

Tyr Asn Leu Leu Ser Gly Leu Pro Pro Ser His Gln Trp Tyr Thr Val
        130                 135                 140

Leu Asp Leu Lys Asp Ala Phe Phe Cys Leu Arg Leu His Pro Thr Ser
145                 150                 155                 160

Gln Pro Leu Phe Ala Phe Glu Trp Arg Asp Pro Glu Met Gly Ile Ser
                165                 170                 175

Gly Gln Leu Thr Trp Thr Arg Leu Pro Gln Gly Phe Lys Asn Ser Pro
                180                 185                 190

Thr Leu Phe Asp Glu Ala Leu His Arg Asp Leu Ala Asp Phe Arg Ile
                195                 200                 205

Gln His Pro Asp Leu Ile Leu Leu Gln Tyr Val Asp Asp Leu Leu Leu
        210                 215                 220

Ala Ala Thr Ser Glu Leu Asp Cys Gln Gln Gly Thr Arg Ala Leu Leu
225                 230                 235                 240

Gln Thr Leu Gly Asn Leu Gly Tyr Arg Ala Ser Ala Lys Lys Ala Gln
                245                 250                 255

Ile Cys Gln Lys Gln Val Lys Tyr Leu Gly Tyr Leu Leu Lys Glu Gly
                260                 265                 270

Gln Arg Trp Leu Thr Glu Ala Arg Lys Glu Thr Val Met Gly Gln Pro
                275                 280                 285

Thr Pro Lys Thr Pro Arg Gln Leu Arg Glu Phe Leu Gly Thr Ala Gly
        290                 295                 300

Phe Cys Arg Leu Trp Ile Pro Gly Phe Ala Glu Met Ala Ala Pro Leu
305                 310                 315                 320

Tyr Pro Leu Thr Lys Thr Gly Thr Leu Phe Asn Trp Gly Pro Asp Gln
                325                 330                 335

Gln Lys Ala Tyr Gln Glu Ile Lys Gln Ala Leu Leu Thr Ala Pro Ala
                340                 345                 350

Leu Gly Leu Pro Asp Leu Thr Lys Pro Phe Glu Leu Phe Val Asp Glu
                355                 360                 365

Lys Gln Gly Tyr Ala Lys Gly Val Leu Thr Gln Lys Leu Gly Pro Trp
        370                 375                 380

Arg Arg Pro Val Ala Tyr Leu Ser Lys Lys Leu Asp Pro Val Ala Ala
385                 390                 395                 400

Gly Trp Pro Pro Cys Leu Arg Met Val Ala Ala Ile Ala Val Leu Thr
                405                 410                 415

Lys Asp Ala Gly Lys Leu Thr Met Gly Gln Pro Leu Val Ile Lys Ala
                420                 425                 430

Pro His Ala Val Glu Ala Leu Val Lys Gln Pro Pro Asp Arg Trp Leu
        435                 440                 445

Ser Asn Ala Arg Met Thr His Tyr Gln Ala Leu Leu Leu Asp Thr Asp
        450                 455                 460

Arg Val Gln Phe Gly Pro Val Val Ala Leu Asn Pro Ala Thr Leu Leu
465                 470                 475                 480

Pro Leu Pro Glu Glu Gly Leu Gln His Asn Cys Leu Asp Ile Leu Ala
                485                 490                 495

Glu Ala His Gly Thr Arg Pro Asp Leu Thr Asp Gln Pro Leu Pro Asp
                500                 505                 510

Ala Asp His Thr Trp Tyr Thr Asn Gly Ser Ser Leu Leu Gln Glu Gly
        515                 520                 525

Gln Arg Lys Ala Gly Ala Ala Val Thr Thr Glu Thr Glu Val Ile Trp
```

```
        530              535              540

Ala Lys Ala Leu Pro Ala Gly Thr Ser Ala Gln Arg Ala Glu Leu Ile
545                 550              555              560

Ala Leu Thr Gln Ala Leu Lys Met Ala Glu Gly Lys Lys Leu Asn Val
                565              570              575

Tyr Thr Asp Ser Arg Tyr Ala Phe Ala Thr Ala His Ile His Gly Glu
                580              585              590

Ile Tyr Arg Arg Arg Gly Leu Leu Thr Ser Glu Gly Lys Glu Ile Lys
            595              600              605

Asn Lys Asp Glu Ile Leu Ala Leu Leu Lys Ala Leu Phe Leu Pro Lys
            610              615              620

Arg Leu Ser Ile Ile His Cys Pro Gly His Gln Lys Gly His Ser Ala
625                 630              635              640

Glu Ala Arg Gly Asn Arg Met Ala Asp Gln Ala Ala Arg Lys Ala Ala
                645              650              655

Ile Thr Glu Thr Pro Asp Thr Ser Thr Leu Leu Ile Glu Asn Ser Ser
                660              665              670

Pro Asn Ser Arg Leu Ile Asn
            675

<210> SEQ ID NO 3
<211> LENGTH: 671
<212> TYPE: PRT
<213> ORGANISM: Moloney murine leukemia virus

<400> SEQUENCE: 3

Thr Leu Asn Ile Glu Asp Glu His Arg Leu His Glu Thr Ser Lys Glu
1               5               10              15

Pro Asp Val Ser Leu Gly Ser Thr Trp Leu Ser Asp Phe Pro Gln Ala
            20              25              30

Trp Ala Glu Thr Gly Gly Met Gly Leu Ala Val Arg Gln Ala Pro Leu
        35              40              45

Ile Ile Pro Leu Lys Ala Thr Ser Thr Pro Val Ser Ile Lys Gln Tyr
    50              55              60

Pro Met Ser Gln Glu Ala Arg Leu Gly Ile Lys Pro His Ile Gln Arg
65              70              75              80

Leu Leu Asp Gln Gly Ile Leu Val Pro Cys Gln Ser Pro Trp Asn Thr
            85              90              95

Pro Leu Leu Pro Val Lys Lys Pro Gly Thr Asn Asp Tyr Arg Pro Val
            100             105             110

Gln Asp Leu Arg Glu Val Asn Lys Arg Val Glu Asp Ile His Pro Thr
            115             120             125

Val Pro Asn Pro Tyr Asn Leu Leu Ser Gly Leu Pro Pro Ser His Gln
        130             135             140

Trp Tyr Thr Val Leu Asp Leu Lys Asp Ala Phe Phe Cys Leu Arg Leu
145             150             155             160

His Pro Thr Ser Gln Pro Leu Phe Ala Phe Glu Trp Arg Asp Pro Glu
                165             170             175

Met Gly Ile Ser Gly Gln Leu Thr Trp Thr Arg Leu Pro Gln Gly Phe
            180             185             190

Lys Asn Ser Pro Thr Leu Phe Asp Glu Ala Leu His Arg Asp Leu Ala
            195             200             205

Asp Phe Arg Ile Gln His Pro Asp Leu Ile Leu Leu Gln Tyr Val Asp
    210             215             220
```

-continued

```
Asp Leu Leu Leu Ala Ala Thr Ser Glu Leu Asp Cys Gln Gln Gly Thr
225             230             235             240

Arg Ala Leu Leu Gln Thr Leu Gly Asn Leu Gly Tyr Arg Ala Ser Ala
            245             250             255

Lys Lys Ala Gln Ile Cys Gln Lys Gln Val Lys Tyr Leu Gly Tyr Leu
            260             265             270

Leu Lys Glu Gly Gln Arg Trp Leu Thr Glu Ala Arg Lys Glu Thr Val
        275             280             285

Met Gly Gln Pro Thr Pro Lys Thr Pro Arg Gln Leu Arg Glu Phe Leu
    290             295             300

Gly Thr Ala Gly Phe Cys Arg Leu Trp Ile Pro Gly Phe Ala Glu Met
305             310             315             320

Ala Ala Pro Leu Tyr Pro Leu Thr Lys Thr Gly Thr Leu Phe Asn Trp
            325             330             335

Gly Pro Asp Gln Gln Lys Ala Tyr Gln Glu Ile Lys Gln Ala Leu Leu
            340             345             350

Thr Ala Pro Ala Leu Gly Leu Pro Asp Leu Thr Lys Pro Phe Glu Leu
            355             360             365

Phe Val Asp Glu Lys Gln Gly Tyr Ala Lys Gly Val Leu Thr Gln Lys
    370             375             380

Leu Gly Pro Trp Arg Arg Pro Val Ala Tyr Leu Ser Lys Lys Leu Asp
385             390             395             400

Pro Val Ala Ala Gly Trp Pro Pro Cys Leu Arg Met Val Ala Ala Ile
            405             410             415

Ala Val Leu Thr Lys Asp Ala Gly Lys Leu Thr Met Gly Gln Pro Leu
            420             425             430

Val Ile Leu Ala Pro His Ala Val Glu Ala Leu Val Lys Gln Pro Pro
            435             440             445

Asp Arg Trp Leu Ser Asn Ala Arg Met Thr His Tyr Gln Ala Leu Leu
    450             455             460

Leu Asp Thr Asp Arg Val Gln Phe Gly Pro Val Val Ala Leu Asn Pro
465             470             475             480

Ala Thr Leu Leu Pro Leu Pro Glu Glu Gly Leu Gln His Asn Cys Leu
            485             490             495

Asp Ile Leu Ala Glu Ala His Gly Thr Arg Pro Asp Leu Thr Asp Gln
            500             505             510

Pro Leu Pro Asp Ala Asp His Thr Trp Tyr Thr Asp Gly Ser Ser Leu
    515             520             525

Leu Gln Glu Gly Gln Arg Lys Ala Gly Ala Ala Val Thr Thr Glu Thr
    530             535             540

Glu Val Ile Trp Ala Lys Ala Leu Pro Ala Gly Thr Ser Ala Gln Arg
545             550             555             560

Ala Glu Leu Ile Ala Leu Thr Gln Ala Leu Lys Met Ala Glu Gly Lys
            565             570             575

Lys Leu Asn Val Tyr Thr Asp Ser Arg Tyr Ala Phe Ala Thr Ala His
            580             585             590

Ile His Gly Glu Ile Tyr Arg Arg Arg Gly Leu Leu Thr Ser Glu Gly
        595             600             605

Lys Glu Ile Lys Asn Lys Asp Glu Ile Leu Ala Leu Leu Lys Ala Leu
    610             615             620

Phe Leu Pro Lys Arg Leu Ser Ile Ile His Cys Pro Gly His Gln Lys
625             630             635             640

Gly His Ser Ala Glu Ala Arg Gly Asn Arg Met Ala Asp Gln Ala Ala
```

```
                 645              650              655

Arg Lys Ala Ala Ile Thr Glu Thr Pro Asp Thr Ser Thr Leu Leu
         660              665              670

<210> SEQ ID NO 4
<211> LENGTH: 2043
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgggtagct cacatcacca tcatcatcat tcttctggtc tggtcccacg cggcagcact      60
tggctgtctg atttccctca ggcgtgggcc gaaacgggtg gcatgggtct ggcagtgcgt     120
caggcaccgc tgattattcc gctgaaagcg acgtcgaccc cggtgagcat caagcaatat     180
ccgatgtccc aaaaggcgcg cttaggtatt aagccgcaca ttcagcgtct gctggatcaa     240
ggtattctgg ttccgtgtca gagcccgtgg aataccccgc ttctcccggt gaagaaaccg     300
ggcacgaacg attaccgtcc agtccaagac ttgcgcgaag ttaacaagcg cgttgaagat     360
attcacccga ccgtcccgaa cccgtacaat ctgctgagcg gtccgccgcc aagccaccaa     420
tggtacaccg tgctggatct gaaagatgct ttcttctgtc tgcgtctgca cccaaccagc     480
cagcctctgt ttgcatttga gtggcgtgac cctgagatgg gtattagcgg ccagctgacg     540
tggacccgcc tgccgcaagg ttttaagaat tcccctacgc tgtttaacga agcgctgcac     600
cgtgacctgc cggatttccg tatccagcac ccggacctga tcttgctgca gtacgttgat     660
gacctgttgc tggcggcgac gagcgagctg gattgccaac agggcacccg tgcgctgttg     720
cagaccttgg gtaacctggg ttatcgcgct agcgcgaaga aagcgcagat ttgccaaaaa     780
caagttaagt atctgggcta cctgttaaag gaaggccaac gttggctgac cgaagcccgc     840
aaagaaactg tcatgggtca gccgaccccg aaaacgccac gccaactgcg taggttcttg     900
ggcaaagcgg gtttctgccg cctgttcatc ccgggctttg ccgaaatggc agccccgctg     960
tatccgttga ccaagccggg caccctgttc aactggggtc cggaccagca gaaagcgtac    1020
caagaaatta acaagcact gctgacggca ccggcgctgg tctgccgga cctgaccaag    1080 ccgtttgagc tgttcgtgga tgagaagcaa ggttacgcga agggcgtgtt gacccagaaa    1140
ttgggtccgt ggcgtcgtcc ggttgcatac ctgtccaaga aactggaccc ggttgctgct    1200
ggttggccgc cttgcctgcg catggttgcc gctatcgcgg tgctgactaa agacgcgggt    1260
aagctgacga tgggtcaacc gctggtgatc aaggcaccgc atgcagtcga ggcccttgtt    1320
aagcaaccgg caggcagatg gctgagcaag gcgcgtatga cgcattacca ggcactgctg    1380
ttggacaccg atcgtgtgca gtttggcccg gtcgttgcgc tcaacccggc gaccctgctg    1440
ccgctcccgg aagaaggctt gcagcacaac tgtttggaca tcctggcaga ggcgcacggc    1500
actcgcccgg atctgacgga ccagccgctg ccggacgccg atcatacctg gtatacgaat    1560
ggtagcagcc tgttgcaaga gggtcagcgt aaggccggtg ccgcggtcac caccgagact    1620
gaagtgattt gggctaaagc attgcctgcg ggtaccagcg cgcagcgtgc cgagctgatc    1680
gcactgaccc aagcgctgaa aatggctgag ggtaagaaac tgaatgtgta cacggatagc    1740
cgttatgcct ttgcgaccgc ccacattcac ggcgagatct atcgccgtcg cggctggctg    1800
acgtccaaag gcaaagagat caagaataaa gacgaaattc tggcgctgct gaaagcgctg    1860
ttcctgccga aacgtctgtc gatcatccat tgcccggggtc accagaaagg ccacagcgca    1920
```
gaggcgcgtg gtaatcgcat ggctgaccag gctgcgcgta aagccgcaat taccgaaacc 1980
ccggacacca gcacgctgct gatcgagaat agcagcccga acagccgtct gatcaattga 2040
taa 2043

<210> SEQ ID NO 5
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Ser Ser His His His His His His Ser Ser Gly Leu Val Pro
1               5                   10                  15

Arg Gly Ser Thr Trp Leu Ser Asp Phe Pro Gln Ala Trp Ala Glu Thr
            20                  25                  30

Gly Gly Met Gly Leu Ala Val Arg Gln Ala Pro Leu Ile Ile Pro Leu
        35                  40                  45

Lys Ala Thr Ser Thr Pro Val Ser Ile Lys Gln Tyr Pro Met Ser Gln
    50                  55                  60

Lys Ala Arg Leu Gly Ile Lys Pro His Ile Gln Arg Leu Leu Asp Gln
65                  70                  75                  80

Gly Ile Leu Val Pro Cys Gln Ser Pro Trp Asn Thr Pro Leu Leu Pro
                85                  90                  95

Val Lys Lys Pro Gly Thr Asn Asp Tyr Arg Pro Val Gln Asp Leu Arg
            100                 105                 110

Glu Val Asn Lys Arg Val Glu Asp Ile His Pro Thr Val Pro Asn Pro
            115                 120                 125

Tyr Asn Leu Leu Ser Gly Pro Pro Ser His Gln Trp Tyr Thr Val
            130                 135                 140

Leu Asp Leu Lys Asp Ala Phe Phe Cys Leu Arg Leu His Pro Thr Ser
145                 150                 155                 160

Gln Pro Leu Phe Ala Phe Glu Trp Arg Asp Pro Glu Met Gly Ile Ser
                165                 170                 175

Gly Gln Leu Thr Trp Thr Arg Leu Pro Gln Gly Phe Lys Asn Ser Pro
                180                 185                 190

Thr Leu Phe Asn Glu Ala Leu His Arg Asp Leu Ala Asp Phe Arg Ile
            195                 200                 205

Gln His Pro Asp Leu Ile Leu Leu Gln Tyr Val Asp Asp Leu Leu Leu
            210                 215                 220

Ala Ala Thr Ser Glu Leu Asp Cys Gln Gln Gly Thr Arg Ala Leu Leu
225                 230                 235                 240

Gln Thr Leu Gly Asn Leu Gly Tyr Arg Ala Ser Ala Lys Lys Ala Gln
                245                 250                 255

Ile Cys Gln Lys Gln Val Lys Tyr Leu Gly Tyr Leu Leu Lys Glu Gly
            260                 265                 270

Gln Arg Trp Leu Thr Glu Ala Arg Lys Glu Thr Val Met Gly Gln Pro
            275                 280                 285

Thr Pro Lys Thr Pro Arg Gln Leu Arg Arg Phe Leu Gly Lys Ala Gly
    290                 295                 300

Phe Cys Arg Leu Phe Ile Pro Gly Phe Ala Glu Met Ala Ala Pro Leu
305                 310                 315                 320

Tyr Pro Leu Thr Lys Pro Gly Thr Leu Phe Asn Trp Gly Pro Asp Gln

```
                     325                330                335

Gln Lys Ala Tyr Gln Glu Ile Lys Gln Ala Leu Leu Thr Ala Pro Ala
                 340                345                350

Leu Gly Leu Pro Asp Leu Thr Lys Pro Phe Glu Leu Phe Val Asp Glu
             355                360                365

Lys Gln Gly Tyr Ala Lys Gly Val Leu Thr Gln Lys Leu Gly Pro Trp
         370                375                380

Arg Arg Pro Val Ala Tyr Leu Ser Lys Lys Leu Asp Pro Val Ala Ala
     385                390                395                400

Gly Trp Pro Pro Cys Leu Arg Met Val Ala Ala Ile Ala Val Leu Thr
                 405                410                415

Lys Asp Ala Gly Lys Leu Thr Met Gly Gln Pro Leu Val Ile Lys Ala
                 420                425                430

Pro His Ala Val Glu Ala Leu Val Lys Gln Pro Ala Gly Arg Trp Leu
             435                440                445

Ser Lys Ala Arg Met Thr His Tyr Gln Ala Leu Leu Leu Asp Thr Asp
     450                455                460

Arg Val Gln Phe Gly Pro Val Val Ala Leu Asn Pro Ala Thr Leu Leu
     465                470                475                480

Pro Leu Pro Glu Glu Gly Leu Gln His Asn Cys Leu Asp Ile Leu Ala
                 485                490                495

Glu Ala His Gly Thr Arg Pro Asp Leu Thr Asp Gln Pro Leu Pro Asp
                 500                505                510

Ala Asp His Thr Trp Tyr Thr Asn Gly Ser Ser Leu Leu Gln Glu Gly
                 515                520                525

Gln Arg Lys Ala Gly Ala Ala Val Thr Thr Glu Thr Glu Val Ile Trp
     530                535                540

Ala Lys Ala Leu Pro Ala Gly Thr Ser Ala Gln Arg Ala Glu Leu Ile
     545                550                555                560

Ala Leu Thr Gln Ala Leu Lys Met Ala Glu Gly Lys Lys Leu Asn Val
                 565                570                575

Tyr Thr Asp Ser Arg Tyr Ala Phe Ala Thr Ala His Ile His Gly Glu
                 580                585                590

Ile Tyr Arg Arg Arg Gly Trp Leu Thr Ser Lys Gly Lys Glu Ile Lys
             595                600                605

Asn Lys Asp Glu Ile Leu Ala Leu Leu Lys Ala Leu Phe Leu Pro Lys
         610                615                620

Arg Leu Ser Ile Ile His Cys Pro Gly His Gln Lys Gly His Ser Ala
     625                630                635                640

Glu Ala Arg Gly Asn Arg Met Ala Asp Gln Ala Ala Arg Lys Ala Ala
                 645                650                655

Ile Thr Glu Thr Pro Asp Thr Ser Thr Leu Leu Ile Glu Asn Ser Ser
             660                665                670

Pro Asn Ser Arg Leu Ile Asn
         675
```

```
<210> SEQ ID NO 6
<211> LENGTH: 648
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Thr Trp Leu Ser Asp Phe Pro Gln Ala Trp Ala Glu Thr Gly Gly Met
1               5                   10                  15

Gly Leu Ala Val Arg Gln Ala Pro Leu Ile Ile Pro Leu Lys Ala Thr
            20                  25                  30

Ser Thr Pro Val Ser Ile Lys Gln Tyr Pro Met Ser Gln Lys Ala Arg
        35                  40                  45

Leu Gly Ile Lys Pro His Ile Gln Arg Leu Leu Asp Gln Gly Ile Leu
    50                  55                  60

Val Pro Cys Gln Ser Pro Trp Asn Thr Pro Leu Leu Pro Val Lys Lys
65                  70                  75                  80

Pro Gly Thr Asn Asp Tyr Arg Pro Val Gln Asp Leu Arg Glu Val Asn
                85                  90                  95

Lys Arg Val Glu Asp Ile His Pro Thr Val Pro Asn Pro Tyr Asn Leu
            100                 105                 110

Leu Ser Gly Pro Pro Ser His Gln Trp Tyr Thr Val Leu Asp Leu
        115                 120                 125

Lys Asp Ala Phe Phe Cys Leu Arg Leu His Pro Thr Ser Gln Pro Leu
    130                 135                 140

Phe Ala Phe Glu Trp Arg Asp Pro Glu Met Gly Ile Ser Gly Gln Leu
145                 150                 155                 160

Thr Trp Thr Arg Leu Pro Gln Gly Phe Lys Asn Ser Pro Thr Leu Phe
            165                 170                 175

Asn Glu Ala Leu His Arg Asp Leu Ala Asp Phe Arg Ile Gln His Pro
            180                 185                 190

Asp Leu Ile Leu Leu Gln Tyr Val Asp Asp Leu Leu Leu Ala Ala Thr
            195                 200                 205

Ser Glu Leu Asp Cys Gln Gln Gly Thr Arg Ala Leu Leu Gln Thr Leu
    210                 215                 220

Gly Asn Leu Gly Tyr Arg Ala Ser Ala Lys Lys Ala Gln Ile Cys Gln
225                 230                 235                 240

Lys Gln Val Lys Tyr Leu Gly Tyr Leu Leu Lys Glu Gly Gln Arg Trp
                245                 250                 255

Leu Thr Glu Ala Arg Lys Glu Thr Val Met Gly Gln Pro Thr Pro Lys
            260                 265                 270

Thr Pro Arg Gln Leu Arg Arg Phe Leu Gly Lys Ala Gly Phe Cys Arg
        275                 280                 285

Leu Phe Ile Pro Gly Phe Ala Glu Met Ala Ala Pro Leu Tyr Pro Leu
    290                 295                 300

Thr Lys Pro Gly Thr Leu Phe Asn Trp Gly Pro Asp Gln Gln Lys Ala
305                 310                 315                 320

Tyr Gln Glu Ile Lys Gln Ala Leu Leu Thr Ala Pro Ala Leu Gly Leu
                325                 330                 335

Pro Asp Leu Thr Lys Pro Phe Glu Leu Phe Val Asp Glu Lys Gln Gly
            340                 345                 350

Tyr Ala Lys Gly Val Leu Thr Gln Lys Leu Gly Pro Trp Arg Arg Pro
        355                 360                 365

Val Ala Tyr Leu Ser Lys Lys Leu Asp Pro Val Ala Ala Gly Trp Pro
    370                 375                 380

Pro Cys Leu Arg Met Val Ala Ala Ile Ala Val Leu Thr Lys Asp Ala
385                 390                 395                 400

Gly Lys Leu Thr Met Gly Gln Pro Leu Val Ile Lys Ala Pro His Ala
                405                 410                 415

Val Glu Ala Leu Val Lys Gln Pro Ala Gly Arg Trp Leu Ser Lys Ala
```

-continued

```
              420              425              430

Arg Met Thr His Tyr Gln Ala Leu Leu Leu Asp Thr Asp Arg Val Gln
        435              440              445

Phe Gly Pro Val Val Ala Leu Asn Pro Ala Thr Leu Leu Pro Leu Pro
        450              455              460

Glu Glu Gly Leu Gln His Asn Cys Leu Asp Ile Leu Ala Glu Ala His
465              470              475              480

Gly Thr Arg Pro Asp Leu Thr Asp Gln Pro Leu Pro Asp Ala Asp His
                485              490              495

Thr Trp Tyr Thr Asn Gly Ser Ser Leu Leu Gln Glu Gly Gln Arg Lys
            500              505              510

Ala Gly Ala Ala Val Thr Thr Glu Thr Glu Val Ile Trp Ala Lys Ala
        515              520              525

Leu Pro Ala Gly Thr Ser Ala Gln Arg Ala Glu Leu Ile Ala Leu Thr
        530              535              540

Gln Ala Leu Lys Met Ala Glu Gly Lys Lys Leu Asn Val Tyr Thr Asp
545              550              555              560

Ser Arg Tyr Ala Phe Ala Thr Ala His Ile His Gly Glu Ile Tyr Arg
                565              570              575

Arg Arg Gly Trp Leu Thr Ser Lys Gly Lys Glu Ile Lys Asn Lys Asp
                580              585              590

Glu Ile Leu Ala Leu Leu Lys Ala Leu Phe Leu Pro Lys Arg Leu Ser
            595              600              605

Ile Ile His Cys Pro Gly His Gln Lys Gly His Ser Ala Glu Ala Arg
        610              615              620

Gly Asn Arg Met Ala Asp Gln Ala Ala Arg Lys Ala Ala Ile Thr Glu
625              630              635              640

Thr Pro Asp Thr Ser Thr Leu Leu
            645
```

```
<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Arg Ser Ser His His His His His His Ser Ser Gly Leu Val Pro
1               5                   10                  15

Arg Gly Ser
```

```
<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Arg Ser Ser His His His His His His Ser Ser Gly Leu Val Pro
1               5                   10                  15

Arg
```

```
<210> SEQ ID NO 9
<211> LENGTH: 6
```

-continued

```
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aaaaaaaaaa aaaaaa                                                              16

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaaaaaaaaa a                                                                   11
```